United States Patent
Hirai et al.

(10) Patent No.: US 10,464,966 B2
(45) Date of Patent: Nov. 5, 2019

(54) PRECIPITATION PROMOTER AND PRECIPITATION METHOD IN WHICH SAME IS USED

(71) Applicant: AJINOMOTO CO., INC., Tokyo (JP)

(72) Inventors: Kunihiro Hirai, Kawasaki (JP); Satoshi Katayama, Kawasaki (JP); Naoko Hirose, Kawasaki (JP); Ken Yamashita, Kawasaki (JP); Taisuke Ichimaru, Kawasaki (JP); Daisuke Takahashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 68 days.

(21) Appl. No.: 15/655,280

(22) Filed: Jul. 20, 2017

(65) Prior Publication Data
US 2017/0320904 A1  Nov. 9, 2017

Related U.S. Application Data

(63) Continuation of application No. PCT/JP2016/051757, filed on Jan. 21, 2016.

(30) Foreign Application Priority Data

Jan. 21, 2015  (JP) .................................. 2015-009720

(51) Int. Cl.
| | |
|---|---|
| *C07K 1/32* | (2006.01) |
| *C07H 21/02* | (2006.01) |
| *C07K 1/30* | (2006.01) |
| *C07H 21/04* | (2006.01) |
| *C07H 21/00* | (2006.01) |
| *C07H 23/00* | (2006.01) |
| *C07F 7/18* | (2006.01) |
| *C07C 43/10* | (2006.01) |
| *C07C 43/205* | (2006.01) |
| *C07C 49/84* | (2006.01) |
| *C07C 69/157* | (2006.01) |
| *C07C 69/78* | (2006.01) |
| *C07C 233/47* | (2006.01) |
| *C07D 295/108* | (2006.01) |
| *C07C 69/017* | (2006.01) |
| *C07C 69/24* | (2006.01) |
| *C07C 69/757* | (2006.01) |
| *C07C 69/92* | (2006.01) |
| *C07C 69/94* | (2006.01) |
| *C07C 43/23* | (2006.01) |

(52) U.S. Cl.
CPC ............ *C07H 23/00* (2013.01); *C07C 43/10* (2013.01); *C07C 43/2055* (2013.01); *C07C 43/23* (2013.01); *C07C 49/84* (2013.01); *C07C 69/017* (2013.01); *C07C 69/157* (2013.01); *C07C 69/24* (2013.01); *C07C 69/757* (2013.01); *C07C 69/78* (2013.01); *C07C 69/92* (2013.01); *C07C 69/94* (2013.01); *C07C 233/47* (2013.01); *C07D 295/108* (2013.01); *C07F 7/1804* (2013.01); *C07H 21/00* (2013.01); *C07H 21/02* (2013.01); *C07H 21/04* (2013.01); *C07K 1/30* (2013.01); *C07K 1/306* (2013.01); *C07K 1/32* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 2,694,635 A | 11/1954 | Ilmari et al. | |
| 3,818,089 A * | 6/1974 | Bayley .................... | C07C 43/20 436/128 |
| 5,324,747 A | 6/1994 | Carson et al. | |
| 5,446,189 A | 8/1995 | Carson et al. | |
| 5,972,613 A | 10/1999 | Somack et al. | |
| 6,815,541 B1 | 11/2004 | Usui et al. | |
| 8,362,217 B2 * | 1/2013 | Moya ....................... | C07K 1/32 424/177.1 |
| 9,029,504 B2 | 5/2015 | Takahashi | |
| 9,670,121 B2 * | 6/2017 | Takahashi ............... | C07C 43/23 |
| 2010/0240667 A1 | 9/2010 | Takahashi | |
| 2010/0249374 A1 | 9/2010 | Takahashi | |
| 2011/0160433 A1 | 6/2011 | Takahashi | |
| 2012/0071640 A1 | 3/2012 | Mazur et al. | |
| 2012/0296074 A1 | 11/2012 | Hirai et al. | |

(Continued)

FOREIGN PATENT DOCUMENTS

| | | |
|---|---|---|
| EP | 0 579 066 A2 | 1/1994 |
| EP | 2 415 744 A1 | 2/2012 |

(Continued)

OTHER PUBLICATIONS

English translation of JP2000-044493 downloaded from https://www.j-platpat.inpit.go.jp/web/all/top/BTmTopEnglishPage (Year: 2000).*

Miyako et al., "Solubility enhancement of hydrophobic compounds by cosolvents: Role of solute hydrophobicity on the solubilization effect" International Journal of Pharmaceutics vol. 393 pp. 48-54 (Year: 2010).*

(Continued)

*Primary Examiner* — Eric Olson
(74) *Attorney, Agent, or Firm* — Oblon, McClelland, Maier & Neustadt, L.L.P.

(57) ABSTRACT

Precipitation promoters, which are an organic compound having one or more linear aliphatic hydrocarbon groups having not less than 10 carbon atoms, wherein the aliphatic hydrocarbon group has not less than 20 carbon atoms in total are useful for precipitating an organic compound protected by an organic group having one or more aliphatic hydrocarbon groups having not less than 10 carbon atoms from a solvent.

37 Claims, No Drawings
Specification includes a Sequence Listing.

(56) References Cited

U.S. PATENT DOCUMENTS

| | | |
|---|---|---|
| 2014/0046022 A1 | 2/2014 | Takahashi |
| 2014/0080999 A1 | 3/2014 | Takahashi |
| 2014/0088291 A1 | 3/2014 | Takahashi |
| 2014/0213761 A1 | 7/2014 | Takahashi |
| 2014/0296483 A1 | 10/2014 | Takahashi |
| 2014/0371424 A1 | 12/2014 | Takahashi |
| 2015/0315229 A1* | 11/2015 | Nonogawa ........... C07H 19/067 536/26.7 |
| 2016/0076033 A1 | 3/2016 | Torii et al. |

FOREIGN PATENT DOCUMENTS

| | | | |
|---|---|---|---|
| JP | 6-157388 A | | 6/1994 |
| JP | 7-238101 A | | 9/1995 |
| JP | 2000-044493 | * | 2/2000 ............ C07B 61/00 |
| JP | 2001-526182 A | | 12/2001 |
| JP | 2012-513450 A | | 6/2012 |
| WO | WO 97/07207 A1 | | 2/1997 |
| WO | WO 2010/104169 A1 | | 9/2010 |
| WO | WO 2010/113939 A1 | | 10/2010 |
| WO | WO 2011/078295 A1 | | 6/2011 |
| WO | WO 2012/157723 A1 | | 11/2012 |
| WO | WO 2012/165545 A1 | | 12/2012 |
| WO | WO 2012/165546 A1 | | 12/2012 |
| WO | WO 2013/089241 A1 | | 6/2013 |
| WO | WO 2014/189142 A1 | | 11/2014 |

OTHER PUBLICATIONS

Andrea K. Bartram, et al. "Nucleic acid contamination of glycogen used in nucleic acid precipitation and assessment of linear polyacrylamide as an alternative co-precipitant", BioTechniques, vol. 47, No. 6, 2009, pp. 1019-1022.

Extended European Search Report dated Aug. 16, 2018 in corresponding European Patent Application No. 16740270.0 citing documents AA, AO, AP, AQ and AX therein, 3 pages.

Baumann W. J. et al., "Reactions of Aliphatic Methanesulfonates. II. Syntheses of Long-Chain Di- and Trialkyl Glyceryl Ethers", Journal Of Organic Chemistry, vol. 31, No. 2, XP003010360, Jan. 1, 1966, pp. 498-500.

* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tcccgcctgt gacatgcatt                                               20
```

PRECIPITATION PROMOTER AND PRECIPITATION METHOD IN WHICH SAME IS USED

CROSS REFERENCES TO RELATED APPLICATIONS

This application is a continuation of International Patent Application No. PCT/JP2016/051757, filed on Jan. 21, 2016, and claims priority to Japanese Patent Application No. 2015-009720, filed on Jan. 21, 2015, both of which are incorporated herein by reference in their entireties.

BACKGROUND OF THE INVENTION

Field of the Invention

The present invention relates to precipitation promoters which are useful for precipitating an organic compound (e.g., an oligonucleotide, peptide, etc.) in a solution, and precipitation methods using the same.

DISCUSSION OF THE BACKGROUND

The synthesis method of oligonucleotides includes a phosphate triester method, an H-phosphonate method, a phosphoramidite method and the like, and solid phase synthesis (solid phase method) using a phosphoramidite method is most widely used at present. As a synthesis method of peptide, moreover, solid phase synthesis is widely used. The solid phase method is advantageous from the aspect of speed, since process has been optimized and automation has progressed. However, it is associated with defects in that scaling-up is limited due to facility restriction, reagents and starting materials are used in excess, and confirmation of the progress status of the reaction in an intermediate step, analysis of intermediate structure and the like are difficult. On the other hand, synthesis methods of oligonucleotides and peptides by a liquid phase method have also been studied. However, since the operation is complicated and the yield is low, a large-scale, rapid synthesis of long oligonucleotide and peptide is difficult.

In recent years, in an attempt to solve the respective defects of the solid phase method and the liquid phase method, there have been reported, in the liquid phase method, a synthesis method of oligonucleotide, which uses a nucleoside protected by an organic group having one or more long chain aliphatic hydrocarbon groups (pseudo solid phase protecting group) (see WO 2012/157723 and WO 2014/189142, both of which are incorporated herein by referenced in their entireties), and a synthesis method of peptide, which uses a peptide having a pseudo solid phase protecting group (see WO 2010/104169, WO 2010/113939, and WO 2011/078295, all of which are incorporated herein by referenced in their entireties). In these synthesis methods, for example, the object product is recovered by dissolving oligonucleotide or peptide having a hydrophobic pseudo solid phase protecting group in a non-polar solvent, and adding a polar solvent to allow for precipitation of these compounds from a mixed solvent of the non-polar solvent and the polar solvent (solid-liquid separation).

SUMMARY OF THE INVENTION

In liquid phase synthesis of an organic compound such as oligonucleotide, peptide and the like, which uses such pseudo solid phase protecting group, more efficient precipitation of these compounds in a solvent to improve the recovery rate of the compounds has been desired.

The present invention has been made taking note of the above-mentioned situation, and aims to improve a recovery rate of an organic compound having a pseudo solid phase protecting group, when the organic compound is precipitated in a solvent.

The present inventors have conducted intensive studies in an attempt to achieve the aforementioned object and found that precipitation of an organic compound having a hydrophobic group or pseudo solid phase protecting group can be promoted by using a particular precipitation promoter, and the recovery rate and the can be improved. The present invention based on these findings is as described below.

Thus, the present invention provides:

(1) A precipitation promoter for precipitating an organic compound protected by an organic group having one or more aliphatic hydrocarbon groups having not less than 10 carbon atoms in a solvent, which has one or more linear aliphatic hydrocarbon groups having not less than 10 carbon atoms, wherein the aforementioned aliphatic hydrocarbon group in the precipitation promoter has not less than 20 carbon atoms in total.

(2) The precipitation promoter of the aforementioned (1), wherein the linear aliphatic hydrocarbon group having not less than 10 carbon atoms in the precipitation promoter is a group selected from a linear $C_{10-40}$ alkyl group and a linear $C_{10-40}$ alkenyl group.

(3) The precipitation promoter of the aforementioned (1) or (2), wherein the aliphatic hydrocarbon group having not less than 10 carbon atoms of the organic group is linear.

(4) The precipitation promoter of the aforementioned (1) or (2), wherein the aliphatic hydrocarbon group having not less than 10 carbon atoms of the organic group is a group selected from a linear $C_{10-40}$ alkyl group and a linear $C_{10-40}$ alkenyl group.

(5) The precipitation promoter of any one of the aforementioned (1) to (4), which is (1) an organic compound having one or more structures represented by the formula (G):

wherein each $R^1$ is independently a linear $C_{10-40}$ alkyl group;

each $X^1$ is independently a single bond, —O—, —C(=O)—, —C(=O)O—, —OC(=O)—, —C(=O)NH— or —NHC(=O)—;

ring $A^1$ is an optionally substituted $C_{3-14}$ hydrocarbon ring; and n is an integer of 1 to 4, or (2) optionally substituted $C_{1-10}$ alkane having one or more linear $C_{10-40}$ alkyl groups via a group selected from the group consisting of —O—, —C(=O)—, —C(=O)O—, —OC(=O)—, —C(=O)NH— and —NHC(=O)—.

(6) The precipitation promoter of any one of the aforementioned (1) to (4), which is (1) a compound represented by the formula (I):

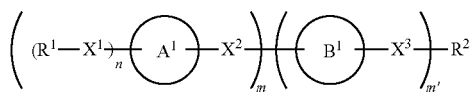

(I)

wherein
each $R^1$ is independently a linear $C_{10-40}$ alkyl group;
each $X^1$ is independently a single bond, —O—, —C(=O)—, —C(=O)O—, —OC(=O)—, —C(=O)NH— or —NHC(=O)—;
ring $A^1$ and ring $B^1$ are each independently an optionally substituted $C_{3-14}$ hydrocarbon ring;
each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$—, —$(CH_2)_p$—OC(=O)—$(CH_2)_q$—, —$(CH_2)_p$—C(=O)NH—$(CH_2)_q$— or —$(CH_2)_p$—NHC(=O)—$(CH_2)_q$— (p and q are each independently an integer of 0-3);
$X^3$ is a single bond, —$(CH_2)_r$—O—, —$(CH_2)_r$—C(=O)—, —$(CH_2)_r$, —C(=O)O—, —$(CH_2)_r$—OC(=O)—, —$(CH_2)_r$—C(=O)NH—$(CH_2)_r$—NHC(=O)— (r is an integer of 0-3);
$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted monocyclic heterocyclic group or a tri($C_{1-6}$ alkyl)silyl group;
n and m are each independently an integer of 1 to 4;
m' is 0 or 1 when m is 1, and 1 when m is 2, 3 or 4, or (2) optionally substituted $C_{1-10}$ alkane having one or more linear $C_{10-40}$ alkyl groups via a group selected from the group consisting of —O—, —C(=O)—, —C(=O)O—, —OC(=O)—, —C(=O)NH— and —NHC(=O)—.

(7) The precipitation promoter of the aforementioned (6), wherein $R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group or an optionally substituted monocyclic heterocyclic group.

(8) The precipitation promoter of any one of the aforementioned (1) to (4), which is a compound represented by the formula (II):

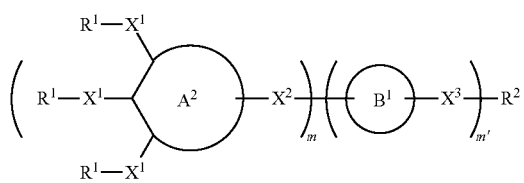

(II)

wherein
each $R^1$ is independently a linear $C_{10-40}$ alkyl group;
each $X^1$ is independently a single bond, —O—, —C(=O)—, —C(=O)O—, —OC(=O)—, —C(=O)NH— or —NHC(=O)—;
ring $A^2$ and ring $B^1$ are each independently an optionally substituted $C_{3-14}$ hydrocarbon ring;
each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$—, —$(CH_2)_p$—OC(=O)—$(CH_2)_q$—, —$(CH_2)_p$—C(=O)NH—$(CH_2)_q$— or —$(CH_2)_p$—NHC(=O)—$(CH_2)_q$— (p and q are each independently an integer of 0-3);
$X^3$ is a single bond, —$(CH_2)_r$—O—, —$(CH_2)_r$—C(=O)—, —$(CH_2)_r$, —C(=O)O—, —$(CH_2)_r$—OC(=O)—, —$(CH_2)_r$—C(=O)NH— or —$(CH_2)_r$—NHC(=O)— (r is an integer of 0-3);
$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted monocyclic heterocyclic group or a tri($C_{1-6}$ alkyl)silyl group;
m is an integer of 1 to 4; and
m' is 0 or 1 when m is 1, and 1 when m is 2, 3 or 4.

(9) The precipitation promoter of the aforementioned (8), wherein $R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group or an optionally substituted monocyclic heterocyclic group.

(10) The precipitation promoter of any one of the aforementioned (5) to (9), wherein the $C_{3-14}$ hydrocarbon ring is selected from a benzene ring and a cyclohexane ring.

(11) The precipitation promoter of any one of the aforementioned (1) to (10), wherein the organic group is a group represented by the formula (III):

**L-Y—Z  (III)

wherein
** shows a bonding position to a group to be protected;
L is a single bond, or a group represented by the formula (a1) or (a1'):

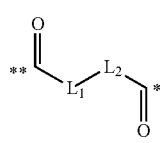

(a1)

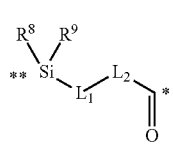

(a1')

wherein
* shows the bonding position to Y;
** is as defined above;
$R^8$ and $R^9$ are each independently a $C_{1-22}$ hydrocarbon group;
$L_1$ is a divalent $C_{1-22}$ hydrocarbon group; and
$L_2$ is a single bond, or a group represented by C(=O)N($R^{2'}$)—$R^{1'}$—N($R^3$)* wherein  shows the bonding position to $L_1$, * shows the bonding position to C=O, $R^{1'}$ is a $C_{1-22}$ alkylene group, and $R^{2'}$ and $R^3$ are each independently a hydrogen atom or a $C_{1-22}$ alkyl group, or $R^{2'}$ and $R^3$ are optionally joined to form a ring,
Y is a single bond, an oxygen atom or NR wherein R is a hydrogen atom, an alkyl group or an aralkyl group, and Z is a group represented by the formula (a2), the formula (a2') or the formula (a2"):

(a1)

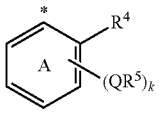

(a2')

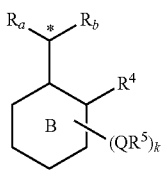

(a2")

wherein
* shows a bonding position;
R$^4$ is a hydrogen atom, or when R$_b$ is a group represented by the following formula (a3), optionally joined with R$^6$ of ring C to show a single bond or —O— and to form a fused ring together with ring A or ring B and ring C;
Q in the number of k are each independently —O—, —C(=O)—, —C(=O) O—, —OC(=O)—, —C(=O) NH— or —NHC(=O)—;
R$^5$ in the number of k are each independently a hydrocarbon group bonded via a single bond or a linker to an aliphatic hydrocarbon group having not less than 10 carbon atoms;
k is an integer of 1 to 4;
ring A and ring B are each independently optionally further have, in addition to QR$^5$ in the number of k, substituent(s) selected from the group consisting of a halogen atom, a C$_{1-6}$ alkyl group optionally substituted by a halogen atom, and a C$_{1-6}$ alkoxy group optionally substituted by a halogen atom;
R$_a$ is a hydrogen atom, or a phenyl group optionally substituted by a halogen atom; and
R$_b$ is a hydrogen atom, or a group represented by the formula (a3):

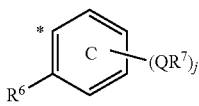

(a3)

wherein * shows a bonding position;
j is an integer of 0 to 4;
Q in the number of j are each independently as defined above;
R$^7$ in the number of j are each independently a hydrocarbon group bonded via a single bond or a linker to an aliphatic hydrocarbon group having not less than 10 carbon atoms;
R$^6$ is a hydrogen atom, or optionally joined with R$^4$ of ring A or ring B to show a single bond or —O— and to form a fused ring together with ring A or ring B and ring C; and
ring C optionally further has, in addition to OR$^7$ in the number of j, substituent(s) selected from the group consisting of a halogen atom, a C$_{1-6}$ alkyl group optionally substituted by a halogen atom, and a C$_{1-6}$ alkoxy group optionally substituted by a halogen atom, or
R$_a$ and R$_b$ are joined to form an oxo group.

(12) The precipitation promoter of the aforementioned (11), wherein Z is a group represented by the formula (a2) or the formula (a2'), the fused ring is a fluorene ring or a xanthene ring, R$^5$ in the number of k are each independently a hydrocarbon group bonded via a single bond or a linker to a linear aliphatic hydrocarbon group having not less than 10 carbon atoms, R$^7$ in the number of j are each independently a hydrocarbon group bonded via a single bond or a linker to a linear aliphatic hydrocarbon group having not less than 10 carbon atoms, and R$_a$ is a hydrogen atom, or R$_a$ and R$_b$ are joined to form an oxo group.

(13) The precipitation promoter of the aforementioned (11) or (12), wherein L is a group represented by the formula (a1), L$_1$ is a divalent C$_{1-22}$ hydrocarbon group, and L$_2$ is a single bond.

(14) The precipitation promoter of the aforementioned (11) or (12), wherein L is a group represented by the formula (a1'), L$_1$ is a phenylene group, and L$_2$ is a single bond.

(15) The precipitation promoter of any one of the aforementioned (11) to (14), wherein Y is an oxygen atom.

(16) The precipitation promoter of any one of the aforementioned (11) to (15), wherein Z is a group represented by the formula (a2), and R$^4$ is a hydrogen atom.

(17) The precipitation promoter of any one of the aforementioned (11) to (16), wherein Z is a group represented by the formula (a2), and R$_a$ and R$_b$ are each a hydrogen atom.

(18) The precipitation promoter of the aforementioned (11) or (12), wherein L and Y are each a single bond, Z is a group represented by the formula (a2), R$^4$ is a hydrogen atom, and R$_a$ and R$_b$ are joined to form an oxo group.

(19) The precipitation promoter of any one of the aforementioned (1) to (18), wherein the organic compound protected by the organic group is nucleoside, nucleotide or oligonucleotide optionally further protected by a protecting group used in nucleic acid synthesis, or amino acid or peptide optionally further protected by a protecting group used in peptide synthesis.

(20) The precipitation promoter of any one of the aforementioned (]) to (18), wherein the organic compound protected by the organic group is nucleoside, nucleotide or oligonucleotide optionally further protected by a protecting group used in nucleic acid synthesis.

(21) The precipitation promoter of any one of the aforementioned (1) to (18), wherein the organic compound protected by the organic group is nucleoside or oligonucleotide wherein at least one group selected from an amino group and an imino group of a nucleic acid base, 2'- and 3'-hydroxy groups of a ribose residue, and 3'-hydroxy group of a deoxyribose residue is protected by the organic group, and other group is optionally further protected by a protecting group used in nucleic acid synthesis.

(22) The precipitation promoter of any one of the aforementioned (1) to (21), wherein the solvent comprises a polar solvent.

(23) The precipitation promoter of the aforementioned (22), wherein the solvent comprising a polar solvent is a mixed solvent of a polar solvent and a nonpolar solvent.

(24) The precipitation promoter of the aforementioned (22) or (23), wherein the polar solvent is acetonitrile.

(25) The precipitation promoter of any one of the aforementioned (1) to (24), which is used at not less than 0.1 molar equivalent relative to the organic compound protected by the organic group to precipitate the organic compound protected by the organic group.

(26) A precipitation mixture comprising the precipitation promoter of any one of the aforementioned (1) to (25), and an organic compound protected by an organic group having one or more aliphatic hydrocarbon groups having not less than 10 carbon atoms.

(27) The precipitation mixture of the aforementioned (26), wherein the aliphatic hydrocarbon group having not less than 10 carbon atoms of the organic group is linear.

(28) A method of precipitating an organic compound protected by an organic group having one or more aliphatic hydrocarbon groups having not less than 10 carbon atoms in a solvent, by using the precipitation promoter of any one of the aforementioned (1) to (25).

(29) The method of the aforementioned (28), wherein the solvent comprises a polar solvent.

(30) The method of the aforementioned (29), wherein the polar solvent is acetonitrile.

(31) The method of any one of the aforementioned (28) to (30), wherein the aliphatic hydrocarbon group having not less than 10 carbon atoms of the organic group is linear

(32) A production method of an oligonucleotide, comprising a step of adding a polar solvent to a reaction solution comprising an oligonucleotide wherein at least one group is protected by an organic group having one or more aliphatic hydrocarbon groups having not less than 10 carbon atoms, and other group is optionally further protected by a protecting group used in nucleic acid synthesis, and the precipitation promoter of any one of the aforementioned (1) to (25) in a nonpolar solvent, and separating a precipitate mixture comprising the oligonucleotide and the precipitation promoter from the reaction solution.

(33) The production method of the aforementioned (32), wherein the polar solvent is acetonitrile.

(34) The production method of the aforementioned (32) or (33), wherein the aliphatic hydrocarbon group having not less than 10 carbon atoms of the organic group is linear.

(35) The production method of any one of the abovementioned (32) to (34), which is performed by a phosphoramidite method.

(36) A production method of an oligonucleotide, which includes one repeat of production cycle comprising the following steps (1)-(3), or plural repeats thereof by a phosphoramidite method, which comprises the following step (4) in the first cycle, the following step (5) in each cycle, and the following step (6) in each cycle except the final cycle:

(1) a step of obtaining a reaction solution comprising a free-5'-hydroxy-group form by adding an acid to a reaction solution comprising a nucleoside or oligonucleotide wherein at least one group selected from an amino group and an imino group of a nucleic acid base, 2'- and 3'-hydroxy groups of a ribose residue, and 3'-hydroxy group of a deoxyribose residue is protected by an organic group having one or more aliphatic hydrocarbon groups having not less than 10 carbon atoms, a 5'-hydroxy group is protected by a temporary protecting group removable under acidic conditions, and other group is optionally further protected by a protecting group used in nucleic acid synthesis in a nonpolar solvent, to deprotect the temporary protecting group of the 5'-hydroxy group, and neutralizing same with a base;

(2) a step of obtaining a reaction solution comprising a phosphite triester form, by adding nucleoside or oligonucleotide wherein a 3'-hydroxy group is phosphoramidited, a 5'-hydroxy group is protected by a temporary protecting group removable under acidic conditions, and other group is optionally further protected by a protecting group used in nucleic acid synthesis to the reaction solution comprising the free-5'-hydroxy-group form in a nonpolar solvent;

(3) a step of obtaining a reaction solution comprising an oligonucleotide wherein at least one group selected from an amino group and an imino group of a nucleic acid base, 2'- and 3'-hydroxy groups of a ribose residue, and 3'-hydroxy group of a deoxyribose residue is protected by an organic group having one or more aliphatic hydrocarbon groups having not less than 10 carbon atoms, a 5'-hydroxy group is protected by a temporary protecting group removable under acidic conditions, and other group is optionally further protected by a protecting group used in nucleic acid synthesis, by adding an oxidizing agent or a sulfurizing agent to the reaction solution comprising the phosphite triester form in a nonpolar solvent;

(4) a step of adding the precipitation promoter of any one of the aforementioned (1) to (25) to the reaction solution at any of before step (1), between steps (1) and (2), between steps (2) and (3) and after step (3);

(5) a step of separating a precipitation mixture comprising the free-5'-hydroxy-group form, the phosphite triester form or the oligonucleotide, and the precipitation promoter from the reaction solution by adding a polar solvent to the reaction solution comprising the precipitation promoter at after step (4), and any of between steps (1) and (2), between steps (2) and (3) and after step (3); and (6) a step of adding a nonpolar solvent to the precipitation mixture obtained in step (5) to give a reaction solution.

(37) The production method of the aforementioned (36), wherein the polar solvent is acetonitrile.

(38) The production method of the aforementioned (36) or [37], wherein the aliphatic hydrocarbon group having not less than 10 carbon atoms of the organic group is linear.

(39) The method of any one of the above-mentioned (36) to (38), wherein the steps (5) and (6) are performed after step (3).

(40) The method of any one of the above-mentioned (36) to (39), further comprising the following step (7):

(7) a step of removing all protecting groups of the oligonucleotide and isolating the oligonucleotide.

(41) The method of any one of the above-mentioned (36) to (40), wherein the non-polar solvent is a solvent selected from the group consisting of a halogenated solvent, an aromatic solvent, an ester solvent, an aliphatic solvent, and a combination thereof.

Effect of the Invention

By using the precipitation promoter of the present invention, the precipitation of an organic compound having a pseudo solid phase protecting group, which is a hydrophobic group, in a solvent can be promoted, and the recovery rate thereof can be improved.

DETAILED DESCRIPTION OF THE PREFERRED EMBODIMENTS

Terms

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" to be the constituent unit of oligonucleotide means a compound wherein a nucleic acid base is bonded to the 1'-position of a sugar (e.g., ribose or deoxyribose wherein the carbon atoms at 2-position and carbon atom at 4-position of 2-deoxyribose, ribose, ribose ring or deoxyribose ring are bonded by a divalent organic group, and the like) by N-glycosidation. Examples of the ribose or deoxyribose wherein the carbon atom at 2-position and carbon atom at 4-position of the ribose ring or deoxyribose ring are bonded by a divalent organic group include the following compounds.

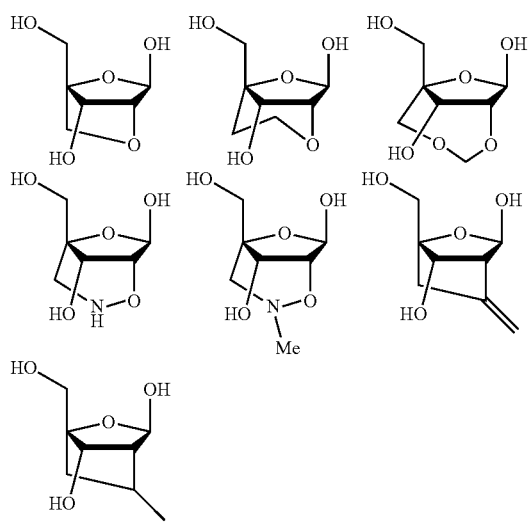

In the present specification, the "nucleotide" means a compound wherein a phosphoric acid group is bonded to a nucleoside.

In the present specification, the "oligonucleotide" means a compound wherein one or more nucleotides are bonded to a nucleoside. While the number of nucleosides in oligonucleotide in the present invention is not particularly limited, it is preferably 3 to 50, more preferably 5 to 30.

In the present specification, the "nucleoside" and "nucleotide" encompass morpholino nucleoside and morpholino nucleoside having a morpholine residue instead of a ribose residue or a deoxyribose residue.

In the present specification, the "morpholino nucleoside" is a compound represented by the following formula (1). In the present specification, morpholino nucleoside represented by the formula (1) is referred to as morpholino nucleoside (1). Compounds represented by other formulas may also be referred to in the same manner.

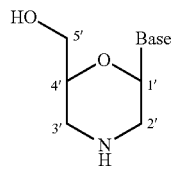

(1)

wherein Base is an optionally protected nucleic acid base.

Morpholino nucleoside (1) can be prepared by a method known per se (e.g., the method described in WO 91/09033A1, which is incorporated herein by reference in its enirety), or a method analogous thereto. Specifically, as shown in the following scheme, the corresponding ribonucleoside (2) is subjected to oxidative ring opening with sodium periodate etc. to give the corresponding 2',3'-dialdehyde (3), the dialdehyde (3) is subjected to ring closure with ammonia to give 2',3'-dihydroxymorpholino nucleoside (4), and dihydroxymorpholino nucleoside (4) is reduced with a reducing agent (e.g., sodium cyanoborohydride, sodium triacetoxyborohydride and the like), whereby morpholino nucleoside (1) can be obtained.

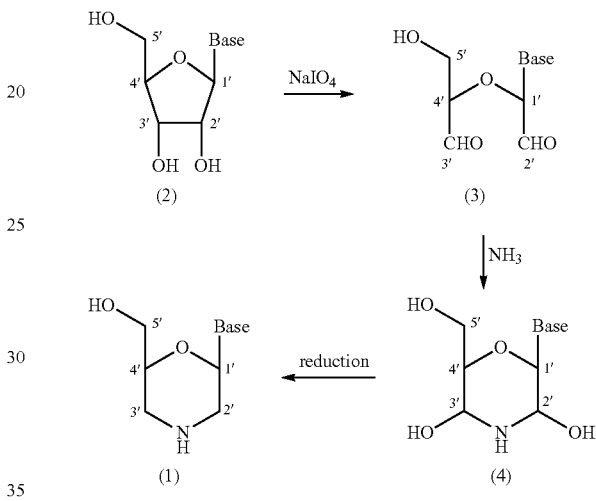

In the present specification, the position number (1', 2' and the like) of morpholino nucleoside corresponds to that of the carbon atom of ribose of ribonucleoside (2) as the material. In the present specification, according to the usual practice in the nucleic acid chemistry, morpholino nucleoside on the terminal of the side having a free 5'-hydroxy group of morpholino oligonucleotide is referred to as the "5'-terminus", and morpholino nucleoside on the terminal of the opposite side is referred to as the "3'-terminus".

In the present specification, the "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the 5'-position of nucleotide or deprotection conditions of the morpholine ring nitrogen atom of morpholino nucleotide is preferable. The "amino-protecting group" is not particularly limited, and examples thereof include the protecting groups described in Greene's PROTECTIVE GROUPS IN ORGANIC SYNTHESIS, 4th edition, Wiley-Interscience, 2006, which is incorporated herein by reference in its entirety, and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tertbutylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, examples of the "alkyl (group)" include a linear or branched chain alkyl group having one or more carbon atoms. When the carbon number is not particularly limited, it is preferably a $C_{1-10}$ alkyl group, more preferably a $C_{1-6}$ alkyl group. When the carbon number is not particularly limited, for example, methyl, ethyl, propyl, isopropyl, butyl, isobutyl, sec-butyl, tert-butyl, pentyl, hexyl and the like are preferable, and methyl and ethyl are particularly preferable.

In the present specification, "$C_{a-b}$" means that the carbon number is not less than a and not more than b (a, b each show an integer).

In the present specification, examples of the "aralkyl (group)" include a $C_{7-20}$ aralkyl group, preferably a $C_{7-16}$ aralkyl group (a $C_{6-10}$ aryl-$C_{1-6}$ alkyl group). Preferable specific examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, examples of the "alkoxy (group)" include an alkoxy group having one or more carbon atoms. When the carbon number is not particularly limited, it is preferably a $C_{1-10}$ alkoxy group, more preferably a $C_{1-6}$ alkoxy group. When the carbon number is not particularly limited, methoxy, ethoxy, propoxy, isopropoxy, butoxy, isobutoxy, sec-butoxy, tert-butoxy, pentyloxy, hexyloxy and the like are preferable, and methoxy and ethoxy are particularly preferable.

In the present specification, examples of the "acyl (group)" include a linear or branched chain $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, as the "alkenyl (group)", a linear or branched chain $C_{2-6}$ alkenyl group and the like are preferable. Preferable examples thereof include vinyl, 1-propenyl, allyl, isopropenyl, butenyl, isobutenyl and the like. Among them, a $C_{2-4}$ alkenyl group is preferable.

In the present specification, as the "alkynyl (group)", include a $C_{2-6}$ alkynyl group and the like are preferable. Preferable examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_{2-4}$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_{3-6}$ cycloalkyl group such as cyclopropyl, cyclobutyl, cyclopentyl, cyclohexyl and the like is preferable, and cyclohexyl is particularly preferable.

In the present specification, the "aryl (group)" means an aromatic monocyclic or polycyclic (fused) hydrocarbon group. Specific examples thereof include a $C_{6-14}$ aryl group such as phenyl, 1-naphthyl, 2-naphthyl, biphenylyl, 2-anthryl and the like, and the like. Among them, a $C_{6-10}$ aryl group is more preferably and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like. Specific examples thereof include a monovalent group such as an alkyl group, an alkenyl group, an alkynyl group, a cycloalkyl group, an aryl group, an aralkyl group and the like, and a divalent group derived therefrom.

In the present specification, the three alkyl groups in the "trialkylsilyl (group)" may be the same or different. The alkyl group may be any of independently linear and branched chain. As the "trialkylsilyl (group)", a tri($C_{1-6}$ alkyl)silyl group is preferable, for example, trimethylsilyl group, triethylsilyl group, triisopropylsilyl group, tert-butyldimethylsilyl group can be mentioned.

In the present specification, the "alkylene (group)" may be any of linear and branched chain. As the "alkylene (group)", an alkylene group having one or more carbon atoms can be mentioned. When the range of carbon number is not particularly limited, it is preferably a $C_{1-10}$ alkylene group, more preferably a $C_{1-6}$ alkylene group. Preferable specific examples include methylene, ethylene, propylene, butylene, pentylene and hexylene, particularly preferably methylene and ethylene.

In the present specification, examples of the "linker" include —O—, —C(=O)—, —C(=O)O—, —OC(=O)—, —C(=O)NH—, —NHC(=O)—, —S—, —SO—, —SO$_2$—, —Si(R)(R')O—, —Si(R)(R')— (R, R' are each independently a hydrogen atom or a $C_{1-22}$ hydrocarbon group) and the like.

In the present specification, the "substituent" of "optionally substituted" encompasses the aforementioned halogen atom, alkyl group, aralkyl group, alkoxy group, acyl group, alkenyl group, alkynyl group, cycloalkyl group, aryl group, as well as hydroxy group, nitro group, cyano group, guanidyl group, carboxy group, alkoxycarbonyl group (alkoxy moiety is the same as that in the aforementioned alkoxy group), sulfo group, phospho group, alkylthio group (alkyl moiety is the same as that in the aforementioned alkyl group), alkylsulfinyl group (alkyl moiety is the same as that in the aforementioned alkyl group), alkylsulfonyl group (alkyl moiety is the same as that in the aforementioned alkyl group), amino group, monoalkylamino group (alkyl moiety is the same as that in the aforementioned alkyl group), dialkylamino group (alkyl moiety is the same as that in the aforementioned alkyl group), oxo group, acylamino group (acyl moiety is the same as that in the aforementioned alkyl group) and the like.

In the present specification, examples of the "$C_{3-14}$ hydrocarbon ring" (including "$C_{3-14}$ hydrocarbon ring" of the "optionally substituted $C_{3-14}$ hydrocarbon ring") include $C_{3-10}$ cycloalkane, $C_{3-10}$ cycloalkene, $C_{6-14}$ aromatic hydrocarbon ring.

Examples of the "$C_{3-10}$ cycloalkane" include cyclopropane, cyclobutane, cyclopentane, cyclohexane, cycloheptane, cyclooctane.

Examples of the "$C_{3-10}$ cycloalkene" include cyclopropene, cyclobutene, cyclopentene, cyclohexene, cycloheptene, cyclooctene.

Examples of the "$C_{6-14}$ aromatic hydrocarbon ring" include benzene, naphthalene.

In the present specification, examples of the "monocyclic heterocyclic group" (including "monocyclic heterocyclic group" of the "optionally substituted monocyclic heterocyclic group") include monocyclic aromatic heterocyclic group and monocyclic nonaromatic heterocyclic group each containing, as a ring-constituting atom besides carbon atom, 1 to 4 hetero atoms selected from nitrogen atom, sulfur atom and oxygen atom.

Examples of the "monocyclic aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like.

Examples of the "monocyclic nonaromatic heterocyclic group" include 3- to 8-membered monocyclic nonaromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl (e.g., morpholin-4-yl), thiomorpholinyl, azepanyl, diazepanyl, azepinyl, oxepanyl, azocanyl, diazocanyl and the like.

Precipitation Promoter

The precipitation promoter of the present invention is an organic compound having one or more linear aliphatic hydrocarbon groups having not less than 10 carbon atoms wherein the aforementioned aliphatic hydrocarbon group has not less than 20 carbon atoms in total, which is used to precipitate an organic compound protected by an organic group having one or more aliphatic hydrocarbon groups having not less than 10 carbon atoms (hereinafter sometimes referred to as "the pseudo solid phase protecting group of the present invention") in a solvent. Only one kind of the precipitation promoter of the present invention may be used, or two or more kinds thereof may be used in combination.

The aforementioned solvent is preferably a solvent containing a polar solvent, more preferably a mixed solvent of a polar solvent and a nonpolar solvent. The aforementioned polar solvent is preferably acetonitrile.

The linear aliphatic hydrocarbon group having not less than 10 carbon atoms contained in the precipitation promoter of the present invention needs to have not less than 20, preferably 22 or more, carbon atoms in total. When the total carbon number is less than 20, the organic compound protected by a pseudo solid phase protecting group in the liquid phase cannot be precipitated sufficiently, and the recovery rate of the organic compound decreases. While the upper limit is not particularly limited, the total carbon number is preferably not more than 220, more preferably not more than 100, further preferably not more than 70.

The linear aliphatic hydrocarbon group having not less than 10 carbon atoms in the precipitation promoter of the present invention is preferably a group selected from a linear $C_{10-40}$ alkyl group and a linear $C_{10-40}$ alkenyl group, more preferably a linear $C_{10-40}$ alkyl group, further preferably a linear $C_{10-30}$ alkyl group, particularly preferably a linear $C_{12-28}$ alkyl group, most preferably a linear $C_{14-26}$ alkyl group. The number of a linear aliphatic hydrocarbon group having not less than 10 carbon atoms contained in the precipitation promoter of the present invention is preferably 1-12, more preferably 1-9.

One embodiment of the precipitation promoter of the present invention is an organic compound having one or more structures represented by the following formula (G):

(G)

wherein
each $R^1$ is independently a linear $C_{10-40}$ alkyl group;
each $X^1$ is independently a single bond, —O—, —C(=O)—, —C(=O)O—, —OC(=O)—, —C(=O)NH— or —NHC(=O)—;
ring $A^1$ is an optionally substituted $C_{3-14}$ hydrocarbon ring; and
n is an integer of 1 to 4.

In formula (G), the bonding direction of $X^1$ corresponds to the direction of the above-mentioned chemical formula. For example, when $X^1$ is —C(=O)O—, it is bonded to $R^1$ on the left side of —C(=O)O—, and bonded to $A^1$ on the right side of —C(=O)O—.

When the formula (G) contains a plurality of $R^1$, they may be the same or different. The same applied to $X^1$.

A preferable one embodiment of the precipitation promoter of the present invention is a compound represented by the following formula (I). The "compound represented by the formula (I)" is sometimes abbreviated as "compound (I)". Compounds represented by other formulas may also be abbreviated similarly.

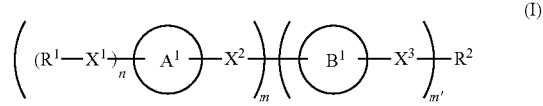

(I)

wherein
each $R^1$ is independently a linear $C_{10-40}$ alkyl group;

each $X^1$ is independently a single bond, —O—, —C(=O)—, —C(=O)O—, —C(=O)NH— or —NHC(=O)—;

ring $A^1$ and ring $B^1$ are each independently an optionally substituted $C_{3-14}$ hydrocarbon ring;

each $X^2$ is independently —$(CH_2)_p$—, —$(CH_2)_p$—O—$(CH_2)_q$—, —$(CH_2)_p$—C(=O)—, —$(CH_2)_q$—, —$(CH_2)_p$—C(=O)O—$(CH_2)_q$—, —$(CH_2)_p$—OC(=O)—$(CH_2)_q$—, —$(CH_2)_p$—C(=O)NH—$(CH_2)_q$— or —$(CH_2)_p$—NHC(=O)—$(CH_2)_q$— (p and q are each independently an integer of 0-3);

$X^3$ is a single bond, —$(CH_2)_r$—O—, —$(CH_2)_r$—C(=O)—, —$(CH_2)_r$—C(=O)O—, —$(CH_2)_r$—OC(=O)—, —$(CH_2)_r$—C(=O)NH— or —$(CH_2)_r$—NHC(=O)— (r is an integer of 0-3);

$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted monocyclic heterocyclic group or a tri($C_{1-6}$ alkyl)silyl group (preferably hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group or an optionally substituted monocyclic heterocyclic group);

n and m are each independently an integer of 1 to 4;

m' is 0 or 1 when m is 1, and 1 when m is 2, 3 or 4.

In formula (I), the bonding directions of $X^1$, $X^2$ and $X^3$ each correspond to the direction of the above-mentioned chemical formula. For example, when $X^3$ is —$(CH_2)_r$—O—, it is bonded to ring $B^1$ on the left side of —$(CH_2)_r$—O—, and bonded to $R^2$ on the right side of —$(CH_2)_r$—O—.

When formula (I) contains a plurality of $R^1$, they may be the same or different. The same applied to $X^1$, ring $A^1$, and $X^2$.

A more preferable one embodiment of the precipitation promoter of the present invention is a compound represented by the following formula (II).

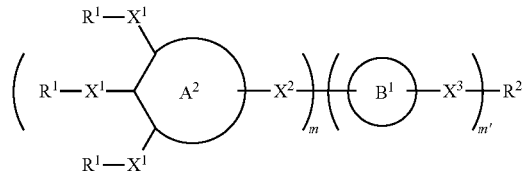

(II)

wherein each $R^1$ is independently a linear $C_{10-40}$ alkyl group;

each $X^1$ is independently a single bond, —O—, —C(=O)—, —C(=O)O—, —OC(=O)—, —C(=O)NH— or —NHC(=O)—;

ring $A^2$ and ring $B^1$ are each independently an optionally substituted $C_{3-14}$ hydrocarbon ring;

each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$—, —$(CH_2)_p$—OC(=O)—$(CH_2)_q$—, —$(CH_2)_p$—C(=O) NH—$(CH_2)_q$— or —$(CH_2)_p$—NHC(=O)—$(CH_2)_q$— (p and q are each independently an integer of 0 to 3);

$X^3$ is a single bond, —$(CH_2)_r$—O—, —$(CH_2)_r$—C(=O)—, —$(CH_2)_r$—C(=O)O—, —$(CH_2)_r$—OC(=O)—, —$(CH_2)_r$—C(=O)NH— or —$(CH_2)_r$—NHC(=O)— (r is an integer of 0 to 3);

$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-19}$ aryl group, an optionally substituted monocyclic heterocyclic group or a tri($C_{1-6}$ alkyl)silyl group (preferably hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group or an optionally substituted monocyclic heterocyclic group);

m is an integer of 1 to 4; and m' is 0 or 1 when m is 1, and 1 when m is 2, 3 or 4.

In formula (II), the bonding directions of $X^1$, $X^2$ and $X^3$ each correspond to the direction of the above-mentioned chemical formula. For example, when $X^3$ is —$(CH_2)_r$—O—, it is bonded to ring $B^1$ on the left side of —$(CH_2)_r$—O—, and bonded to $R^2$ on the right side of —$(CH_2)_r$—O—.

When formula (II) contains a plurality of $R^1$, they may be the same or different. The same applied to $X^1$. When the formula (II) contains a plurality of ring $A^2$, they may be the same or different. The same applied to $X^2$.

When $R^1$ is present in plurality, they may be the same or different. Each $R^1$ is independently preferably a linear $C_{10-30}$ alkyl group, more preferably a linear $C_{12-28}$ alkyl group, further preferably a linear $C_{14-26}$ alkyl group.

In one embodiment of the present invention, $R^2$ is preferably a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group or an optionally substituted monocyclic heterocyclic group, more preferably a hydrogen atom, an optionally substituted $C_{1-6}$ alkyl group, an optionally substituted $C_{2-6}$ alkenyl group, an optionally substituted $C_{2-6}$ alkynyl group or an optionally substituted $C_{6-14}$ aryl group, further preferably a hydrogen atom or an optionally substituted $C_{1-6}$ alkyl group, particularly preferably a hydrogen atom or a $C_{1-6}$ alkyl group.

In another embodiment of the present invention, $R^2$ is preferably a hydrogen atom, an optionally substituted $C_{1-6}$ alkyl group, an optionally substituted $C_{2-6}$ alkenyl group, an optionally substituted $C_{2-6}$ alkynyl group or an optionally substituted $C_{6-14}$ aryl group, an optionally substituted 3-8-membered monocyclic nonaromatic heterocyclic group or a tri($C_{1-6}$ alkyl)silyl group, more preferably hydrogen atom or an optionally substituted $C_{1-6}$ alkyl group or a 3- to 8-membered monocyclic nonaromatic heterocyclic group or a tri($C_{1-6}$ alkyl)silyl group, further preferably a hydrogen atom, a $C_{1-6}$ alkyl group optionally substituted by a $C_{1-6}$ alkanoylamino group (e.g., acetylamino group) or a 3- to 8-membered monocyclic nonaromatic heterocyclic group (e.g., morpholin-4-yl group) or a tri($C_{1-6}$ alkyl)silyl group (e.g. triisopropylsilyl group).

Each $X^1$ is independently preferably a single bond, —O—, —C(=O)—, —C(=O)O— or —OC(=O)—, more preferably —O—, —C(=O)O— or —OC(=O)—, further preferably —O—.

Each $X^2$ is independently preferably —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$— or —$(CH_2)_p$—OC(=O)—$(CH_2)_q$— (p and q are each independently an integer of 0 to 3), more preferably —$(CH_2)_p$—$(CH_2)$—O—$(CH_2)_q$—, —$(CH_2)_p$—C(=O)—$(CH_2)_q$—, —$(CH_2)_p$—C(=O)O—$(CH_2)_q$— or —$(CH_2)_p$—OC(=O)—$(CH_2)_q$— (p and q are each independently an integer of 0 to 3), further preferably a single bond, —$(CH_2)_p$—O—$(CH_2)_q$—, —C(=O)—, —C(=O)O—$(CH_2)_q$— or —$(CH_2)_p$—OC(=O)— (p and q are each independently an integer of 0 or 1).

$X^3$ is preferably a single bond, —$(CH_2)_r$—O—$(CH_2)_r$—C(=O)—, —$(CH_2)_r$—C(=O)O— or —$(CH_2)_r$—OC(=O)— (r is an integer of 0 to 3), more preferably a single bond, —$(CH_2)_r$—C(=O)—$(CH_2)_r$—C(=O)O— or —$(CH_2)_r$—OC(=O)— (r is an integer of 0 to 3), further preferably a single bond, —C(=O)—C(=O)O— or —OC(=O)—.

n is preferably an integer of 1 to 3.

m is preferably an integer of 1 to 3, more preferably 1 or 3.

The $C_{3-14}$ hydrocarbon ring is preferably selected from a benzene ring and a cyclohexane ring, more preferably a benzene ring.

A preferable compound (I) is a compound wherein
each $R^1$ is independently a linear $C_{10-30}$ alkyl group;
each $X^1$ is independently a single bond, —O—, —C(=O)—, —C(=O)O— or —OC(=O)—;
ring $A^2$ and ring $B^1$ are each independently a benzene ring or a cyclohexane ring;
each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$— or —$(CH_2)_p$—OC(=O)—$(CH_2)_q$— (p and q are each independently an integer of 0 to 3);
$X^3$ is a single bond, —$(CH_2)_r$—O—, —$(CH_2)_r$—C(=O)—, —$(CH_2)_r$—C(=O)O— or —$(CH_2)_r$—OC(=O)— (r is an integer of 0 to 3);
$R^2$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted 3-8-membered monocyclic nonaromatic heterocyclic group or a tri($C_{1-6}$ alkyl)silyl group;
n is an integer of 1 to 3;
m is an integer of 1 to 3; and
m' is 0 or 1 when m is 1, and 1 when m is 2 or 3.

In this embodiment, $R^2$ is more preferably a hydrogen atom, an optionally substituted $C_{1-6}$ alkyl group, an optionally substituted $C_{2-6}$ alkenyl group, an optionally substituted $C_{2-6}$ alkynyl group or an optionally substituted $C_{6-19}$ aryl group.

A more preferable compound (I) is a compound wherein
each $R^1$ is independently a linear $C_{12-28}$ alkyl group;
each $X^1$ is independently —O—, —C(=O)O— or —OC(=O)—;
ring $A^2$ and ring $B^1$ are each independently a benzene ring or a cyclohexane ring;
each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$— or —$(CH_2)_p$—OC(=O)—$(CH_2)_q$— (p and q are each independently an integer of 0 to 3);
$X^3$ is a single bond, —$(CH_2)_r$—C(=O)—, —$(CH_2)_r$—C(=O)O— or —$(CH_2)_r$—OC(=O)— (r is an integer of 0 to 3);
$R^2$ is a hydrogen atom, an optionally substituted $C_{1-6}$ alkyl group or a 3- to 8-membered monocyclic nonaromatic heterocyclic group or a tri($C_{1-6}$ alkyl)silyl group;
n is an integer of 1 to 3;
m is an integer of 1 to 3; and
m' is 0 or 1 when m is 1, and 1 when m is 2 or 3.

In this embodiment, it is more preferable that $R^2$ is a hydrogen atom or an optionally substituted $C_{1-6}$ alkyl group.

A still more preferable compound (I) is a compound wherein
each $R^1$ is independently a linear $C_{12-28}$ alkyl group;
each $X^1$ is independently —O—, —C(=O)O— or —OC(=O)—;
ring $A^2$ and ring $B^1$ are each independently a benzene ring or a cyclohexane ring;
each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$— or —$(CH_2)_p$—OC(=O)—$(CH_2)_q$— (p and q are each independently an integer of 0 to 3);
$X^3$ is a single bond, —$(CH_2)_r$—C(=O)—, —$(CH_2)_r$—C(=O)O— or —$(CH_2)_r$—OC(=O)— (r is an integer of 0 to 3);
$R^2$ is a hydrogen atom, a $C_{1-6}$ alkyl group optionally substituted by a $C_{1-6}$ alkanoylamino group (e.g., acetylamino group) or a 3- to 8-membered monocyclic nonaromatic heterocyclic group (e.g., morpholin-4-yl group) or a tri($C_{1-6}$ alkyl)silyl group (e.g., triisopropylsilyl group);
n is an integer of 1 to 3;
m is an integer of 1 to 3; and
m' is 0 or 1 when m is 1, and 1 when m is 2 or 3.

A further preferable compound (I) is a compound wherein
each $R^1$ is independently a linear $C_{14-26}$ alkyl group;
$X^1$ is —O—;
ring $A^2$ and ring $B^1$ are each independently a benzene ring or a cyclohexane ring;
each $X^2$ is independently a single bond, —$(CH_2)_p$—O—$(CH_2)_q$—, —C(=O)—, —C(=O)O—$(CH_2)_q$— or —$(CH_2)_p$—OC(=O)— (p and q are each independently an integer of 0 or 1);
$X^3$ is a single bond, —C(=O)—, —C(=O)O— or —OC(=O)—;
$R^2$ is a hydrogen atom, a $C_{1-6}$ alkyl group optionally substituted by a $C_{1-6}$ alkanoylamino group (e.g., acetylamino group) or a 3- to 8-membered monocyclic nonaromatic heterocyclic group (e.g., morpholin-4-yl group) or a tri($C_{1-6}$ alkyl)silyl group (e.g., triisopropylsilyl group);
n is an integer of 1 to 3;
m is 1 or 3; and
m' is 0 or 1 when m is 1, and 1 when m is 3.

In the aforementioned further preferable compound (I), $R^2$ is more preferably a hydrogen atom or a $C_{1-6}$ alkyl group.

In the aforementioned further preferable compound (I), it is more preferable that when m is 1 and m' is 0, each $X^2$ is independently a single bond, —C(=O)O—$(CH_2)_q$— or —$(CH_2)_p$—OC(=O)-(p and q are each independently an integer of 0 or 1), $R^2$ is a $C_{1-6}$ alkyl group.

In the aforementioned further preferable compound (I), it is more preferable that when m is 1 or 3 and m' is 1, each $X^2$ is independently —$(CH_2)_p$—O—$(CH_2)_q$— or —C(=O)— (p and q are each independently an integer of 0 or 1), $X^3$ is a single bond or —C(=O)O—, and $R^2$ is a hydrogen atom or a $C_{1-6}$ alkyl group.

A particularly preferable compound (I) is a compound wherein
each $R^1$ is independently a linear $C_{14-26}$ alkyl group;
$X^1$ is —O—;
ring $A^2$ and ring $B^1$ are each a benzene ring;
each $X^2$ is independently a single bond, —$(CH_2)_p$—O—$(CH_2)_q$—, —C(=O)—, —C(=O)O—$(CH_2)_q$— or —$(CH_2)_p$—OC(=O)— (p and q are each independently an integer of 0 or 1);
$X^3$ is a single bond, —C(=O)—, —C(=O)O— or —OC(=O)—;
$R^2$ is a hydrogen atom or a $C_{1-6}$ alkyl group;
n is an integer of 1 to 3;
m is 1 or 3; and
m' is 0 or 1 when m is 1, and 1 when m is 3.

In the aforementioned particularly preferable compound (I), when m is 1 and m' is 0, it is more preferable that $X^2$ is a single bond, —C(=O)O—(CH$_2$)$_q$— or —(CH$_2$)$_p$—OC(=O)— (p and q are each independently an integer of 0 or 1), and $R^2$ is a $C_{1-6}$ alkyl group.

In the aforementioned particularly preferable compound (I), when m is 1 or 3 and m' is 1, it is more preferable that $X^2$ is —(CH$_2$)$_p$—O—(CH$_2$)$_q$— or —C(=O)— (p and q are each independently an integer of 0 or 1), and $X^3$ is a single bond or —C(=O)O—.

A preferable compound (II) is a compound wherein
each $R^1$ is independently a linear $C_{10-30}$ alkyl group;
each $X^1$ is independently a single bond, —O—, —C(=O)—, —C(=O)O— or —OC(=O)—;
ring $A^2$ and ring $B^1$ are each independently a benzene ring or a cyclohexane ring;
each $X^2$ is independently —(CH$_2$)$_p$—, —(CH$_2$)$_p$—O—(CH$_2$)$_q$—, —(CH$_2$)$_p$—C(=O)—(CH$_2$)$_q$—, —(CH$_2$)$_p$—C(=O)O—(CH$_2$)$_q$— or —(CH$_2$)$_p$—OC(=O)—(CH$_2$)$_q$— (p and q are each independently an integer of 0 to 3);
$X^3$ is a single bond, —(CH$_2$)$_r$—O—, —(CH$_2$)$_r$—C(=O)—, —(CH$_2$)$_r$—C(=O)O— or —(CH$_2$)$_r$—OC(=O)— (r is an integer of 0-3);
$R^2$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted 3-8-membered monocyclic nonaromatic heterocyclic group or a tri($C_{1-6}$ alkyl)silyl group;
m is an integer of 1 to 3; and
m' is 0 or 1 when m is 1, and 1 when m is 2 or 3.

In this embodiment, it is more preferable that $R^2$ is a hydrogen atom, an optionally substituted $C_{1-6}$ alkyl group, an optionally substituted $C_{2-6}$ alkenyl group, an optionally substituted $C_{2-6}$ alkynyl group or an optionally substituted $C_{6-14}$ aryl group.

A more preferable compound (II) is a compound wherein
each $R^1$ is independently a linear $C_{12-28}$ alkyl group;
each $X^1$ is independently —O—, —C(=O)O— or —OC(=O)—;
ring $A^2$ and ring $B^1$ are each independently a benzene ring or a cyclohexane ring;
each $X^2$ is independently —(CH$_2$)$_p$—, —(CH$_2$)$_p$—O—(CH$_2$)$_q$—, —(CH$_2$)$_p$—C(=O)—(CH$_2$)$_q$—, —(CH$_2$)$_p$—C(=O)O—(CH$_2$)$_q$— or —(CH$_2$)$_p$—OC(=O)—(CH$_2$) (p and q are each independently an integer of 0 to 3);
$X^3$ is a single bond, —(CH$_2$)$_r$—C(=O)—, —(CH$_2$)$_r$—C(=O)O— or —(CH$_2$)$_r$—OC(=O)— (r is an integer of 0-3);
$R^2$ is a hydrogen atom, an optionally substituted $C_{1-6}$ alkyl group or a 3- to 8-membered monocyclic nonaromatic heterocyclic group or a tri($C_{1-6}$ alkyl)silyl group;
m is an integer of 1 to 3; and
m' is 0 or 1 when m is 1, and 1 when m is 2 or 3.

In this embodiment, it is more preferable that $R^2$ is a hydrogen atom or an optionally substituted $C_{1-6}$ alkyl group.

A still more preferable compound (II) is a compound wherein
each $R^1$ is independently a linear $C_{12-28}$ alkyl group;
each $X^1$ is independently —O—, —C(=O)O— or —OC(=O)—;
ring $A^2$ and ring $B^1$ are each independently a benzene ring or a cyclohexane ring;
each $X^2$ is independently —(CH$_2$)$_p$—, —(CH$_2$)$_p$—O—(CH$_2$)$_q$—, —(CH$_2$)$_p$—C(=O)—(CH$_2$)$_q$—, —(CH$_2$)$_p$—C(=O)O—(CH$_2$)$_q$— or —(CH$_2$)$_p$—OC(=O)—(CH$_2$) (p and q are each independently an integer of 0 to 3);

$X^3$ is a single bond, —(CH$_2$)$_r$—C(=O)—, —(CH$_2$)$_r$—C(=O)O— or —(CH$_2$)$_r$—OC(=O)— (r is an integer of 0 to 3);
$R^2$ is a hydrogen atom, a $C_{1-6}$ alkyl group optionally substituted by a $C_{1-6}$ alkanoylamino group (e.g., acetylamino group) or a 3- to 8-membered monocyclic nonaromatic heterocyclic group (e.g., morpholin-4-yl group) or a tri($C_{1-6}$ alkyl)silyl group (e.g., triisopropylsilyl group);
m is an integer of 1 to 3; and
m' is 0 or 1 when m is 1, and 1 when m is 2 or 3.

A further preferable compound (II) is a compound wherein
each $R^1$ is independently a linear $C_{14-26}$ alkyl group;
$X^1$ is —O—;
ring $A^2$ and ring $B^1$ are each a benzene ring or a cyclohexane ring;
each $X^2$ is independently a single bond, —(CH$_2$)$_p$—O—(CH$_2$)$_q$—, —C(=O)—, —C(=O)O—(CH$_2$)$_q$— or —(CH$_2$)$_p$—OC(=O)— (p and q are each independently an integer of 0 or 1);
$X^3$ is a single bond, —C(=O)—, —C(=O)O— or —OC(=O)—;
$R^2$ is a hydrogen atom, a $C_{1-6}$ alkyl group optionally substituted by a $C_{1-6}$ alkanoylamino group (e.g., acetylamino group) or a 3-8-membered monocyclic nonaromatic heterocyclic group (e.g., morpholin-4-yl group) or a tri($C_{1-6}$ alkyl)silyl group (e.g., triisopropylsilyl group);
m is 1 or 3; and
m' is 0 or 1 when m is 1, and 1 when m is 3.

In the aforementioned further preferable compound (II), it is more preferable that $R^2$ is a hydrogen atom or a $C_{1-6}$ alkyl group.

In the aforementioned further preferable compound (II), it is more preferable that when m is 1 and m' is 0, each $X^2$ is independently a single bond, —C(=O)O—(CH$_2$)$_q$— or —(CH$_2$)$_p$—OC(=O)-(p and q are each independently an integer of 0 or 1), and $R^2$ is a $C_{1-6}$ alkyl group.

In the aforementioned further preferable compound (II), it is more preferable that when m is 1 or 3 and m' is 1, each $X^2$ is independently —(CH$_2$)$_p$—O—(CH$_2$)$_q$— or —C(=O)— (p and q are each independently an integer of 0 or 1), $X^3$ is a single bond or —C(=O)O—, and $R^2$ is a hydrogen atom or a $C_{1-6}$ alkyl group.

A particularly preferable compound (II) is a compound wherein
each $R^1$ is independently a linear $C_{14-26}$ alkyl group;
$X^1$ is —O—;
ring $A^2$ and ring $B^1$ are each a benzene ring;
each $X^2$ is independently a single bond, —(CH$_2$)$_p$—O—(CH$_2$)$_q$—, —C(=O)—, —C(=O)O—(CH$_2$)$_q$— or —(CH$_2$)$_p$—OC(=O)— (p and q are each independently an integer of 0 or 1);
$X^3$ is a single bond, —C(=O)—, —C(=O)O— or —OC(=O)—;
$R^2$ is a hydrogen atom or a 01-6 alkyl group;
m is 1 or 3; and
m' is 0 or 1 when m is 1, and 1 when m is 3.

In the aforementioned particularly preferable compound (II), it is more preferable that when m is 1 and m' is 0, $X^2$ is a single bond, —C(=O)O—(CH$_2$)$_q$— or —(CH$_2$)$_p$—OC(=O)— (p and q are each independently an integer of 0 or 1), and $R^2$ is a $C_{1-6}$ alkyl group.

In the aforementioned particularly preferable compound (II), it is more preferable that when m is 1 or 3 and m' is 1, $X^2$ is —$(CH_2)_p$—O—$(CH_2)_q$— or —C(=O)— (p and q are each independently an integer of 0 or 1), and $X^3$ is a single bond or —C(=O)O—.

Specific examples encompassed in the aforementioned compound (I) include compounds represented by the following formulas (IV-a) to (IV-n). Among the specific examples, compound (IV-a) to compound (IV-l) are preferable, compound (IV-a) to compound (IV-j) are more preferable, compound (IV-a) to compound (IV-g) are further preferable, compound (IV-a) to compound (IV-e) are particularly preferable, and compound (IV-a) and compound (IV-b) are most preferable.

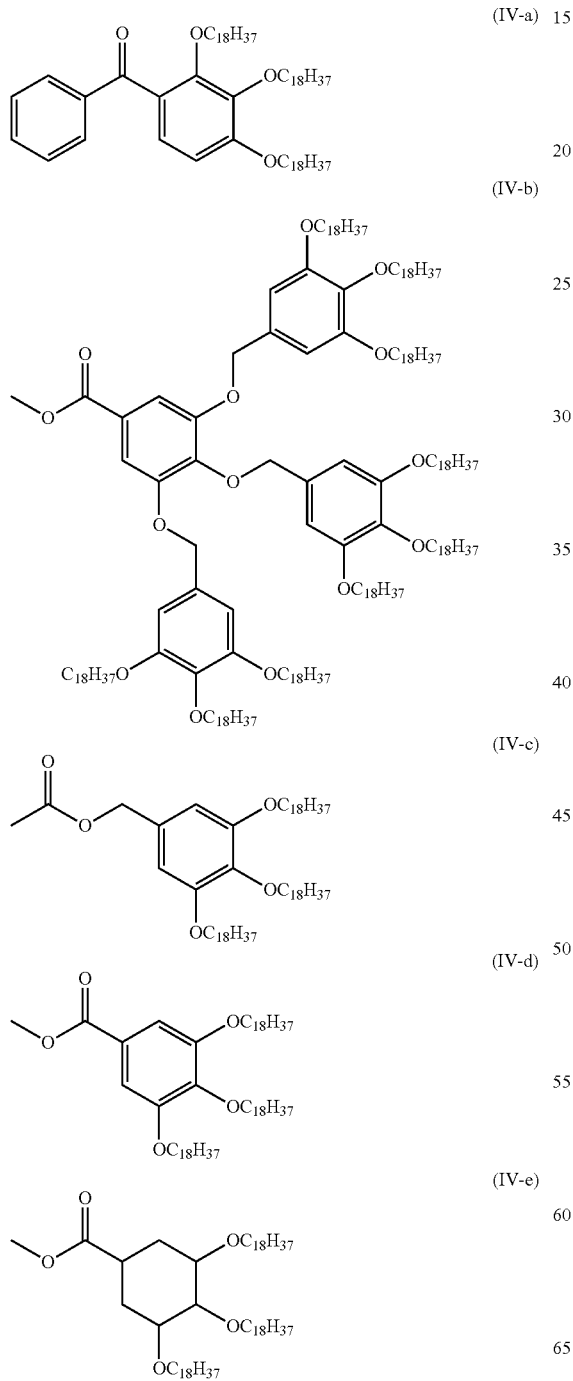

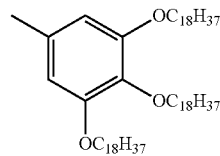

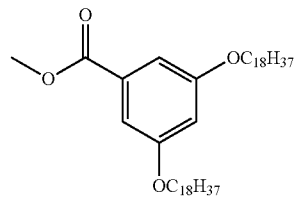

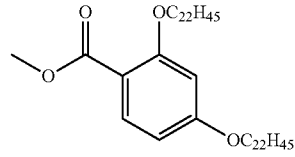

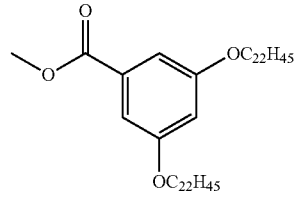

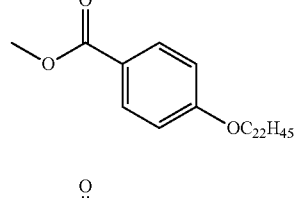

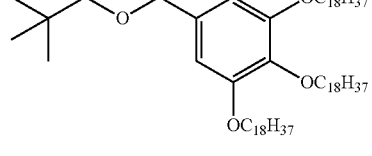

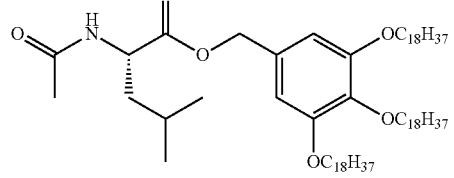

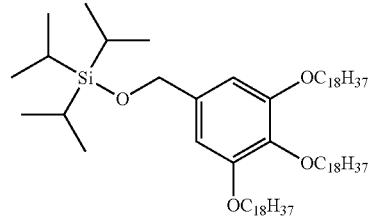

-continued (IV-n)

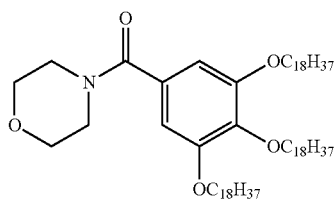

Another embodiment of the precipitation promoter of the present invention is optionally substituted $C_{1-10}$ alkane having one or more linear $C_{10-40}$ alkyl groups via a group selected from the group consisting of —O—, —C(=O)—, —C(=O)O—, —OC(=O)—, —C(=O)NH— and —NHC(=O)— (hereinafter sometimes to be referred to as "alkane compound").

$C_{1-10}$ alkane may be linear or branched chain. The carbon number of $C_{1-10}$ alkane is preferably 1 to 8, more preferably 2 to 6, further preferably 3 to 6.

The linear $C_{10-40}$ alkyl group of the alkane compound is preferably a linear $C_{10-30}$ alkyl group, more preferably a linear $C_{12-28}$ alkyl group, further preferably a linear $C_{14-26}$ alkyl group. The number of the linear $C_{10-40}$ alkyl groups of the alkane compound is preferably 2 to 6, more preferably 2 to 4, further preferably 3 or 4.

The group bonding the linear $C_{10-40}$ alkyl group and $C_{1-10}$ alkane is preferably a group selected from the group consisting of —O—, —C(=O)—, —C(=O)O— and —OC(=O)—, more preferably —O—.

A preferable alkane compound is optionally substituted $C_{1-8}$ alkane having 2 to 6 linear $C_{10-30}$ alkyl groups via a group selected from the group consisting of —O—, —C(=O)—, —C(=O)O— and —OC(=O)—. A more preferable alkane compound is optionally substituted $C_{2-6}$ alkane having 2 to 4 linear $C_{10-30}$ alkyl groups via —O—. A further preferable alkane compound is optionally substituted $C_{3-6}$ alkane having 3 or 4 linear $C_{14-26}$ alkyl groups via —O—.

Specific examples of the alkane compound include compounds represented by the following formulas (V-a) and (V-b):

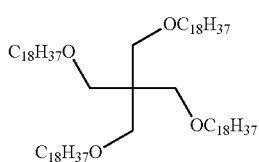
(V-a)

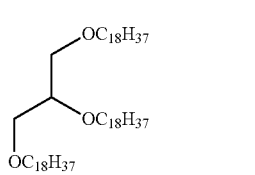
(V-b)

Production Method of Precipitation Promoter of the Present Invention

For example, compound (I) wherein $X^1$ is —O—, m is 1, and m' is 0 can be produced by alkylation of a hydroxy group of compound (IA-2) by using compound (IA-1) having a halogen atom ($X^a$), as in the following formula. Alkylation is well known in the field of organic synthesis, and those of ordinary skill in the art can perform alkylation by appropriately setting the conditions therefor.

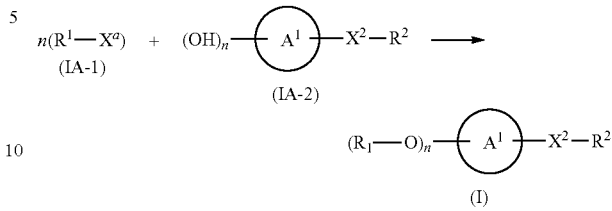

wherein $X^a$ is a halogen atom (preferably chlorine atom or bromine atom), and other symbols are as defined above.

For example, compound (I) wherein $X^2$ is —CH$_2$—O—, and m' is 1 can be produced by alkylation of a hydroxy group of compound (IB) by using compound (IA-3) having a halogen atom ($X^a$), as in the following formula.

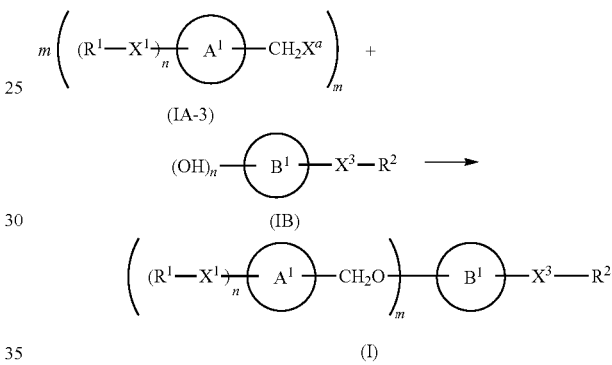

wherein each symbol is as defined above.

Other precipitation promoter of the present invention can also be produced according to a method known per se (e.g., alkylation, esterification, amidation etc.) or a method analogous thereto from a starting compound. As the starting compound, a commercially available product may be used, or a compound produced according to a method known per se or a method analogous thereto may be used.

Pseudo Solid Phase Protecting Group of the Present Invention

The precipitation promoter of the present invention is used to precipitate an organic compound protected by an organic group having one or more aliphatic hydrocarbon groups having not less than 10 carbon atoms (namely, the pseudo solid phase protecting group of the present invention) from a solvent containing the compound. Specific examples of the pseudo solid phase protecting group of the present invention and an organic compound protected by the pseudo solid phase protecting group include nucleoside, nucleotide and the like disclosed in WO 2012/157723, WO 2012/157723, WO 2014/189142, JP-A-2010-116418, all of which are incorporated herein by reference in their entireties, and the like, and amino acid, peptide and the like disclosed in WO 2010/104169, WO 2010/113939, WO 2011/078295, WO 2012/029794, JP-A-2009-185063, JP-A-2010-275254, all of which are incorporated herein by reference in their entireties, and the like. The pseudo solid phase protecting group of the present invention is preferably an organic group not removed under acidic conditions but removed under basic conditions.

One embodiment of the pseudo solid phase protecting group of the present invention is, for example, an organic group having a C$_{6-14}$ aromatic hydrocarbon ring, which is bonded via a linker to a hydrocarbon group bonded via a single bond or a linker to an aliphatic hydrocarbon group having not less than 10 carbon atoms. As the aforementioned hydrocarbon group, those mentioned above can be recited, and an aliphatic hydrocarbon group, an araliphatic hydrocarbon group (e.g., benzyl group) and a group (e.g., cyclohexylmethyl group) wherein a monocyclic saturated hydrocarbon group is bonded to an aliphatic hydrocarbon group are preferable. The "hydrocarbon group bonded via a single bond or a linker to an aliphatic hydrocarbon group having not less than 10 carbon atoms" also includes "an aliphatic hydrocarbon group having not less than 10 carbon atoms" itself (i.e., "aliphatic hydrocarbon group bonded via a single bond to aliphatic hydrocarbon group").

While the aliphatic hydrocarbon group having not less than 10 carbon atoms in the pseudo solid phase protecting group of the present invention may be linear or branched chain, it is preferably linear to sufficiently exhibit the effect of the precipitation promoter of the present invention. The aliphatic hydrocarbon group having not less than 10 carbon atoms is more preferably a group selected from a linear C$_{10-40}$ alkyl group and a linear C$_{10-40}$ alkenyl group, still more preferably a linear C$_{10-40}$ alkyl group, further preferably a linear C$_{10-30}$ alkyl group, particularly preferably a linear C$_{12-28}$ alkyl group, and most preferably a linear C$_{14-26}$ alkyl group.

The aforementioned linker is preferably selected from —O—, —C(=O)—, —C(=O)O—, —OC(=O)—, —C(=O)NH—, —NHC(=O)—, —S—, —SO—, —SO$_2$—, —Si(R)(R')O—, —Si(R)(R')— (R, R' are each independently a hydrogen atom or a C$_{1-22}$ hydrocarbon group), more preferably selected from —O—, —C(=O)—, —C(=O)O—, —OC(=O)—, —C(=O)NH— and —NHC(=O)—, and more preferably —O—.

The aforementioned C$_{6-14}$ aromatic hydrocarbon ring is preferably selected from a benzene ring and a naphthalene ring, and more preferably a benzene ring.

The aforementioned "C$_{6-14}$ aromatic hydrocarbon ring, which is bonded via a linker to a hydrocarbon group bonded via a single bond or a linker to an aliphatic hydrocarbon group having not less than 10 carbon atoms" is preferably a "C$_{6-14}$ aromatic hydrocarbon ring, which is bonded via a linker to a linear aliphatic hydrocarbon group having not less than 10 carbon atoms", more preferably a "C$_{6-14}$ aromatic hydrocarbon ring, which is bonded via a linker to a group selected from a linear C$_{10-40}$ alkyl group and a linear C$_{10-40}$ alkenyl group", still more preferably a "C$_{6-14}$ aromatic hydrocarbon ring, which is bonded via a linker to a linear C$_{10-40}$ alkyl group", further preferably a "C$_{6-14}$ aromatic hydrocarbon ring, which is bonded via a linker to a linear C$_{10-30}$ alkyl group", particularly preferably a "C$_{6-14}$ aromatic hydrocarbon ring, which is bonded via a linker to a linear C$_{12-28}$ alkyl group", and most preferably a "C$_{6-14}$ aromatic hydrocarbon ring, which is bonded via a linker to a linear C$_{14-26}$ alkyl group". In these groups, the linker is preferably —O—. In these groups, the C$_{6-14}$ aromatic hydrocarbon ring is preferably a benzene ring.

The aforementioned pseudo solid phase protecting group is preferably an "organic group having a benzene ring, which is bonded via —O— to a hydrocarbon group bonded via a single bond or —O— to a linear C$_{10-40}$ alkyl group", more preferably an "organic group having a benzene ring, which is bonded via —O— to a linear C$_{10-40}$ alkyl group", further preferably an "organic group having a benzene ring, which is bonded via —O— to a linear C$_{10-30}$ alkyl group", particularly preferably an "organic group having a benzene ring, which is bonded via —O— to a linear C$_{12-28}$ alkyl group", most preferably an "organic group having a benzene ring, which is bonded via —O— to a linear C$_{14}$-26 alkyl group".

The pseudo solid phase protecting group of the present invention is, for example, a group represented by the following formula (III) (hereinafter to be referred to as "pseudo solid phase protecting group (III)"):

wherein

** shows a bonding position to a group to be protected;

L is a single bond, or a group represented by the formula (a1) or (a1'):

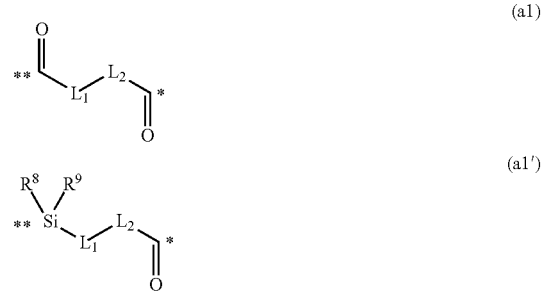

wherein

* shows the bonding position to Y;

** is as defined above;

R$^8$ and R$^9$ are each independently a C$_{1-22}$ hydrocarbon group;

L$_1$ is a divalent C$_{1-22}$ hydrocarbon group; and

L$_2$ is a single bond, or C(=O)N(R$^{2'}$)—R$^{1'}$—N(R$^3$)* wherein  shows the bonding position to L$_1$, * shows the bonding position to C=O, R$^{1'}$ is a C$_{1-22}$ alkylene group, R$^{2'}$ and R$^3$ are each independently a hydrogen atom or a C$_{1-22}$ alkyl group, or R$^{2'}$ and R$^3$ are optionally joined to form a ring, Y is a single bond, an oxygen atom, or NR wherein R is a hydrogen atom, an alkyl group or an aralkyl group, and Z is a group represented by the formula (a2), formula (a2') or formula (a2") {preferably formula (a2) or formula (a2')}:

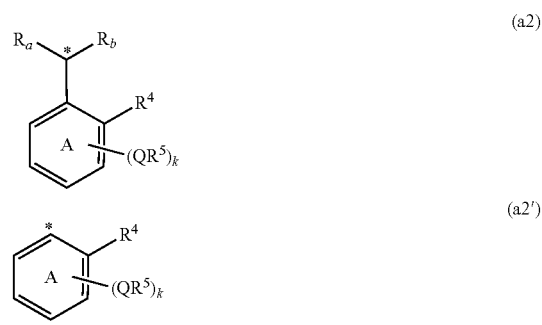

-continued

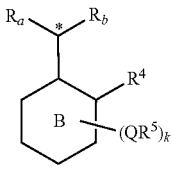
(a2")

wherein
* shows a bonding position;
$R^4$ is a hydrogen atom, or when $R_b$ is a group represented by the following formula (a3), optionally joined with $R^6$ of ring C to show a single bond or —O— and to form a fused ring (preferably fluorene ring or xanthene ring) together with ring A or ring B and ring C;
Q in the number of k are each independently —O—, —C(=O)—, —C(=O)O—, —OC(=O)—, —C(=O)NH— or —NHC(=O)—;
$R^5$ in the number of k are each independently a hydrocarbon group bonded via a single bond or a linker to an aliphatic hydrocarbon group having not less than 10 carbon atoms (preferably a hydrocarbon group bonded via a single bond or a linker to a linear aliphatic hydrocarbon group having not less than 10 carbon atoms);
k is an integer of 1 to 4;
ring A and ring B each independently optionally further have, in addition to $QR^5$ in the number of k, a substituent selected from the group consisting of a halogen atom, a $C_{1-6}$ alkyl group optionally substituted by a halogen atom(s), and a $C_{1-6}$ alkoxy group optionally substituted by a halogen atom(s);
$R_a$ is a hydrogen atom, or a phenyl group optionally substituted by a halogen atom (preferably, a hydrogen atom); and
$R_b$ is a hydrogen atom, or a group represented by the formula (a3):

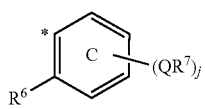
(a3)

wherein * shows a bonding position;
j is an integer of 0 to 4;
Q in the number of j are each independently as defined above;
$R^7$ in the number of j are each independently a hydrocarbon group bonded via a single bond or a linker to an aliphatic hydrocarbon group having not less than 10 carbon atoms (preferably, a hydrocarbon group bonded via a single bond or a linker to a linear aliphatic hydrocarbon group having not less than 10 carbon atoms);
$R^6$ is a hydrogen atom, or optionally joined with $R^4$ of ring A or ring B to show a single bond or —O— and to form a fused ring (preferably fluorene ring or xanthene ring) together with ring A or ring B and ring C; and
ring C optionally further has, in addition to $OR^7$ in the number of j, a substituent selected from the group consisting of a halogen atom, a $C_{1-6}$ alkyl group optionally substituted by a halogen atom(s), and a $C_{1-6}$ alkoxy group optionally substituted by a halogen atom(s); or
$R_a$ and $R_b$ are joined to form an oxo group.

Examples of the group protected by pseudo solid phase protecting group (III) include a hydroxy group, an amino group, a carboxy group.
Each aliphatic hydrocarbon group having not less than 10 carbon atoms for $R^5$ in the formula (a2), the formula (a2') and the formula (a2"), and $R^7$ for the formula (a3) is independently preferably a group selected from a linear $C_{10-40}$ alkyl group and a linear $C_{10-40}$ alkenyl group, more preferably a linear $C_{10-40}$ alkyl group, further preferably a linear $C_{10-30}$ alkyl group, particularly preferably a linear $C_{12-28}$ alkyl group, most preferably a linear $C_{14-26}$ alkyl group.
Each linker for $R^5$ in the formula (a2), the formula (a2') and the formula (a2") and $R^7$ for the formula (a3) is independently preferably —O—, —C(=O)—, —C(=O)O—, —OC(=O)—, —C(=O)NH— or —NHC(=O)—, more preferably —O—.
$R^5$ in the formula (a2), the formula (a2') and the formula (a2") and $R^7$ in the formula (a3) (namely, a hydrocarbon group bonded via a single bond or a linker to an aliphatic hydrocarbon group having not less than 10 carbon atoms) are each independently preferably a group selected from a linear $C_{10-40}$ alkyl group and a linear $C_{10-40}$ alkenyl group, more preferably a linear $C_{10-40}$ alkyl group, further preferably a linear $C_{10-30}$ alkyl group, particularly preferably a linear $C_{12-28}$ alkyl group, most preferably a linear $C_{14-26}$ alkyl group.
Q in the formula (a2), the formula (a2'), the formula (a2") and the formula (a3) is preferably —O—.
In the formula (III), a preferable embodiment of L represented by the formula (a1) is a group wherein
$L_1$ is a divalent $C_{1-22}$ hydrocarbon group, or $CH_2$—O-1, 4-phenylene-O—$CH_2$; and
$L_2$ is a single bond, or a group represented by C(=O)N($R^{2'}$)—$R^{1'}$—N($R^3$)' wherein  shows the bonding position to $L_1$, *** shows the bonding position to C=O, $R^{1'}$ is a $C_{1-6}$ alkylene group, $R^{2'}$ and $R^3$ are each independently a hydrogen atom, or an optionally substituted $C_{1-6}$ alkyl group, or $R^{2'}$ and $R^3$ are optionally joined to form an optionally substituted $C_{1-6}$ alkylene bond.
Another preferable embodiment of L represented by the formula (a1) is a group wherein
$L_1$ is a divalent $C_{1-22}$ hydrocarbon group; and
$L_2$ is a single bond.
Another preferable embodiment of L represented by the formula (a1) is a group wherein
$L_1$ is an ethylene group; and
$L_2$ is a group represented by C(=O)N($R^{2'}$)—$R^{1'}$—N($R^3$)* wherein  shows the bonding position to $L_1$, * shows the bonding position to C=O, $R^{1'}$ is a $C_{1-22}$ alkylene group, $R^{2'}$ and $R^3$ are each independently a hydrogen atom or a $C_{1-22}$ alkyl group, or $R^{2'}$ and $R^3$ are optionally joined to form a ring.
Another preferable embodiment of L represented by the formula (a1) is a group wherein
$L_1$ is an ethylene group; and
$L_2$ is a group represented by C(=O) N($R^{2'}$)—$R^{1'}$—N($R^3$)* wherein  shows the bonding position to $L_1$, * shows the bonding position to C=O, and N($R^{2'}$)—$R^{1'}$—N($R^3$) moiety forms a piperazinediyl group (e.g., 1,4-piperazinediyl group).
Another preferable embodiment of L represented by the formula (a1) is a group wherein
$L_1$ is an ethylene group; and
$L_2$ is a group represented by C(=O) N($R^{2'}$)—$R^{1'}$—N($R^3$)* wherein  shows the bonding position to $L_1$, * shows the bonding position to C=O, $R^{1'}$ is a pentylene group or a hexylene group, and $R^{2'}$ and $R^3$ are each independently a hydrogen atom or a methyl group.

A particularly preferable embodiment of L represented by the formula (a1) is a succinyl group which is easily available at a low cost.

Now, L represented by the formula (a1') in the formula (III) is explained.

$L_1$ in the formula (a1') is preferably a divalent $C_{6-10}$ aromatic hydrocarbon group, more preferably a phenylene group.

$L_2$ in the formula (a1') is preferably a single bond.

A preferable combination of $L_1$ and $L_2$ in the formula (a1') is a combination of $L_1$ being a divalent $C_{6-10}$ aromatic hydrocarbon group, and $L_2$ being a single bond. A more preferable combination of $L_1$ and $L_2$ in the formula (a1') is a combination of $L_1$ being a phenylene group, and $L_2$ being a single bond.

$R^8$ and $R^9$ in the formula (a1') are each independently preferably a $C_{1-22}$ alkyl group, more preferably a $C_{1-10}$ alkyl group.

A preferable embodiment of L represented by the formula (a1') is a group wherein
$R^8$ and $R^9$ are each independently a $C_{1-22}$ alkyl group;
$L_1$ is a divalent $C_{6-10}$ aromatic hydrocarbon group; and
$L_2$ is a single bond.

Another preferable embodiment of L represented by the formula (a1') is a group wherein
$R^8$ and $R^9$ are each independently a $C_{1-10}$ alkyl group;
$L_1$ is a phenylene group; and
$L_2$ is a single bond.

Y in the formula (III) is a single bond, an oxygen atom, or NR (R is a hydrogen atom, an alkyl group or an aralkyl group). When Y is a single bond, L is a single bond, Z is a group represented by the formula (a2), $R^4$ is a hydrogen atom, and $R_a$ and $R_b$ are preferably joined to form an oxo group.

Y in the formula (III) is preferably an oxygen atom, or NR (R is a hydrogen atom, an alkyl group or an aralkyl group), R is preferably a hydrogen atom, a $C_{1-6}$ alkyl group or a $C_{7-16}$ aralkyl group, more preferably a hydrogen atom, methyl, ethyl or benzyl, particularly preferably a hydrogen atom. Y is particularly preferably an oxygen atom.

Z in the formula (III) is preferably a group represented by the formula (a2) or the formula (a2'), more preferably a group represented by the formula (a2). In the formula (a2), $R^4$ is preferably a hydrogen atom. In the formula (a2), $R_a$ and $R_b$ are each preferably a hydrogen atom.

A preferable embodiment of Z represented by the formula (a2) is a group wherein
$R_a$ and $R_b$ are each a hydrogen atom;
$R^4$ is a hydrogen atom;
k is an integer of 1-3;
Q in the number of k are each —O—; and
$R^5$ in the number of k are each independently a linear $C_{10-40}$ alkyl group.

When Z is this embodiment, it is more preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom, or L-Y is a single bond, and it is further preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom.

Another preferable embodiment of Z represented by the formula (a2) is a group wherein
$R_a$ and $R_b$ are each a hydrogen atom;
$R^4$ is a hydrogen atom;
k is an integer of 1-3;
Q in the number of k are each —O—; and
$R^5$ in the number of k are each independently a benzyl group bonded via —O— to 1 to 3 linear $C_{10-40}$ alkyl groups, or a cyclohexylmethyl group bonded via —O— to 1 to 3 linear $C_{10-40}$ alkyl groups; and
ring A optionally further has, in addition to $QR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom.

When Z is this embodiment, it is more preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom, or L-Y is a single bond, and it is further preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom.

Another preferable embodiment of Z represented by the formula (a2) is a group wherein
$R_a$ and $R^4$ are each a hydrogen atom; and
$R_b$ is a group represented by the formula (a3) wherein * is a bonding position, j is an integer of 0-3, Q in the number of j is —O—, $R^7$ in the number of j are each independently a $C_{10-40}$ alkyl group, $R^6$ is a hydrogen atom.

When Z is this embodiment, it is more preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom, or L-Y is a single bond, and it is further preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom.

A still another preferable embodiment of Z represented by the formula (a2) is a group wherein
$R_a$ is a hydrogen atom; and
$R_b$ is a group represented by the formula (a3) wherein * is a bonding position, j is an integer of 0-3, Q in the number of j is —O—, $R^7$ in the number of j are each independently a linear $C_{10-40}$ alkyl group, and $R^6$ is joined with $R^4$ of ring A to form a single bond or —O—, whereby ring A and ring C are joined to form a fluorene ring or a xanthene ring.

When Z is this embodiment, it is more preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom, or L-Y is a single bond, and it is further preferable that L is a succinyl group, or a group represented by the formula (a1') (in the formula (a1'), $R^8$ and $R^9$ are each independently a $C_{1-10}$ alkyl group, $L_1$ is a divalent phenylene group, and $L_2$ is a single bond), and Y is an oxygen atom.

Another preferable embodiment of Z represented by the formula (a2) is a group wherein
$R_a$ and $R_b$ are joined to form an oxo group;
$R^4$ is a hydrogen atom;
k is an integer of 1 to 3;
Q in the number of k is —O—; and
$R^5$ in the number of k are each independently linear $C_{10-40}$ alkyl group.

When Z is this embodiment, it is more preferable that L-Y is a single bond or a succinyl-1,4-piperazinediyl group, and it is further preferable that L-Y is a single bond.

Another preferable embodiment of Z represented by the formula (a2) is a group wherein $R_a$ and $R_b$ are joined to form an oxo group;

$R^4$ is a hydrogen atom;

k is an integer of 1-3;

Q in the number of k are each —O—; and $R^5$ in the number of k are each independently a benzyl group bonded via —O— to 1 to 3 linear $C_{10-40}$ alkyl groups, or a cyclohexylmethyl group bonded via —O— to 1 to 3 linear $C_{10-40}$ alkyl groups; and ring A optionally further has, in addition to $QR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom.

When Z is this embodiment, it is more preferable that L-Y is a single bond or a succinyl-1,4-piperazinediyl group, and it is further preferable that L-Y is a single bond.

The pseudo solid phase protecting group (III) is preferably a group not removed under acidic conditions but removed under basic conditions.

Specific examples 1 of pseudo solid phase protecting group (III) having a linear aliphatic hydrocarbon group having not less than 10 carbon atoms, which is for protecting a hydroxy group include groups wherein L is a succinyl group, or a group represented by the formula (a1') (the formula (a1') wherein $R^8$ and $R^9$ are each independently a $C_{1-10}$ alkyl group, $L^1$ is a divalent phenylene group, and $L^2$ is a single bond), and Y—Z is a 3,4,5-tri(octadecyloxy)benzyloxy group, 2,4-di(octadecyloxy)benzyloxy group, 2,4-di(docosyloxy)benzyloxy group, 3,5-di(docosyloxy)benzyloxy group, 3,5-bis[3',4',5'-tri(octadecyloxy)benzyloxy]benzyloxy group, 3,4,5-tris[3',4',5'-tri(octadecyloxy)benzyloxy]benzyloxy group, 3,4,5-tri(octadecyloxy)benzylamino group, 2,4-di(docosyloxy)benzylamino group, 3,5-di(docosyloxy)benzylamino group, bis(4-docosyloxyphenyl)methylamino group, 4-methoxy-2-[3',4',5'-tri(octadecyloxy)benzyloxy]benzylamino group, 4-methoxy-2-[3',4',5'-tri(octadecyloxy)cyclohexylmethyloxy]-benzylamino group, 2,4-bis(dodecyloxy)benzylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)benzyloxy]benzylamino group, 3,4,5-tris[3',4',5'-tri(octadecyloxy)benzyloxy]benzylamino group, 3,4,5-tri(octadecyloxy)cyclohexylmethyloxy group, 3,5-di(docosyloxy)cyclohexylmethyloxy group, 3,5-bis[3',4',5'-tri(octadecyloxy)cyclohexylmethyloxy]cyclohexylmethyloxy group, 3,4,5-tris[3',4',5'-tri(octadecyloxy)cyclohexylmethyloxy]-cyclohexylmethyloxy group, 3,4,5-tri(octadecyloxy)-cyclohexylmethylamino group, 2,4-di(docosyloxy)-cyclohexylmethylamino group, 3,5-di(docosyloxy)-cyclohexylmethylamino group, bis(4-docosyloxyphenyl)methylamino group, 4-methoxy-2-[3',4',5'-tri(octadecyloxy)-cyclohexylmethyloxy]cyclohexylmethylamino group, 4-methoxy-2-[3',4',5'-tri(octadecyloxy)cyclohexylmethyloxy]-cyclohexylmethylamino group, 2,4-bis(dodecyloxy)-cyclohexylmethylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)cyclohexylmethyloxy]-cyclohexylmethyloxy group, or 3,4,5-tris[3',4',5'-tri(octadecyloxy)cyclohexylmethyloxy]cyclohexylmethylamino group, groups wherein L-Y is a succinyl-1,4-piperazinediyl group, and Z is a 3,4,5-tri(octadecyloxy)benzoyl group, 2,4-di(octadecyloxy)benzoyl group, 2,4-di(docosyloxy)benzoyl group, 3,5-di(docosyloxy)benzoyl group, 3,5-bis[3',4',5'-tri(octadecyloxy)benzyloxy]benzoyl group, or 3,4,5-tris[3',4',5'-tri(octadecyloxy)benzyloxy]benzoyl group, and groups wherein L-Y is a single bond, and Z is a (3,5-didocosyloxyphenyl)diphenylmethyl group or bis(4-chlorophenyl)(3,5-didocosyloxyphenyl)methyl group.

Specific examples 2 of pseudo solid phase protecting group (III) having a linear aliphatic hydrocarbon group having not less than 10 carbon atoms, which is for protecting an amino group or an imino group include groups wherein L-Y is a single bond, and Z is a 3,4,5-tri(octadecyloxy)benzoyl group, 2,4-di(octadecyloxy)benzoyl group, 2,4-di(docosyloxy)benzoyl group, 3,5-di(docosyloxy)benzoyl group, 3,5-bis[3',4',5'-tri(octadecyloxy)benzyloxy]benzoyl group, 3,4,5-tris[3',4',5'-tri(octadecyloxy)benzyloxy]benzoyl group, (3,5-didocosyloxyphenyl)diphenylmethyl group, or bis(4-chlorophenyl)(3,5-didocosyloxyphenyl)methyl group.

Specific examples 3 of pseudo solid phase protecting group (III) having a linear aliphatic hydrocarbon group having not less than 10 carbon atoms, which is for protecting a carboxy group include groups wherein L-Y is a single bond, and Z is a 3,4,5-tri(octadecyloxy)benzyl group, 2,4-di(octadecyloxy)benzyl group, 2,4-di(docosyloxy)benzyl group, 3,5-di(docosyloxy)benzyl group, 3,5-bis[3',4',5'-tri(octadecyloxy)benzyloxy]benzyl group, 3,4,5-tris[3',4',5'-tri(octadecyloxy)benzyloxy]benzyl group, (3,5-didocosyloxyphenyl)diphenylmethyl group, or bis(4-chlorophenyl)(3,5-didocosyloxyphenyl)methyl group.

Specific examples 4 of pseudo solid phase protecting group (III) having a branched chain aliphatic hydrocarbon group having not less than 10 carbon atoms, which is for protecting a hydroxy group include groups wherein L is a succinyl group, or a group represented by the formula (a1') (in the formula (a1'), $R^8$ and $R^9$ are each independently a $C_{1-10}$ alkyl group, $L^1$ is a divalent phenylene group, and $L^2$ is a single bond), and Y—Z is a 4-(2',3'-dihydrophytyloxy)benzyloxy group, 4-(3,7,11-trimethyldodecyloxy)benzyloxy group, 4-[2,2,4,8,10,10-hexamethyl-5-dodecanoylamino]benzyloxy group, 4-(2',3'-dihydrophytyloxy)-2-methylbenzyloxy group, 4-(2',3'-dihydrophytyloxy)-2-methoxybenzyloxy group, 2,4-di(2',3'-dihydrophytyloxy)benzyloxy group, 3,5-di(2',3'-dihydrophytyloxy)benzyloxy group, 2-[3',4',5'-tri(2",3"-dihydrophytyloxy)benzyloxy]-4-methoxybenzyloxy group, 3,4,5-tri(2',3'-dihydrophytyloxy)benzyloxy group, 3,4,5-tris[3,4,5-tri(2',3'-dihydrophytyloxy)benzyloxy]benzyloxy group, 2,4-di(2-decyltetradecyloxy)benzyloxy group, 4-(2',3'-dihydrophytyloxy)benzylamino group, 4-(3,7,11-trimethyldodecyloxy)benzylamino group, 4-[2,2,4,8,10,10-hexamethyl-5-dodecanoylamino]benzylamino group, 4-(2',3'-dihydrophytyloxy)-2-methylbenzylamino group, 4-(2',3'-dihydrophytyloxy)-2-methoxybenzylamino group, 2,4-di(2',3'-dihydrophytyloxy)benzylamino group, 3,5-di(2',3'-dihydrophytyloxy)benzylamino group, 2-[3',4',5'-tri(2",3"-dihydrophytyloxy)benzyloxy]-4-methoxybenzylamino group, 3,4,5-tri(2',3'-dihydrophytyloxy)benzylamino group, 3,4,5-tris[3,4,5-tri(2',3'-dihydrophytyloxy)benzyloxy]benzylamino group, {[(2-chloro-5-(2',3'-dihydrophytyloxy)phenyl)]phenylmethyl}amino group, {[2,3,4-tri(2',3'-dihydrophytyloxy)phenyl]phenylmethyl}amino group, or {bis[4-(2',3'-dihydrophytyloxy)phenyl]methyl}amino group.

Here, 2,3-dihydrophytyl means 3,7,11,15-tetramethylhexadecyl. The same applies to 2',3'-dihydrophytyl and 2",3"-dihydrophytyl.

Specific examples 5 of pseudo solid phase protecting group (III) having a branched chain aliphatic hydrocarbon group having not less than 10 carbon atoms, which is for protecting an amino group or an imino group include groups wherein L-Y is a single bond, and Z is a 4-(2',3'-dihydrophytyloxy)benzoyl group, 4-(3,7,11-trimethyldodecyloxy)benzoyl group, 4-[2,2,4,8,10,10-hexamethyl-5-dodecanoylamino]benzoyl group, 4-(2',3'-dihydrophytyloxy)-2-methylbenzoyl group, 4-(2',3'-dihydrophytyloxy)-2-methoxybenzoyl group, 2,4-di(2',3'-dihydrophytyloxy)benzoyl group, 3,5-di(2',3'-dihydrophytyloxy)benzoyl group, 2-[3',4',5'-tri(2",3"-dihydrophytyloxy)benzyloxy]-4-methoxybenzoyl group, 3,4,5-tri(2',3'-dihydrophytyloxy)benzoyl group, 3,4,5-tris[3,4,5-tri(2',3'-dihydrophytyloxy)benzyloxy]benzoyl group, or 2,4-di(2-decyltetradecyloxy)benzoyl group.

Specific examples 6 of pseudo solid phase protecting group (III) having a branched chain aliphatic hydrocarbon group having not less than 10 carbon atoms, which is for protecting a carboxy group include
groups wherein
L-Y is a single bond, and Z is a 4-(2',3'-dihydrophytyloxy)benzyl group, 4-(3,7,11-dihydrophytyloxy)benzyl group, 4-[2,2,4,8,10,10-hexamethyl-5-dodecanoylamino]benzyl group, 4-(2',3'-dihydrophytyloxy)-2-methylbenzyl group, 4-(2',3'-dihydrophytyloxy)-2-methoxybenzyl group, 2,4-di(2',3'-dihydrophytyloxy)benzyl group, 3,5-di(2',3'-dihydrophytyloxy)benzyl group, 2-[3',4',5'-tri(2",3"-dihydrophytyloxy)benzyloxy]-4-methoxybenzyl group, 3,4,5-tri(2',3'-dihydrophytyloxy)benzyl group, 3,4,5-tris[3,4,5-tri(2',3'-dihydrophytyloxy)benzyloxy]benzyl group, or 2,4-di(2-decyltetradecyloxy)benzyl group.

The pseudo solid phase protecting group (III) is preferably any of the aforementioned Specific examples 1 to Specific examples 6, more preferably Specific examples 1 to Specific examples 3, of pseudo solid phase protecting group (III).

The pseudo solid phase protecting group (III) is still more preferably
a group wherein L is a succinyl group or a group represented by the formula (a1') (the formula (a1') wherein $R^8$ and $R^9$ are each independently a $C_{1-10}$ alkyl group, $L_1$ is a divalent phenylene group, $L_2$ is a single bond), and Y—Z is a 3,4,5-tri(octadecyloxy)benzyloxy group, 2,4-di(octadecyloxy)benzyloxy group, 2,4-di(docosyloxy)benzyloxy group, 3,5-di(docosyloxy)benzyloxy group, 3,5-bis[3',4',5'-tri(octadecyloxy)benzyloxy]benzyloxy group, 3,4,5-tris[3',4',5'-tri(octadecyloxy)benzyloxy]benzyloxy group, 3,4,5-tri(octadecyloxy)benzylamino group, 2,4-di(docosyloxy)benzylamino group, 3,5-di(docosyloxy)benzylamino group, di(4-docosyloxyphenyl)methylamino group, 4-methoxy-2-[3',4',5'-tri(octadecyloxy)benzyloxy]benzylamino group, 4-methoxy-2-[3',4',5'-tri(octadecyloxy)cyclohexylmethyloxy]-benzylamino group, 2,4-di(dodecyloxy)benzylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)benzyloxy]benzylamino group, or 3,4,5-tris[3',4',5'-tri(octadecyloxy)benzyloxy]benzylamino group,
a group wherein L-Y is a succinyl-1,4-piperazinediyl group, and Z is a 3,4,5-tri(octadecyloxy)benzoyl group, 2,4-di(octadecyloxy)benzoyl group, 2,4-di(docosyloxy)benzoyl group, 3,5-di(docosyloxy)benzoyl group, 3,5-bis[3',4',5'-tri(octadecyloxy)benzyloxy]benzoyl group, or 3,4,5-tris[3',4',5'-tri(octadecyloxy)benzyloxy]benzoyl group, or
a group wherein L-Y is a single bond, and Z is a 3,4,5-tri(octadecyloxy)benzoyl group, 2,4-di(octadecyloxy)benzoyl group, 2,4-di(docosyloxy)benzoyl group, 3,5-di(docosyloxy)benzoyl group, 3,5-bis[3',4',5'-tri(octadecyloxy)benzyloxy]benzoyl group, or 3,4,5-tris[3',4',5'-tri(octadecyloxy)benzyloxy]benzoyl group.

The pseudo solid phase protecting group (III) is further preferably
a group wherein L is a succinyl group, or a group represented by the formula (a1') (the formula (a1') wherein $R^8$ and $R^9$ are each independently a $C_{1-10}$ alkyl group, $L_1$ is a divalent phenylene group, $L_2$ is a single bond), and Y—Z is a 3,4,5-tri(octadecyloxy)benzyloxy group, 3,5-di(docosyloxy)benzyloxy group, 3,5-bis[3',4',5'-tri(octadecyloxy)benzyloxy]benzyloxy group, 3,4,5-tris[3',4',5'-tri(octadecyloxy)benzyloxy]benzyloxy group, 3,4,5-tri(octadecyloxy)benzylamino group, 2,4-di(docosyloxy)benzylamino group, 3,5-di(docosyloxy)benzylamino group, di(4-docosyloxyphenyl)methylamino group, 4-methoxy-2-[3',4',5'-tri(octadecyloxy)benzyloxy]benzylamino group, 4-methoxy-2-[3',4',5'-tri(octadecyloxy)cyclohexylmethyloxy]-benzylamino group, 2,4-di(dodecyloxy)benzylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)benzyloxy]benzylamino group, or 3,4,5-tris[3',4',5'-tri(octadecyloxy)benzyloxy]benzylamino group, or
a group wherein L-Y is a single bond, and Z is a 3,4,5-tri(octadecyloxy)benzoyl group.

The pseudo solid phase protecting group (III) is particularly preferably
a group wherein L is a succinyl group, and Y—Z is a 3,4,5-tri(octadecyloxy)benzyloxy group, 3,5-di(docosyloxy)benzyloxy group, 3,5-bis[3',4',5'-tri(octadecyloxy)benzyloxy]benzyloxy group, 3,4,5-tris[3',4',5'-tri(octadecyloxy)benzyloxy]benzyloxy group, 3,4,5-tri(octadecyloxy)benzylamino group, 2,4-di(docosyloxy)benzylamino group, 3,5-di(docosyloxy)benzylamino group, di(4-docosyloxyphenyl)methylamino group, 4-methoxy-2-[3',4',5'-tri(octadecyloxy)benzyloxy]benzylamino group, 4-methoxy-2-[3',4',5'-tri(octadecyloxy)cyclohexylmethyloxy]-benzylamino group, 2,4-di(dodecyloxy)benzylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)benzyloxy]benzylamino group, or 3,4,5-tris[3',4',5'-tri(octadecyloxy)benzyloxy]benzylamino group, or
a group wherein L-Y is a single bond, and Z is a 3,4,5-tri(octadecyloxy)benzoyl group.

The pseudo solid phase protecting group (III) is most preferably a group wherein L is a succinyl group, and Y—Z is a 3,4,5-tri(octadecyloxy)benzyloxy group, 3,5-di(docosyloxy)benzyloxy group, 3,5-bis[3',4',5'-tri(octadecyloxy)benzyloxy]benzyloxy group, 3,4,5-tris[3',4',5'-tri(octadecyloxy)benzyloxy]benzyloxy group, 3,4,5-tri(octadecyloxy)benzylamino group, 2,4-di(docosyloxy)benzylamino group, 3,5-di(docosyloxy)benzylamino group, di(4-docosyloxyphenyl)methylamino group, 4-methoxy-2-[3',4',5'-tri(octadecyloxy)benzyloxy]benzylamino group, 4-methoxy-2-[3',4',5'-tri(octadecyloxy)cyclohexylmethyloxy]-benzylamino group, 2,4-di(dodecyloxy)benzylamino group, phenyl(2,3,4-tri(octadecyloxy)phenyl)methylamino group, bis[4-(12-docosyloxydodecyloxy)phenyl]methylamino group, 3,5-bis[3',4',5'-tri(octadecyloxy)benzyloxy]benzylamino group, or 3,4,5-tris[3',4',5'-tri(octadecyloxy)benzyloxy]benzylamino group.

A compound used for forming a pseudo solid phase protecting group can be produced by a method known per se (e.g., the method described in the aforementioned patent document 1 or 2, esterification, silylation etc.) or a method analogous thereto. For example, an alcohol compound or an amine compound represented by the formula: Z—Y—H used for forming a pseudo solid phase protecting group can be produced by the following steps or steps analogous thereto.

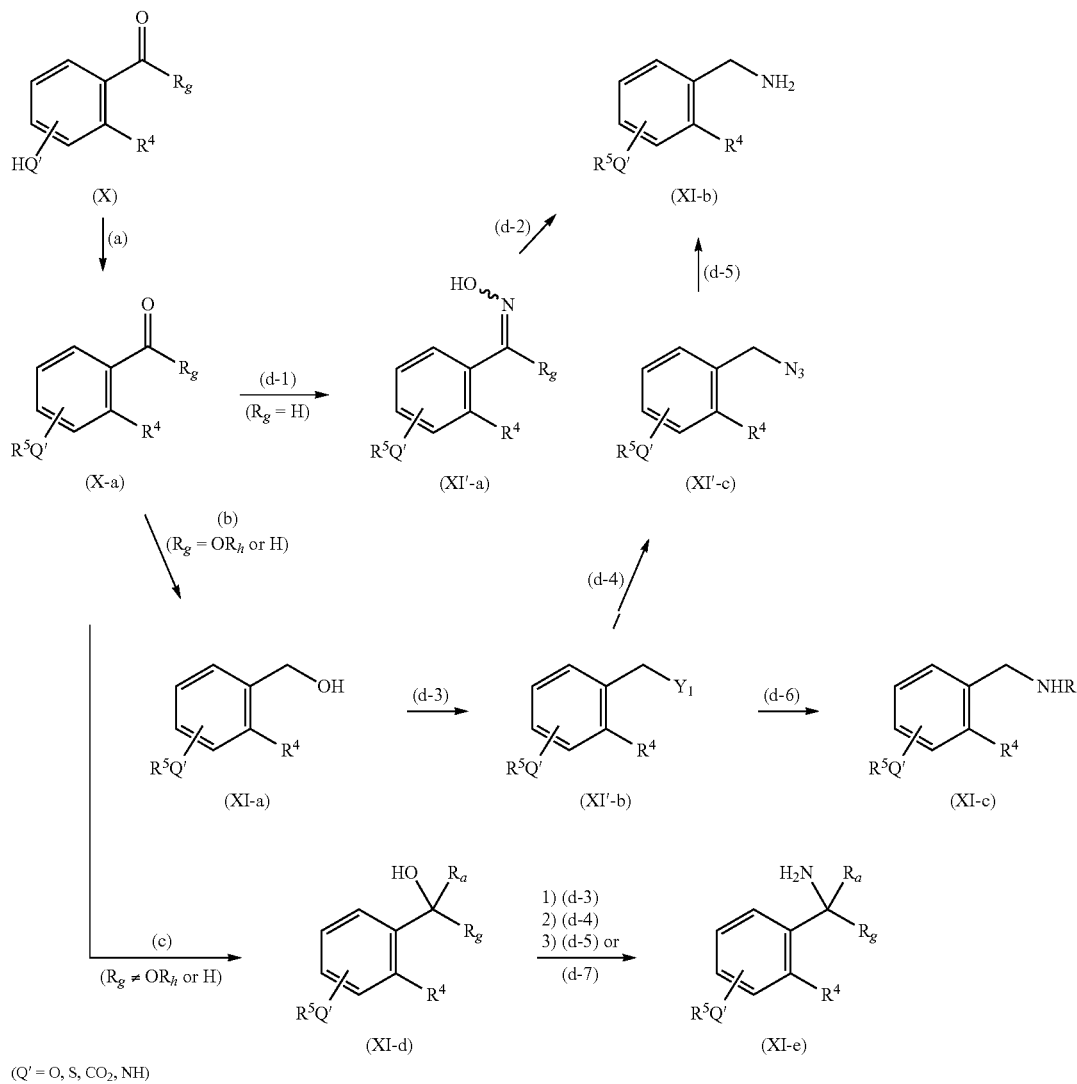

(Q' = O, S, CO$_2$, NH)

wherein Q' is —O—, —S—, —C(=O)O— or —NH—, R$_g$ is a hydrogen atom, an OR$_h$ group (wherein R$_h$ is an alkyl group such as C$_{1-6}$ alkyl group and the like, an aralkyl group such as benzyl group and the like, and the like) or a group represented by the formula (a3):

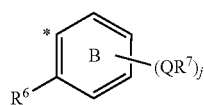

(a3)

wherein each symbol is as defined above, Y$_1$ is a leaving group such as a halogen atom and the like, and other symbols are as defined above.

Step (a)

In this step, R$^5$ is introduced into Q'H (wherein Q' is —O—, —S—, —C(=O)O— or —NH—) in a compound represented by the formula (X) to produce a compound represented by the formula (X-a). When Q' is —O—, —S— or —NH—, this reaction is performed in a solvent that does not influence the reaction, in the presence or absence of a base and using halide (chloride, bromide or iodide) corresponding to R$^5$, carboxylic acid or acid halide corresponding to R$^5$ or an alkylsulfonyloxylation product (e.g., methanesulfonyloxylation product etc.) or an arylsulfonyloxylation product (e.g., p-toluenesulfonyloxylation product etc.) corresponding to R$^5$. When Q' is —O—, this reaction can also be performed under Mitsunobu reaction conditions in which compound (X) and hydroxide corresponding to R$^5$ are reacted in the presence of triphenylphosphine and diisopropyl azodicarboxylate. Furthermore, when Q' is —C(=O)O—, for example, compound (X-a) can be synthesized by reacting compound (X) with amine or hydroxide corresponding to R$^5$ in the presence of a condensing agent.

Examples of the base include alkali metal salts such as sodium carbonate, sodium hydrogen carbonate, potassium carbonate, potassium tert-butoxide and the like; alkali metal hydrides such as sodium hydride, potassium hydride and the like; amines such as pyridine, triethylamine, N,N-dimethylaniline, 1,8-diazabicyclo[5.4.0]-7-undecene and the like, and the like, of which sodium carbonate, potassium carbonate, sodium hydride and the like are preferable.

Examples of the solvent include aromatic hydrocarbons such as toluene, xylene and the like; ethers such as tetrahydrofuran, dioxane and the like; amides such as dimethylformamide, dimethylacetamide and the like; halogenated hydrocarbons such as chloroform, dichloromethane and the like; nitriles such as acetonitrile and the like, N-methylpyrrolidone and the like, or a mixture thereof, of which dimethylformamide, tetrahydrofuran, toluene, N-methylpyrrolidone and the like are preferable.

The reaction temperature is preferably 50 to 150° C., more preferably 60 to 130° C. The reaction time is preferably 2 to 30 hr, more preferably 3 to 10 hr.

Step (b)

In this step, compound (X-a) is reduced to produce a compound represented by the formula (XI-a). This reduction reaction can be performed by a method using a reducing agent.

Examples of the reducing agent to be used for this reduction reaction include metal hydrides (sodium borohydride, lithium borohydride, sodium cyanoborohydride, sodium triacetoxyborohydride, dibutylaluminum hydride, aluminum hydride, lithium aluminum hydride etc.) and the like, of which sodium borohydride, dibutylaluminum hydride and the like are preferable.

This reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; or a mixture thereof, of which tetrahydrofuran, toluene and the like are preferable. The reaction temperature is preferably 0 to 100° C., more preferably 30 to 70° C. The reaction time is preferably 1 to 24 hr, more preferably 2 to 5 hr.

Step (c)

In this step, compound (X-a) wherein $R_g$ is not a hydrogen atom or $OR_h$ group is reduced by a method similar to the above-mentioned step (b).

Step (d-1)

In this step, compound (X-a) wherein $R_g$ is a hydrogen atom is oximated to produce a compound represented by the formula (XI'-a).

The oximation reaction is performed by reacting compound (X-a) with an acid addition salt of hydroxylamine in a solvent that does not influence the reaction, in the presence of a base.

Examples of the acid addition salt of hydroxylamine include salts of mineral acids such as hydrochloride, sulfate, nitrate salt and the like, organic acid salts such as acetate, trifluoroacetate, methanesulfonate, trifluoromethanesulfonate, p-toluenesulfonate and the like, and the like, and hydrochloride is particularly preferable.

Examples of the base include alkali metal salts such as potassium hydroxide, sodium hydroxide, sodium hydrogen carbonate, potassium carbonate and the like; organic amines such as pyridine, triethylamine, diisopropylethylamine, N,N-dimethylaniline, 1,8-diazabicyclo[5.4.0]undeca-7-en and the like, and the like, of which triethylamine, diisopropylethylamine and the like are preferable.

Examples of the solvent include halogenated hydrocarbons such as chloroform, dichloromethane and the like; aromatic hydrocarbons such as toluene, xylene and the like; ethers such as tetrahydrofuran, dioxane and the like; and/or a mixture thereof, of which dichloromethane, chloroform, toluene and the like are preferable. The reaction temperature is preferably 10 to 100° C., more preferably 20 to 60° C. The reaction time is preferably 0.5 to 30 hr, more preferably 2 to 20 hr.

Step (d-2)

In this step, compound (XI'-a) is reduced by catalytic hydrogenation reaction in the presence of a metal catalyst such as palladium-carbon, Raney-nickel and the like, or reducing agent such as metal hydride and the like similar to that in the aforementioned step (b) to produce a compound represented by the formula (XI-b).

Compound (XI-b) can also be produced by step (d-3), step (d-4) and step (d-5).

Step (d-3)

In this step, compound (XI-a) is halogenated using, for example, a chlorinating agent such as acetyl chloride, thionyl chloride and the like, or a brominating agent such as acetyl bromide, phosphorus tribromide, diphenylphosphine/bromine and the like to produce a compound represented by the formula (XI'-b).

Examples of the solvent include halogenated hydrocarbons such as chloroform, dichloromethane and the like; aromatic hydrocarbons such as toluene, xylene and the like; ethers such as tetrahydrofuran, dioxane and the like; and a mixture thereof, of which chloroform, tetrahydrofuran, toluene and the like are preferable. The reaction temperature is preferably 10 to 150° C., more preferably 30 to 80° C. The reaction time is preferably 0.5 to 30 hr, more preferably 2 to 20 hr.

Step (d-4)

In this step, compound (XI'-b) is azidated using an azidating agent such as sodium azide and the like to produce a compound represented by the formula (XI'-c). This reaction is performed by reacting compound (XI'-b) with an azidating agent in a solvent that does not influence the reaction.

Examples of the solvent include halogenated hydrocarbons such as chloroform, dichloromethane and the like; aromatic hydrocarbons such as toluene, xylene and the like; ethers such as tetrahydrofuran, dioxane and the like; amides such as N,N-dimethylformamide and the like; and a mixture thereof, of which chloroform, N,N-dimethylformamide and the like are preferable. The reaction temperature is preferably 10 to −150° C., more preferably 20 to 100° C. The reaction time is preferably 0.5 to hr, more preferably 2 to 20 hr.

Step (d-5)

In this step, compound (XI'-c) is aminated to produce compound (XI'-b). This reaction is performed by reacting compound (XI'-c) with triphenylphosphine in a solvent that does not influence the reaction, in the presence of water, or by catalytic hydrogenation reduction.

The amount of triphenylphosphine to be used is preferably 1 to 10 mol, particularly preferably 1 to 0.5 mol, per 1 mol of compound (XI'-c). The amount of water to be used is preferably 1 to 10 mol, particularly preferably 1 to 5 mol, per 1 mol of compound (XI'-c).

Examples of the solvent include aromatic hydrocarbons such as toluene, xylene and the like; ethers such as tetrahydrofuran, dioxane and the like; and a mixture thereof, of which toluene, tetrahydrofuran and the like are preferable. The reaction temperature is preferably 10 to 150° C., more preferably 20 to 100° C. The reaction time is preferably 0.5 to 30 hr, more preferably 2 to for 20 hr.

Step (d-6)

In this step, compound (XI'-b) is reacted with $RNH_2$ (R is as defined above) to produce a compound represented by the formula (XI-c) wherein Y is a —NHR group. In this step, compound (XI'-b) is reacted with amine represented by R—$NH_2$ in a solvent that does not influence the reaction and, where necessary, in the presence of, for example, a base such as tertiary amine and the like (e.g., triethylamine, diisopropylethylamine and the like).

Examples of the solvent include aromatic hydrocarbons such as toluene, xylene and the like; ethers such as tetrahydrofuran, dioxane and the like; and, halogenated hydrocarbons such as chloroform, dichloromethane and the like, and a mixture thereof, of which toluene, tetrahydrofuran, chloroform and the like are preferable. The reaction temperature is preferably 10 to 100° C., more preferably 20 to 60° C. The reaction time is preferably 0.5 to 30 hr, more preferably 2 to 20 hr.

Step (d-7)

In this step, compound (XI-d) is reacted with a compound having a —$CONH_2$ group or a —$OCONH_2$ group, and treated with a base to produce compound (XI-e). The reaction of compound (XI-d) and a compound having a —$CONH_2$ group or a —$OCONH_2$ group is performed in a solvent that does not influence the reaction, under an acid catalyst.

Examples of the acid catalyst include methanesulfonic acid, trifluoromethanesulfonic acid, toluenesulfonic acid and the like, of which methanesulfonic acid, toluenesulfonic acid are preferable. The amount of the acid catalyst to be used is preferably 0.05 to 0.5 mol, particularly preferably 0.1 to 0.3 mol, per 1 mol of compound (XI-d).

Examples of the compound having a —$CONH_2$ group or a —$OCONH_2$ group include Fmoc-$NH_2$, $HCONH_2$, $CF_3CONH_2$, $AcNH_2$, $EtOCONH_2$, Cbz-$NH_2$ and the like, of which Fmoc-$NH_2$, $EtOCONH_2$ and the like are preferable. As used herein, "Fmoc-" means a 9-fluorenylmethoxycarbonyl group (hereinafter to be also referred to as Fmoc group), and "Cbz-" means a benzyloxycarbonyl group (hereinafter to be also referred to as Cbz group).

As the reagent to be used as a material for step (a) [i.e., hydroxide, halide, alkylsulfonyloxylation product (e.g., methanesulfonyloxylation product etc.) or an arylsulfonyloxylation product (e.g., p-toluenesulfonyloxylation product etc. corresponding to $R^5$), hereinafter to be abbreviated as "reagent of step (a)"], a commercially available product can be used. In addition, the reagent of step (a) can be produced, for example, by
(1) halogenation, alkylsulfonyloxylation or arylsulfonyloxylation of hydroxide corresponding to $R^5$, or
(2) reduction reaction of unsaturated hydroxide corresponding to $R^5$ (e.g., catalytic hydrogenation reaction etc. in the presence of a metal catalyst such as platinum-carbon (Pt/C), palladium-carbon (Pd/C), rhodium-carbon (Rh/C), Raney-nickel and the like), and subsequent halogenation, alkylsulfonyloxylation or arylsulfonyloxylation.

Examples of the reagent for conversion of a hydroxy group to a leaving group in the production of the reagent of step (a) include, in addition to halogenating agents such as chlorinating agents (e.g., thionyl chloride, N-chlorosuccinimide (NCS) and the like), brominating agents (e.g., hydrobromic acid, acetyl bromide, N-bromosuccinimide (NBS), phosphorus tribromide, diphenylphosphine/bromine and the like) and the like, alkylsulfonylating agents (e.g., methanesulfonyl chloride, trifluoromethanesulfonyl chloride and the like), arylsulfonylating agents (e.g., benzenesulfonyl chloride, p-toluenesulfonyl chloride and the like), and the like, of which halogenating agents such as thionyl chloride, hydrobromic acid and the like are preferable.

This reaction is performed in a solvent that does not influence the reaction, and examples of the solvent include water; halogenated hydrocarbons such as chloroform, dichloromethane and the like; aromatic hydrocarbons such as benzene, toluene, xylene and the like; nitriles such as acetonitrile, propionitrile and the like; ethers such as tetrahydrofuran, 1,4-dioxane, diethyl ether and the like, of which water, halogenated hydrocarbons such as chloroform and the like are preferable. The reaction temperature is preferably 10 to 120° C., more preferably 50 to 100° C. The reaction time is preferably 1 to 72 hr, more preferably 3 to 24 hr.

A compound represented by the formula: Z—Y—H wherein Q' is a single bond can also be produced by, for example, the following method. That is, introduction of $R^5$ on the benzene ring can be performed by
(1) Friedel-Crafts reaction using halide (chloride, bromide, or iodide) corresponding to $R^5$, or carboxylic acid or acid halide corresponding to $R^5$,
(2) a method including subjecting a compound corresponding to the above-mentioned compound (X) (compound wherein Q'H is replaced with —CHO group) to carbon homologation by a Wittig reaction, followed by catalytic hydrogenation and the like, or
(3) conventionally-used organic synthesis reaction such as cross coupling using a metal catalyst and the like.

The reaction reagent and the like in the above-mentioned respective schemes are shown for convenience, and can be appropriately changed within the range of the above-mentioned definition.

Organic Compound Protected by the Pseudo Solid Phase Protecting Group of the Present Invention The organic compound protected by an organic group having one or more aliphatic hydrocarbon groups having not less than 10 carbon atoms (the pseudo solid phase protecting group of the present invention) is not particularly limited as long as it can be precipitated in a solvent, and an organic compound having a functional group such as hydroxy group (—OH), sulfanyl group (—SH), a carboxy group (—COOH), amino group (—NHR), imino group (—NH—), carboxamide group (—CONHR") (wherein R" is a hydrogen atom or a hydrocarbon group) and the like, wherein the functional group is protected by the pseudo solid phase protecting group of the present invention (hereinafter sometimes to be referred to as "protected organic compound"), can be used. The protected organic compound may be further protected by a protecting group different from the pseudo solid phase protecting group (e.g., protecting group used for nucleic acid synthesis). Examples of the protected organic compound include nucleoside, nucleotide, amino acid, peptide and the like disclosed in WO 2012/157723, WO 2012/157723, WO 2014/189142, JP-A-2010-116418, WO 2010/104169, WO 2010/113939, WO 2011/078295, WO 2012/029794, JP-A-2009-185063, JP-A-2010-275254, all of which are incorporated herein by reference in their entireties, and the like.

A preferable protected organic compound is nucleoside, nucleotide or oligonucleotide optionally further protected by a protecting group used for nucleic acid synthesis, or amino acid or peptide optionally further protected by a protecting group used for peptide synthesis. In the aforementioned nucleoside, nucleotide or oligonucleotide, at least one group selected from amino group and imino group of nucleic acid base, 2'- and 3'-hydroxy groups of ribose residue, and 3'-hydroxy group of deoxyribose residue is preferably protected by the pseudo solid phase protecting group of the present invention. When the aforementioned nucleoside, nucleotide or oligonucleotide is morpholino nucleoside, morpholino nucleotide or morpholino oligonucleotide, the 5'-hydroxy group of morpholine residue, rather than the aforementioned hydroxy group, may be protected by a pseudo solid phase protecting group.

A more preferable protected organic compound is a nucleoside or oligonucleotide, wherein at least one group selected from amino group and imino group of nucleic acid base, 2'- and 3'-hydroxy groups of ribose residue, 3'-hydroxy group of deoxyribose residue, and 5'-hydroxy group of morpholine residue is protected by the pseudo solid phase protecting group of the present invention, and other group is optionally further protected by a protecting group used for nucleic acid synthesis.

A further preferable protected organic compound is a nucleoside or oligonucleotide, wherein at least one group selected from amino group and imino group of nucleic acid base, 2'- and 3'-hydroxy groups of ribose residue, and 3'-hydroxy group of deoxyribose residue is protected by the pseudo solid phase protecting group of the present invention, and other group is optionally further protected by a protecting group used for nucleic acid synthesis.

A particularly preferable protected organic compound is a nucleoside or oligonucleotide, wherein at least one group selected from amino group and imino group of nucleic acid base, 3'-hydroxy group of ribose residue, and 3'-hydroxy group of deoxyribose residue is protected by the pseudo solid phase protecting group of the present invention, and other group is optionally further protected by a protecting group used for nucleic acid synthesis.

The most preferable protected organic compound is a nucleoside or oligonucleotide, wherein 3'-hydroxy group of ribose residue or 3'-hydroxy group of deoxyribose residue is protected by the pseudo solid phase protecting group of the present invention, and other group is optionally further protected by a protecting group used for nucleic acid synthesis.

Precipitation

The present invention also provides a method of precipitating a protected organic compound in a solvent by using the precipitation promoter of the present invention (hereinafter sometimes to be referred to as "the precipitation method of the present invention"), and a precipitation mixture obtained by such method, which contains the precipitation promoter and the protected organic compound. The aforementioned solvent is preferably a solvent containing a polar solvent, more preferably a mixed solvent of a polar solvent and a nonpolar solvent.

An organic compound protected by the pseudo solid phase protecting group of the present invention shows improved solubility in a nonpolar solvent as well as decreased solubility in a polar solvent, due to a pseudo solid phase protecting group which is a hydrophobic group. An organic compound protected by such pseudo solid phase protecting group is, for example, precipitated by adding a polar solvent to a solution of the organic compound dissolved in a nonpolar solvent, to achieve solid-liquid separation. The precipitation promoter of the present invention can promote precipitation of an organic compound protected by a pseudo solid phase protecting group in a solvent, and can improve the recovery rate thereof. In addition, a deprotected organic compound can also be obtained by removing the pseudo solid phase protecting group after obtaining the object product (i.e., organic compound protected by pseudo solid phase protecting group).

Examples of the polar solvent include alcohol solvents such as methanol, ethanol, isopropanol and the like; nitrile solvents such as acetonitrile, propionitrile and the like; ketone solvents such as acetone, 2-butanone and the like; polar ether solvents such as 1,4-dioxane, tetrahydrofuran and the like; amide solvents such as dimethylformamide, dimethylacetamide, N-methylpiperidone and the like, sulfoxide solvents such as dimethyl sulfoxide and the like. Only one kind of polar solvent may be used, or two or more kinds thereof may be used in combination. As the polar solvent, acetonitrile is particularly preferable. From the aspect of precipitation efficiency in the synthesis of oligonucleotide, the recovery rate tends to increase when methanol is used as a polar solvent. Since methanol inhibits coupling reaction in the phosphoramidite method, methanol needs to be completely removed from the precipitated oligonucleotide. However, drying takes a long time and it is problematically difficult to evaluate whether methanol remains in the system. On the other hand, acetonitrile tends to decrease precipitation efficiency, but does not inhibit coupling reaction in the phosphoramidite method. Therefore, oligonucleotide precipitated using acetonitrile does not require strict drying and evaluation of residual solvent. Using the precipitation promoter of the present invention, the object product can be precipitated and recovered in a high yield even when acetonitrile is used.

Examples of the nonpolar solvent include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Only one kind of nonpolar solvent may be used, or two or more kinds thereof may be used in combination. As the nonpolar solvent, halogenated solvents, aromatic solvents, ester solvents, aliphatic solvents, and a combination of these are preferable; dichloromethane, chloroform, 1,2-dichloroethane, benzene, toluene, xylene, mesitylene, hexane, pentane, heptane, nonane, cyclohexane, ethyl acetate, isopropyl acetate and a combination of these are more preferable; chloroform, dichloromethane, toluene, and a combination of these are more preferable.

To sufficiently precipitate a protected organic compound, the amount of the precipitation promoter of the present invention to be used is preferably not less than 0.1 molar equivalent, more preferably not less than 0.5 molar equivalent, further preferably not less than 1 molar equivalent, relative to the protected organic compound. While the upper limit is not particularly limited, the amount of the precipitation promoter of the present invention to be used is preferably not more than 10 molar equivalents, more preferably not more than 5 molar equivalents, further preferably not more than 2.5 molar equivalents, relative to the protected organic compound, from the aspects of cost.

The amount of the polar solvent in solvents containing a polar solvent (preferably acetonitrile) is preferably not less than 0.5 mL, more preferably not less than 1 mL, further preferably not less than 2 mL, preferably not more than 20 mL, more preferably not more than 10 mL, further preferably not more than 8 mL, per 1 mL of a solvent other than the polar solvent, to increase the recovery rate of the protected organic compound. The amount of the polar solvent is a preferable range when a protected organic compound is precipitated. For example, a solution containing a protected organic compound and a solvent other than a polar solvent is concentrated, a polar solvent is added within the aforementioned range, and the organic compound may be precipitated. In addition, a solution containing a protected organic compound, a solvent other than a polar solvent and a polar solvent is prepared such that the amount of the polar solvent is not less than the aforementioned lower limit, and the solvent is concentrated to adjust the amount of the polar solvent to not less than the aforementioned lower limit, whereby the organic compound is precipitated.

The temperature of precipitation of the protected organic compound is preferably not less than −10° C., more preferably not less than 0° C., further preferably not less than 5° C., preferably not more than 40° C., more preferably not more than 30° C., further preferably not more than 25° C.

After adjusting to the aforementioned preferable temperature, the standing time (i.e., time for precipitation) of a suspension of the protected organic compound is preferably not less than 5 min, more preferably not less than 15 min, further preferably not less than 30 min, preferably not more than 72 hr, more preferably not more than 16 hr, further preferably not more than 3 hr.

Production Method of Oligonucleotide

The precipitation method of the present invention is particularly useful for the production method of oligonucleotide. Therefore, the present invention also provides a production method of oligonucleotide including the precipitation method of the present invention. Examples of such production method include a method containing steps of adding a polar solvent (preferably acetonitrile) to a reaction solution containing an oligonucleotide wherein at least one group is protected by the pseudo solid phase protecting group of the present invention and other group is optionally further protected by a protecting group used in nucleic acid synthesis, and the precipitation promoter of the present invention, and separating a precipitation mixture containing the oligonucleotide and the precipitation promoter from the reaction solution. The production method of oligonucleotide of the present invention is preferably performed by a phosphoramidite method.

A preferable embodiment of the production method of oligonucleotide of the present invention is a production method of oligonucleotide, comprising one repeat of a production cycle comprising the following steps (1) to (3), or plural repeats thereof by a phosphoramidite method, which comprises the following step (4) in the first cycle, the following step (5) in each cycle, and the following step (6) in each cycle except the final cycle:

(1) a step of obtaining a reaction solution comprising a free-5'-hydroxy-group form by adding an acid to a reaction solution comprising a nucleoside or oligonucleotide wherein at least one group selected from an amino group and an imino group of a nucleic acid base, 2'- and 3'-hydroxy groups of a ribose residue, and 3'-hydroxy group of a deoxyribose residue is protected by the pseudo solid phase protecting group of the present invention, a 5'-hydroxy group is protected by a temporary protecting group removable under acidic conditions, and other group is optionally further protected by a protecting group used in nucleic acid synthesis (hereinafter sometimes to be referred to as "temporary protecting group-containing nucleoside or oligonucleotide") in a nonpolar solvent, to deprotect the temporary protecting group of the 5'-hydroxy group, and neutralizing same with a base (deprotection step);

(2) a step of obtaining a reaction solution comprising a phosphite triester form, by adding nucleoside or oligonucleotide wherein a 3'-hydroxy group is phosphoramidited, a 5'-hydroxy group is protected by a temporary protecting group removable under acidic conditions, and other group is optionally further protected by a protecting group used in nucleic acid synthesis (hereinafter sometimes to be referred to as "phosphoramidited nucleoside or oligonucleotide") to the reaction solution comprising the free-5'-hydroxy-group form in a nonpolar solvent (condensation step);

(3) a step of obtaining a reaction solution comprising an oligonucleotide wherein at least one group selected from an amino group and an imino group of a nucleic acid base, 2'- and 3'-hydroxy groups of a ribose residue, and 3'-hydroxy group of a deoxyribose residue is protected by the pseudo solid phase protecting group of the present invention, a 5'-hydroxy group is protected by a temporary protecting group removable under acidic conditions, and other group is optionally further protected by a protecting group used in nucleic acid synthesis (hereinafter sometimes to be referred to as "resultant oligonucleotide"), by adding an oxidizing agent or a sulfurizing agent to the reaction solution comprising the phosphite triester form in a nonpolar solvent (oxidation or sulfurization step);

(4) a step of adding the precipitation promoter of the present invention to the reaction solution at any of before step (1), between steps (1) and (2), between steps (2) and (3) and after step (3) (precipitation promoter addition step);

(5) a step of separating a precipitation mixture comprising the free-5'-hydroxy-group form, the phosphite triester form or the oligonucleotide, and the precipitation promoter from the reaction solution by adding a polar solvent (preferably acetonitrile) to the reaction solution comprising the precipitation promoter at after step (4), and any of between steps (1) and (2), between steps (2) and (3) and after step (3) (precipitation and solid-liquid separation step)

(6) a step of adding a nonpolar solvent to the precipitation mixture obtained in step (5) to give a reaction solution (dissolution step).

Each step is explained below in the above order.

Step (1) (Deprotection Step)

In this step, the temporary protecting group is removed from the temporary protecting group-containing nucleoside or oligonucleotide by the addition of an acid to give free-5'-hydroxy-group form. Here, the temporary protecting group means a protecting group removable under acidic conditions in which the pseudo solid phase protecting group of the present invention is not removed.

This step is performed in a nonpolar solvent. As the nonpolar solvent, the aforementioned nonpolar solvents can be mentioned. The same applies to the nonpolar solvents to be used in the steps after this step.

While the concentration of the temporary protecting group-containing nucleoside or oligonucleotide in the solution m in this step is not particularly limited as long as it is dissolved in the solvent, it is preferably 1 to 30 wt %.

While the acid to be used in this step is not particularly limited as long as good deprotection can be achieved, trifluoroacetic acid, dichloroacetic acid, trifluoromethanesulfonic acid, trichloroacetic acid, methanesulfonic acid, hydrochloric acid, acetic acid, p-toluenesulfonic acid and the like are preferably used. Since good reaction can be achieved, trifluoroacetic acid, dichloroacetic acid, trifluoromethanesulfonic acid and trichloroacetic acid are more preferable, trifluoroacetic acid, dichloroacetic acid and trifluoromethanesulfonic acid are more preferable, trifluoroacetic acid and trifluoromethanesulfonic acid are still more preferable, and trifluoroacetic acid is particularly preferable. These acids may be diluted with the above-mentioned non-polar solvent. When the aforementioned acid is used, it may be combined with a particular base to appropriately adjust the acidity before use. The amount of the acid to be used in this step is, for example, 1 to 100 mol, preferably 1 to 40 mol, per 1 mol of temporary protecting group-containing nucleoside or oligonucleotide.

While the reaction temperature in this step is not particularly limited as long as the reaction proceeds, it is preferably −10° C. to 50° C., more preferably 0° C. to 40° C. The reaction time varies depending on the temporary protecting group-containing nucleoside or oligonucleotide to be used, the kind of acid and the kind of nonpolar solvent, reaction temperature and the like, it is, for example, 5 min to 5 hr.

To continuously perform this step, subsequent condensation step, and oxidation or sulfurization step in a solution, it is preferable to use a cation scavenger in this step during or after the removal reaction of a temporary protecting group of 5'-hydroxyl group in temporary protecting group-containing nucleoside or oligonucleotide.

While the cation scavenger is not particularly limited as long as re-protection (returning to starting material) with the removed temporary protecting group and side reaction with the deprotected functional group do not proceed, pyrrole derivatives such as pyrrole, 2-methylpyrrole, 3-methylpyrrole, 2,3-dimethylpyrrole, 2,4-dimethylpyrrole and the like; and indole derivatives such as indole, 4-methylindole, 5-methylindole, 6-methylindole, 7-methylindole, 5,6-dimethylindble, 6,7-dimethylindole and the like can be used. Since a good cation trap effect can be obtained, pyrrole, 3-methylpyrrole, 2,4-dimethylpyrrole, indole, 4-methylindole, 5-methylindole, 6-methylindole, 7-methylindole, 5,6-dimethylindole and 6,7-dimethylindole are preferable, pyrrole, 3-methylpyrrole and indole are more preferable, pyrrole and indole are further preferable, and pyrrole is particularly preferable. The amount of the cation scavenger to be used in this step is, for example, 1 to 50 mol, preferably 5 to 20 mol, per 1 mol of the temporary protecting group-containing nucleoside or oligonucleotide.

When the acid to be used as a deprotecting agent is present during the condensation step as the next step, it induces deprotection of the temporary protecting group of the phosphoramidited nucleoside or oligonucleotide used in step (2). This, the acid needs to be neutralized and removed.

In this step, an organic base is preferably used for neutralization of the acid. As the organic base, pyridine, 2,4,6-trimethylpyridine, benzimidazole, 1,2,4-triazole, N-phenylimidazole, 2-amino-4,6-dimethylpyrimidine, 1,10-phenanthrolin, imidazole, N-methylimidazole, 2-chlorobenzimidazole, 2-bromobenzimidazole, 2-methylimidazole, 2-phenylbenzimidazole, N-phenylbenzimidazole, 5-nitrobenzimidazole are preferable, pyridine, 2,4,6-trimethylpyridine, benzimidazole, 1,2,4-triazole, N-phenylimidazole, N-methylimidazole, 2-amino-4,6-dimethylpyrimidine, 1,10-phenanthrolin are more preferably, pyridine, 2,4,6-trimethylpyridine, benzimidazole, 1,2,4-triazole, N-phenylimidazole are further preferable, pyridine, 2,4,6-trimethylpyridine, benzimidazole, 1,2,4-triazole are particularly preferable, and pyridine, 2,4,6-trimethylpyridine, benzimidazole are most preferable.

The amount of the base to be used in this step is, for example, 1 to 10 mol, preferably 1 to 3 mol, per 1 mol of acid.

A particularly preferable combination of acid and organic base in this step is trifluoroacetic acid and pyridine, trifluoroacetic acid and 2,4,6-trimethylpyridine or trifluoromethanesulfonic acid and benzimidazole.

The temporary protecting group contained in the temporary protecting group-containing nucleoside or oligonucleotide to be used in this step is not particularly limited as long as deprotection is possible under acidic conditions and it can be used as a hydroxy-protecting group. For example, trityl group, 9-(9-phenyl)xanthenyl group, 9-phenylthioxanthenyl group, di($C_{1-6}$ alkoxy)trityl groups such as 1,1-bis(4-methoxyphenyl)-1-phenylmethyl group (dimethoxytrityl group) and the like, mono ($C_{1-18}$ alkoxy)trityl groups such as 1-(4-methoxyphenyl)-1,1-diphenylmethyl group (monomethoxytrityl group) and the like, and the like can be mentioned. Of these, the temporary protecting group is preferably a monomethoxytrityl group or a dimethoxytrityl group, more preferably a dimethoxytrityl group, from the aspects of easy deprotection and easy availability.

In the temporary protecting group-containing nucleoside or oligonucleotide to be used in this step, at least one group selected from amino group and imino group of nucleic acid base, 3'-hydroxy group of ribose residue, and 3'-hydroxy group of deoxyribose residue is preferably protected by the pseudo solid phase protecting group of the present invention, and 3'-hydroxy group of ribose residue or 3'-hydroxy group of deoxyribose residue is more preferably protected by the pseudo solid phase protecting group of the present invention.

The temporary protecting group-containing nucleoside or oligonucleotide to be used in this step is further preferably a m compound represented by the following formula (VI).

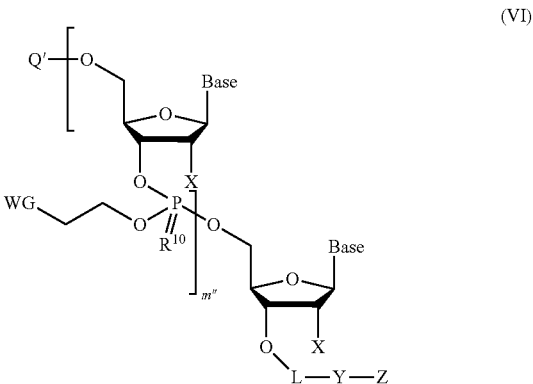

(VI)

wherein m" is an integer of not less than 0,

Base in the number of m"+1 are each independently an optionally protected nucleic acid base, Q' is a temporary protecting group removable under acidic conditions, X in the number of m"+1 are each independently a hydrogen atom, a halogen atom, an optionally protected hydroxy group, or a divalent organic group that binds to the 2-position carbon atom and 4-position carbon atom of a ribose ring or a deoxyribose ring (preferably a hydrogen atom, a halogen atom or an optionally protected hydroxy group), $R^{10}$ in the number of m" are each independently an oxygen atom or a sulfur atom, WG in the number of m" are each independently an electron-withdrawing group, and L-Y—Z is as defined above.

When m" is 0, compound (VI) is a temporary protecting group-containing nucleoside, and when m" is one or more, compound (VI) is a temporary protecting group-containing oligonucleotide. In the formula (VI), m" is preferably not more than 49, more preferably not more than 29, further preferably not more than 19, particularly preferably not more than 4, most preferably not more than 2.

As the halogen atom in the formula (VI), a fluorine atom or a chlorine atom is preferable, and a fluorine atom is more preferable.

While the protecting group of the "optionally protected hydroxy group" in the formula (VI) is not particularly limited, for example, any protecting group described in PROTECTIVE GROUPS IN ORGANIC SYNTHESIS, 3rd ed., JOHN WILLY&SONS (1999) and the like can be mentioned. Specifically, methyl group, benzyl group, p-methoxybenzyl group, tert-butyl group, methoxymethyl group, methoxyethyl group, 2-tetrahydropyranyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, trimethylsilyl group, triethylsilyl group, triisopropylsilyl group, tert-butyldimethylsilyl group, [(triisopropylsilyl)oxy]methyl (Tom) group, 1-(4-chlorophenyl)-4-ethoxypiperidin-4-yl (Cpep) group and the like can be mentioned. Among these, triethylsilyl group, triisopropylsilyl group and tert-butyldimethylsilyl group are preferable. From the aspects of economic efficiency and easy availability, tert-butyldimethylsilyl group is particularly preferable.

In the formula (VI), the "divalent organic group that binds to the 2-position carbon atom and 4-position carbon atom of a ribose ring or a deoxyribose ring" is not particularly limited as long as it binds to the 2-position carbon atom and 4-position carbon atom on the same ribose ring or deoxyribose ring. Examples of the divalent organic group include an optionally substituted $C_{2-7}$ alkylene group, as well as a divalent organic group formed from a divalent linker selected from —O—, —NR$^{13}$— (R$^{13}$ is a hydrogen atom or a $C_{1-6}$ alkyl group), —S—, —CO—, —COO—, —OCONR$^{14}$— (R$^{14}$ is a hydrogen atom or a $C_{1-6}$ alkyl group) and —CONR$^{15}$— (R$^{15}$ is a hydrogen atom or a $C_{1-6}$ alkyl group) and an optionally substituted $C_{1-7}$ alkylene group, and the like. Examples of the substituent that the $C_{1-7}$ alkylene group and the $C_{2-7}$ alkylene group optionally have include a methylidene group ($CH_2$=).

As the "divalent organic group that binds to the 2-position carbon atom and 4-position carbon atom", an optionally substituted $C_{2-7}$ alkylene group, —ORi- (Ri is a $C_{1-6}$ alkylene group that binds to the 4-position carbon atom), —O—NR$^{13}$—Rj- (Rj is a $C_{1-6}$ alkylene group that binds to the 4-position carbon atom and R$^{13}$ is as defined above), —O—Rk-O—Rl- (Rk is a $C_{1-6}$ alkylene group, and Rl is a $C_{1-6}$ alkylene group that binds to and crosslinks with the 4-position carbon atom) are preferable, and —ORi- (Ri is as defined above), —O—NR$^{13}$—Rj- (Rj and R$^{13}$ are as defined above), —O—Rk-O—Rl- (Rk and Rl are as defined above) are more preferable. The $C_{1-6}$ alkylene group for Ri, Rj, Rk or Rl is each independently preferably a methylene group or an ethylene group.

As the "divalent organic group that binds to the 2-position carbon atom and 4-position carbon atom, —O—$CH_2$—, —O—$CH_2$—$CH_2$—, —O—NR$^{13}$—$CH_2$— (R$^{13}$ is as defined above), —O—$CH_2$—O—$CH_2$— are more preferable, and —O—$CH_2$—, —O—$CH_2$—$CH_2$—, —O—NH—$CH_2$—, —O—N($CH_3$)—$CH_2$—, —O—$CH_2$—O—$CH_2$— (wherein the left side binds to the 2-position carbon atom, and the right side binds to the 4-position carbon atom) are further preferable.

In the formula (VI), X in the number of m"+1 are each independently preferably a hydrogen atom, a halogen atom, or an optionally protected hydroxy group, more preferably a hydrogen atom or an optionally protected hydroxy group.

R$^{10}$ in the number of m" are each preferably an oxygen atom.

Examples of the electron-withdrawing group for WG include a cyano group, a nitro group and the like, preferably a cyano group.

Compound (VI) can be synthesized by a method known per se (e.g., the method described in the aforementioned patent document 1 or 2, esterification, silylation etc.) or a method analogous thereto. For example, compound (VI) wherein m" is 0 and L is a succinyl group can be synthesized by, for example, as shown in the following formula, reacting nucleoside (a) wherein 5'-hydroxyl group is protected by a temporary protecting group with succinic anhydride in the presence of a base to give compound (b) wherein succinic acid is introduced into 3'-hydroxyl group, and dehydration condensation of compound (b) with Z—Y—H in the presence of a condensing agent.

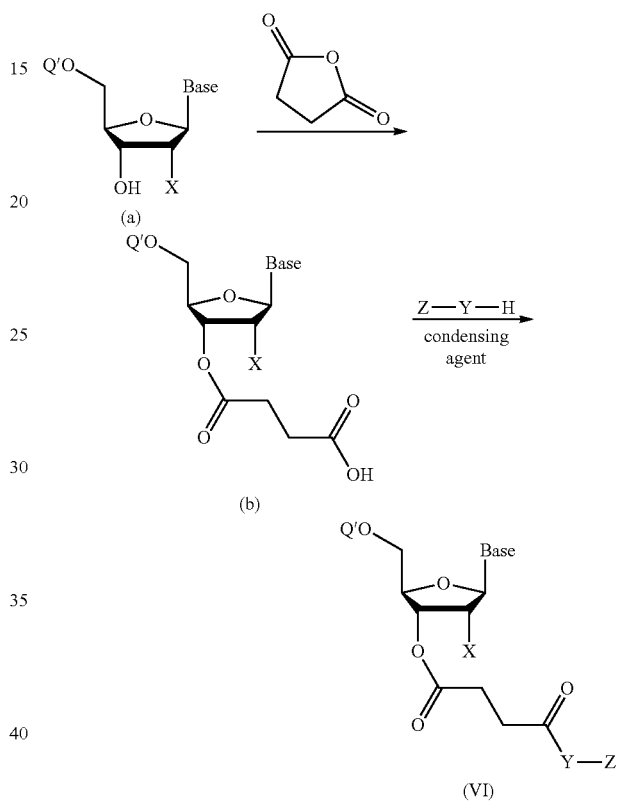

The conversion reaction of nucleoside (a) to compound (b) is advantageously performed in a solvent inert to the reaction. While such solvent is not particularly limited as long as the reaction proceeds, halogenated solvents such as dichloromethane, 1,2-dichloroethane, chloroform, carbon tetrachloride and the like, aromatic solvents such as benzene, toluene, xylene and the like, aliphatic solvents such as pentane, hexane, heptane, octane and the like, ether solvents such as diethylether, tetrahydrofuran, cyclopentyl methyl ether and the like, and mixed solvents thereof are preferable. Of these, dichloromethane and chloroform are particularly preferable.

While the base to be used for the synthesis of compound (VI) is not particularly limited, an organic base is preferable, and triethylamine is more preferable.

The dehydration condensation reaction for the synthesis of compound (VI) is advantageously performed in a solvent inert to the reaction. While such solvent is not particularly limited as long as the reaction proceeds, halogenated solvents such as dichloromethane, 1,2-dichloroethane, chloroform, carbon tetrachloride and the like, aromatic solvents such as benzene, toluene, xylene and the like, or aliphatic solvents such as pentane, hexane, heptane, octane and the like, and a combination thereof are preferable. Of these, dichloromethane and chloroform are particularly preferable.

Examples of the condensing agent used for the condensation reaction of compound (b) with Z—Y—H include dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy) tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like. Of these, HBTU, HCTU, N-ethyl-N'-3-dimethylaminopropylcarbodiimide and hydrochloride thereof (EDC HCl) are preferable.

The amount of the condensing agent to be used is, for example, 1 to 10 mol, preferably 1 to 5 mol, per 1 mol of compound (b). The amount of Z—Y—H to be used is 1 to 10 mol, preferably 1 to 5 mol, per 1 mol of compound (b). While the reaction temperature is not particularly limited as long as the reaction proceeds, it is preferably −10° C. to 50° C., more preferably 0° C. to 30° C. The reaction time is for example, 30 min to 70 hr.

Compound (VI) wherein L is other than a succinyl group can also be synthesized by performing a reaction similar to the above-mentioned synthesis method except that a corresponding acid anhydride, a corresponding dicarboxylic acid halide, an activated ester of corresponding dicarboxylic acid and the like is used instead of succinic anhydride. Also, compound (VI) wherein m" is one or more can be synthesized by repeating 5'-terminus elongation process by using compound (VI) wherein m" is 0 as a starting material.

Step (2) (Condensation Step)

In this step, the free-5'-hydroxy-group form obtained in step (1) and phosphoramidited nucleoside or oligonucleotide are condensed to give a phosphite triester form.

The phosphoramidited nucleoside or oligonucleotide to be used in this step can be synthesized by a known method (M. H. Caruthers et al., Method in Enzymology 1987, 154, 287-313; S. L. Beaucage and M. H. Caruthers, Tetrahedron Letters 1981, 22, 1859-1862, which are incorporated herein by reference in their entireties), including reacting a phosphoramiditing reagent. A phosphoramidite reagent is commercially available and can be obtained easily.

The phosphoramidited nucleoside or oligonucleotide to be used in this step is preferably a compound represented by the following formula (VII):

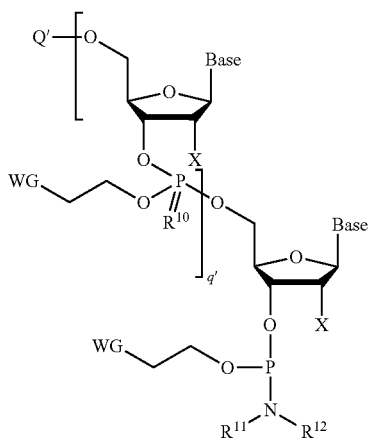

(VII)

wherein
q' is an integer of not less than 0,
$R^{11}$ and $R^{12}$ are each independently an alkyl group, or a 5- or 6-membered saturated cyclic amino group formed together with the adjacent nitrogen atom. The saturated cyclic amino group optionally has one oxygen atom or sulfur atom as a ring-constituting atom besides nitrogen atom, and other symbols are as defined above.

When q' is 0, compound (VII) is phosphoramidited nucleoside, when q' is one or more, compound (VII) is phosphoramidited oligonucleotide. In compound (VII) to be used in this step, q' is preferably not more than 49, more preferably not more than 29, further preferably not more than 19, particularly preferably not more than 4, and most preferably not more than 2.

When the condensation reaction in this step proceeds slowly, a condensing agent (e.g., pyridine.trifluoroacetate, tetrazole, 5-benzylthio-1H-tetrazole, 4,5-dicyanoimidazole etc.) may be added.

In this step, when the acidity of the reaction solution becomes high, a side reaction removing temporary protecting group may occur. Therefore, N-methylimidazole is preferably added to suppress acidification of the reaction solution. The amount of N-methylimidazole to be added to adjust the acidity is preferably 0.1 to 1 mol, more preferably 0.5 mol, per 1 mol of the organic base used for neutralization.

Similar to step (1), this step is performed in a nonpolar solvent. The explanation on the nonpolar solvent is the same as that in step (1).

The amount of the phosphoramidited nucleoside or oligonucleotide to be used in this step is, for example, 1 to 10 mol, preferably 1 to 5 mol, per 1 mol of the free-5'-hydroxy-group form obtained in step (1).

While the reaction temperature in this step is not particularly limited as long as the reaction proceeds, 0° C. to 100° C. is preferable, and 20° C. to 50° C. is more preferable. While the reaction time varies depending on the kind of the material to be used, the reaction temperature and the like, it is, for example, 5 min to 24 hr.

Step (3) (Oxidation or Sulfurization Step)

In this step, the phosphite triester form obtained in step (2) is reacted with an oxidizing agent or sulfurizing agent to convert the phosphite triester bond thereof to a phosphate triester bond or a thiophosphate triester bond to give the resultant oligonucleotide.

While the "oxidizing agent" to be used in this step is not particularly limited as long as it can oxidize a phosphite triester bond into a phosphate triester bond without oxidizing other moieties, iodine, (1S)-(+)-(10-camphorsulfonyl)-oxaziridine, tert-butyl hydroperoxide (TBHP), 2-butanone peroxide, 1,1-dihydroperoxycyclododecane, bis(trimethylsilyl)peroxide or m-chloroperbenzoic acid is preferably used. Since good oxidation reaction can be achieved, iodine, (1S)-(+)-(10-camphorsulfonyl)oxaziridine, tert-butyl hydroperoxide, 2-butanone peroxide and 1,1-dihydroperoxycyclododecane are more preferable, iodine, (1S)-(+)-(10-camphorsulfonyl)oxaziridine, tert-butyl hydroperoxide and 2-butanone peroxide are further preferable, iodine and tert-butyl hydroperoxide are still more preferable, and iodine is particularly preferable. The oxidizing agent can be used after diluting with a suitable solvent to achieve a concentration of 0.05 to 2M. While the dilution solvent is not particularly limited as long as it is inert to the reaction, pyridine, THF, dichloromethane, water and a combination of these can be mentioned. Among them, for example, iodine/ water/pyridine-THF or iodine/pyridine-acetic acid, peroxide (TBHP)/dichloromethane or tert-butyl hydroperoxide/nonane is preferably used.

The sulfurizing agent to be used in this step is not particularly limited as long as it can convert a phosphite triester bond to a thiophosphate triester bond, 3-[(N,N-dimethylaminomethylidene)amino]-3H-1,2,4-dithiazole-5-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), 3-amino-1,2,4-dithiazole-5-thione (ADTT) or sulfur is preferably used. Since a good reaction proceeds, 3-[(N,N-dimethylaminomethylidene)amino]-3H-1,2,4-dithiazole-5-thione (DDTT), 3H-1,2-benzodithiol-3-one-1,1-dioxide (Beaucage reagent), 3H-1,2-benzodithiol-3-one and phenylacetyl disulfide (PADS) are more preferable, 3-[(N,N-dimethylaminomethylidene)amino]-3H-1,2,4-dithiazole-5-thione and 3H-1,2-benzodithiol-3-one-1,1-dioxide are further preferable, and 3-[(N,N-dimethylaminomethylidene)amino]-3H-1,2,4-dithiazole-5-thione is particularly preferable. The sulfurizing agent can be used after diluting with a suitable solvent to achieve a concentration of 0.05 to 2M. While the dilution solvent is not particularly limited as long as it is inert to the reaction, for example, dichloromethane, acetonitrile, pyridine and a mixed solvent of any of them can be mentioned.

The amount of the oxidizing agent or sulfurizing agent to be used is for example 1 to 50 mol, preferably 1 to 5 mol, per 1 mol of the phosphite triester form obtained in step (2).

While the reaction temperature is not particularly limited as long as the reaction proceeds, 0° C. to 100° C. is preferable, and 20° C. to 50° C. is more preferable. While the reaction time varies depending on the kind of phosphite triester form, the kind of oxidizing agent or sulfurizing agent to be used, the reaction temperature and the like, it is 1 min to 3 hr.

Step (4) (Precipitation Promoter Addition Step)

In this step, the precipitation promoter of the present invention is added to the reaction solution before step (5) and at any of before step (1), between step (1) and step (2), between step (2) and step (3), and after step (3), to promote precipitation in step (5) (precipitation and solid-liquid separation step) of separating precipitated oligonucleotide from the reaction solution by adding a polar solvent (preferably acetonitrile) to the reaction solution at any of between step (1) (deprotection step) and step (2) (condensation step), between step (2) and step (3) (oxidation or sulfurization step), and after step (3).

In this step, only one kind of the precipitation promoter of the present invention may be added, or two or more kinds thereof may be added. The amount of the precipitation promoter of the present invention to be used in this step is preferably not less than 0.1 molar equivalent, more preferably not less than 0.5 molar equivalent, further preferably not less than 1 molar equivalent, relative to the temporary protecting group-containing nucleoside or oligonucleotide used in the initial step (1). While the upper limit is not particularly limited, the amount of the precipitation promoter of the present invention to be used is preferably not more than 10 molar equivalents, more preferably not more than 5 molar equivalents, further preferably not more than 2.5 molar equivalents, relative to the temporary protecting group-containing nucleoside or oligonucleotide used in the initial step (1), from the aspects of cost.

Step (5) (Precipitation and Solid-Liquid Separation Step)

In this step, at any of after step (4) (precipitation promoter addition step), between step (1) (deprotection step) and step (2) (condensation step), between step (2) and step (3) (oxidation or sulfurization step), and after step (3), a polar solvent (preferably acetonitrile) is added to the reaction solution containing a precipitation promoter, to separate a precipitation mixture containing the free-5'-hydroxy-group form obtained in step (1), the phosphite triester form obtained in step (2), or the resultant oligonucleotide obtained in step (3) (hereinafter free-5'-hydroxy-group form, phosphite triester form and resultant oligonucleotide are sometimes to be collectively referred to as "the object product") and the precipitation promoter, from the reaction solution.

As the polar solvent, the aforementioned polar solvent can be mentioned. As the polar solvent to be used in this step, acetonitrile is particularly preferable.

To increase the recovery rate of the object product, the amount of the polar solvent (preferably acetonitrile) to be added in this step is preferably not less than 0.5 mL, more preferably not less than 1 mL, further preferably not less than 2 mL, preferably not more than 20 mL, more preferably not more than 10 mL, further preferably not more than 8 mL, per 1 mL of the nonpolar solvent contained in the reaction solution containing the object product.

When acetonitrile is used, it may contain water to minimize the loss of the object product in acetonitrile. In this case, the content of water in acetonitrile is preferably 1 to 10% (v/v), more preferably 3 to 8% (v/v). When the water content is too low, the loss of the object product in acetonitrile tends to increase, and when the water content is too high, removal of unnecessary substances into acetonitrile tends to be insufficient.

Step (6) (Dissolution Step)

In this step, a nonpolar solvent is added to the precipitation mixture obtained in step (5) (precipitation and solid-liquid separation step) to give a reaction solution. In this step, a production cycle composed of the above-mentioned steps (1) to (3) can be repeated.

The explanation on the nonpolar solvent usable in this step is the same as that in step (1). While the concentration of the precipitation mixture in the reaction solution obtained in this step is not particularly limited as long as the precipitation mixture is dissolved in the nonpolar solvent, it is preferably 1 to 30 wt %.

In the production method of oligonucleotide of the present invention, step (5) (precipitation and solid-liquid separation step) and step (6) (dissolution step) are preferably performed after step (3) (oxidation or sulfurization step).

The production method of oligonucleotide of the present invention may contain the following step (7):

(7) a step of removing all protecting groups of the oligonucleotide and isolating the oligonucleotide (hereinafter sometimes to be referred to as "non-protected oligonucleotide") (deprotection and isolation step).

Step (7) (Deprotection and Isolation Step)

In the production method of oligonucleotide of the present invention, deprotection is performed preferably after step (5) according to the kind and properties of the protecting group, and oligonucleotide is isolated. All protecting groups can be removed from oligonucleotide, for example according to the deprotection method described in PROTECTIVE GROUPS IN ORGANIC SYNTHESIS, 3rd ed., JOHN WILLY&SONS (1999), which is incorporated herein by reference in its entirety, and the like. To be specific, the pseudo solid phase protecting group of the present invention, as well as the protecting group of nucleic acid base such as phenoxyacetyl group, acetyl group and the like, and cyanoethyl group protecting the phosphoric acid skeleton and the like can all be removed by a treatment with aqueous ammonia, aqueous ammonia/ethanol solution, or a mixture of aqueous ammonia and aqueous methylamine solution. In addition, 5' hydroxy-protecting group can be removed by a treatment with the acid used in step (1) or an appropriately diluted solution of such acid. Since oligonucleotide without a protecting group is easily degraded by an enzyme, oligonucleotide is preferably isolated under appropriate air contamination control.

The progress of the reaction in each of the above-mentioned steps can be confirmed by a method similar to conventional liquid phase organic synthesis reaction. That is, the reaction can be traced by thin layer silica gel chromatography, high performance liquid chromatography and the like.

The free-5'-hydroxy-group form, phosphite triester form or resultant oligonucleotide obtained in step (5) (precipitation and solid-liquid separation step), or the non-protected oligonucleotide obtained in step (7) (deprotection and isolation step) can also be led to a desired derivative by further subjecting to an organic synthesis reaction. The oligonucleotide etc. produced by the present invention can be used for various applications such as various medicaments for human or animal (RNA, DNA, oligonucleic acid medicament etc.), foods (functional food, food for specified health uses etc.), chemicals, biological or industrial polymer materials and the like.

Other features of the invention will become apparent in the course of the following descriptions of exemplary embodiments which are given for illustration of the invention and are not intended to be limiting thereof.

EXAMPLES

The solvent ratios described below show volume ratio unless specifically indicated. The reagents, apparatuses and materials used in the present invention are commercially available unless otherwise specified. In the present specification, when indicated by abbreviation such as amino acid etc., each indication is based on the abbreviation of the IUPAC-IUB Commission on Biochemical Nomenclature or conventional abbreviations in the art.

The abbreviations of groups and compounds used in Example and the like are as follows.

Me: methyl group

DMTr: 4,4'-dimethoxytrityl group

TBDMS: t-butyldimethylsilyl group

Boc: t-butoxycarbonyl group

Pbf: 2,2,4,6,7-pentamethyldihydrobenzofuran-5-sulfonyl

Trt: trityl group

TOB: 3,4,5-tri(octadecyloxy)benzyl group

DMF: N,N-dimethylformamide

HBTU: O-(benzotriazol-1-yl)-N,N,N',N'-tetramethyluronium hexafluorophosphate

Reference Example 1: Continuous Synthesis of Phosphorthioate Dimer in Solution

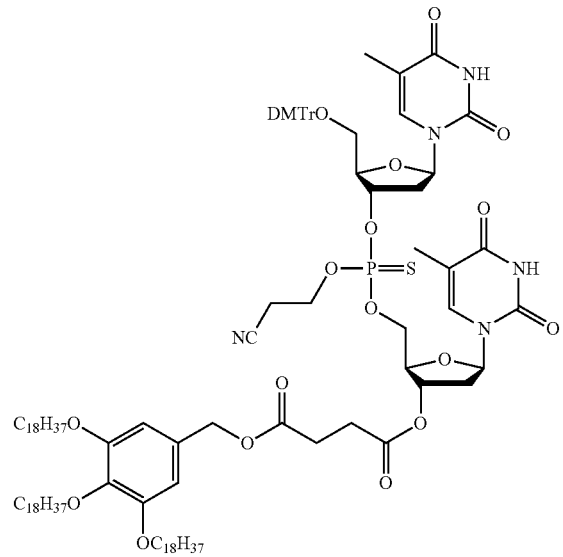

Under an argon atmosphere, 5'-O-(4,4'-dimethoxytrityl) deoxythymidine-3'-yl [3,4,5-tri(octadecyloxy)benzyl]succinate (504 mg, 327 µmol) was dissolved in dichloromethane (7.5 mL), pyrrole (213 µL, 3.27 mmol), trifluoroacetic acid (292 µL, 3.93 mmol) were added and the mixture was stirred at room temperature for 15 min, and completion of the reaction was confirmed by thin layer chromatography. The reaction mixture was neutralized with pyridine (316 µL, 3.93 mmol), 1-methylimidazole (156 µL, 1.96 mmol), a solution of 4,5-dicyanoimidazole (116 mg, 982 mmol), 5'-O-(4,4'-dimethoxytrityl)deoxythymidine-3'-[O-(2-cyanoethyl)-(N,N-diisopropyl)]-phosphoramidite (609 mg, 818 µmol) in acetonitrile was added, and the mixture was stirred at room temperature for 60 min, and completion of the reaction was confirmed by thin layer chromatography. Furthermore, 3-[(N,N-dimethylaminomethylidene)amino]-3H-1,2,4-dithiazole-5-thione (184 mg, 898 µmol) was added and the mixture was stirred at room temperature for 30 min. Methanol (100 mL) was added to the reaction solution, and the precipitated solid was suction-filtered using Kiriyama funnel and dried to give 5'-O-(4,4'-dimethoxytrityl)deoxythymidine-3'-[O-(2-cyanoethyl)]phosphorothionyl deoxythymidine-3'-yl [3,4,5-tri(octadecyloxy)benzyl] succinate (567 mg, yield 91%) as a white solid.

$^1$H-NMR (400 MHz, CDCl$_3$): δ=0.88 (t, 9H, J=6.8 Hz, Ar—C$\underline{H}_3$), 1.28 (br, s, 90H, (C$\underline{H}_2$)$_{15}$), 1.30 (s, 3H, N$_1^5$—C$\underline{H}_3$), 1.46 (s, 3H, N$_2^5$—C$\underline{H}_3$) 1.73 (m, 6H, Ar—OCH$_2$C$\underline{H}_2$), 2.28 (m, 2H, 2'$_1$—$\underline{H}$), 2.41 (m, 2H, 2'2—$\underline{H}$), 2.68 (m, 2H, 5'$_1$—$\underline{H}$ and m, 4H, succinyl-C$\underline{H}_2$C$\underline{H}_2$), 3.44 (m, 2H, 5'$_2$—$\underline{H}$), 3.79 (s, 6H, DMTr-OC$\underline{H}_3$), 3.95 (m, 6H, Ar—OC$\underline{H}_2$), 4.10 (m, 1H, 4'$_1$—$\underline{H}$), 4.31 (m, 4H, cyanoethyl-C$\underline{H}_2$CH$\underline{H}_2$ and m, 1H, 4'$_2$—$\underline{H}$), 5.01 (s, 2H, Ar—C$\underline{H}_2$-succinyl), 5.26 (m, 1H, 3'3,1H), 5.32 (m, 1H, 3'$_2$—$\underline{H}$), 6.27 (m, 1H, 1'$_1$—$\underline{H}$), 6.38 (m, 1H, 1'$_2$—$\underline{H}$), 6.53 (s, 2H, Ar—$\underline{H}$), 6.84-7.29 (m, 13H, DMTr-Ar—$\underline{H}$), 7.29 (m, 1H, N$_1^6$—$\underline{H}$), 7.56 (m, 1H, N$_2^6$—$\underline{H}$)

$^1$H-NMR (400 MHz, CDCl$_3$): δ=0.88 (t, 9H, Ar—C$\underline{H}_3$), 1.28 (br, s, 90H, (C$\underline{H}_2$)$_{15}$), 1.30 (s, 3H, N$_1^5$—C$\underline{H}_3$), 1.46 (s, 3H, N$_2^5$—C$\underline{H}_3$), 1.73 (m, 6H, Ar—OCH$_2$C$\underline{H}_2$), 2.41 (m, 2H, 2'$_2$-H), 2.68 (m, 2H, 2'$_1$-H and m, 4H, succinyl-CH$_2$CH$_2$), 2.77 (m, 2H, 5'$_1$—H), 3.44 (m, 2H, 5'$_2$—H), 3.79 (s, 6H, DmTr-OCH$_3$), 3.95 (m, 6H, Ar—OCH$_2$), 4.17 (m, 1H, 4'$_1$-H), 4.31 (m, 4H, cyanoethyl-CH$_2$CH$_2$ and m, 1H, 4'$_2$—H), 5.01 (s, 2H, Ar—CH$_2$-succinyl), 5.33 (m, 1H, 3'$_1$—H and m, 1H, 3'$_2$-H), 6.27 (m, 1H, 1'$_1$-H), 6.38 (m, 1H, 1'$_2$-H), 6.53 (s, 2H, Ar—H), 6.84-7.29 (m, 13H, DMTr-Ar—H), 7.29 (m, 1H, N$_1^6$—H), 7.56 (m, 1H, N$_2^6$—H)

Reference Example 2: Continuous Synthesis of Phosphorthioate Pentamer in Solution Operations similar to those of Reference Example 1 were repeated 4 times to give 5'-O-(4,4-dimethoxytrityl)-N$^2$-isobutyryl-deoxyguanosine 3'-[O-(2-cyanoethyl)]phosphorothionyl-N$^4$-benzoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidine-3'-yl [3,4,5-tri(octadecyloxy)benzyl] succinate (1.94 g).

Reference Example 3: Continuous Synthesis of Phosphorthioate Decamer in Solution Operations similar to those of Reference Example 1 were repeated 9 times to give 5'-O-(4,4'-dimethoxytrityl)-N$^2$-isobutyryl-deoxyguanosine 3'-[O-(2-cyanoethyl)]phosphorothionyl-N$^6$-benzoyl-deoxyadenosine 3'-[O-(2-cyanoethyl)]phosphorothionyl-N$^4$-benzoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O—(2-cyanoethyl)]phosphorothionyl-N$^2$-isobutyryl-deoxyguanosine 3'-[O-(2-cyanoethyl)]phosphorothionyl-N$^4$-benzoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidine 3'-yl 3,4,5-tri(octadecyloxy)benzyl succinate (1.41 g).

Reference Example 4: Continuous Synthesis of Phosphorthioate Icosamer in Solution Operations similar to those of Reference Example 1 were repeated 19 times to give 5'-O-(4,4'-dimethoxytrityl)-deoxythymidine 3'-[O-(2-cyanoethyl)]phosphorothionyl-N$^4$-benzoyl-deoxycytidine 3'-[O-(2-cyanoethyl)]phosphorothionyl-N$^4$-benzoyl-deoxycytidine 3'-[O-(2-cyanoethyl)]phosphorothionyl-N$^4$-benzoyl-deoxycytidine 3'-[O-(2-cyanoethyl)]phosphorothionyl-N$^2$-isobutyryl-deoxyguanosine 3'-[O-(2-cyanoethyl)]phosphorothionyl-N$^4$-benzoyl-deoxycytidine 3'-[O-(2-cyanoethyl)]phosphorothionyl-N$^4$-benzoyl-deoxycytidine 3'-[O-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-N$^6$-benzoyl-deoxyadenosine 3'-[O-(2-cyanoethyl)]phosphorothionyl-N$^4$-benzoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-N$^2$-isobutyryl-deoxyguanosine 3'-[O-(2-cyanoethyl)]phosphorothionyl-N$^4$-benzoyl-deoxycytidine 3'-[O-(2-cyanoethyl)]phosphorothionyl-N$^6$-benzoyl-deoxyadenosine 3'-[O-(2-cyanoethyl)]phosphorothionyl-deoxythymidine 3'-[O-(2-cyanoethyl)]phosphorothionyl-deoxythymidine 3'-yl 3,4,5-tri(octadecyloxy)benzyl succinate (1.61 g).

Comparative Example 1: Synthesis of Methyl 3,4,5-tri(16-methylheptadecan-1-yloxy)benzoate (1) Synthesis of 16-methylheptadecan-1-yl bromide

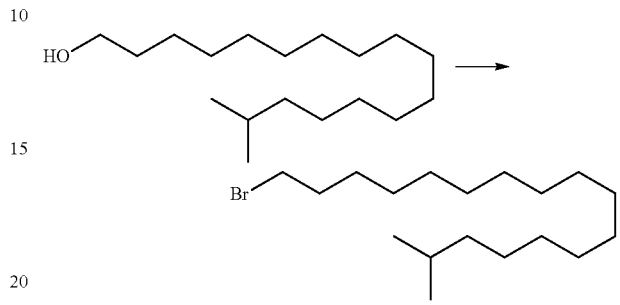

16-Methylheptadecan-1-yl alcohol (5.00 g, 18.5 mmol) was dissolved in hydrobromic acid (50 mL), concentrated sulfuric acid (84 µL, 1.59 mmol) was added, and the mixture was stirred at 100° C. for 16 hr. Completion of the reaction was confirmed by thin layer chromatography, the reaction solution was cooled to room temperature, and hexane (150 mL) was added. The reaction solution was washed twice with saturated aqueous sodium hydrogen carbonate solution (100 mL) and once with saturated brine (50 mL). The organic layer was dried over magnesium sulfate, and purified by short silica gel column chromatography (hexane) to give the object compound (5.56 g, yield 90%).

(2) Synthesis of Methyl 3,4,5-tri(16-methylheptadecan-1-yloxy)benzoate

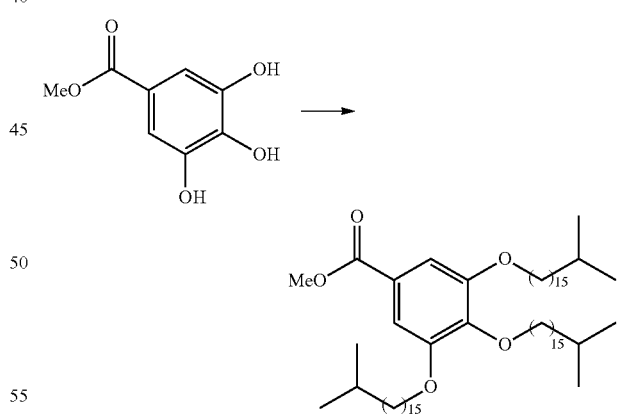

Methyl 3,4,5-trihydroxybenzoate (1.03 g, 5.57 mmol), 16-methyl-heptadecanyl bromide (5.56 g, 16.7 mmol), potassium carbonate (3.85 g, 27.9 mmol) were dissolved in N,N-dimethylformamide (50.0 mL), and the mixture was stirred at 110° C. for 16 hr. Completion of the reaction was confirmed by thin layer chromatography, the reaction solution was cooled to room temperature, and ethyl acetate (200 mL) was added. The organic layer was washed twice with water (100 mL), once with saturated aqueous sodium hydrogen carbonate solution (100 mL), and once with saturated brine (100 mL), dried over sodium sulfate, and concentrated under reduced pressure to give the object compound (4.66 g, yield 88%).

$^1$H-NMR (400 MHz, CDCl$_3$): δ=0.83-0.90 (m, 18H, —CH$_3$), 1.05-1.51 (m, 81H, —O—CH$_2$—CH$_2$—(CH$_2$)$_{13}$—CH(CH$_3$)$_2$), 1.70-1.84 (m, 6H, —O—CH$_2$—CH$_2$—(CH$_2$)$_{13}$—CH(CH$_3$)$_2$), 3.88 (s, 3H, C(O) OCH$_3$), 3.99-4.02 (m, 6H, Ar—OCH$_2$), 7.25 (s, 2H, Ar—H)

Comparative Example 2: Synthesis of Methyl 4-octadecyloxybenzoate

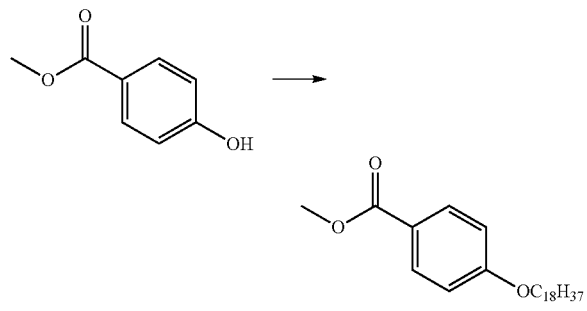

Under an argon atmosphere, potassium carbonate (2.72 g, 19.7 mmol), methyl 4-hydroxybenzoate (1.00 g, 6.57 mmol), 1-bromooctadecane (2.63 g, 7.88 mmol) were dissolved in N,N-dimethylformamide (60 mL), and the mixture was stirred at 90° C. for 16 hr. Completion of the reaction was confirmed by thin layer chromatography, ethyl acetate (100 mL) and tetrahydrofuran (20 mL) were added to the reaction solution, and the organic layer was washed 3 times with water (100 mL), and once with saturated brine (100 mL). The organic layer was evaporated under reduced pressure. To the concentrated residue was added ethyl acetate (50 mL), and the mixture was dissolved by heating to 70° C. and cooled to 5° C. to give the object compound (2.61 g, yield 98%).

$^1$H-NMR (400 MHz, CDCl$_3$): δ=0.88 (t, 3H, J=6.8 Hz, —CH$_2$CH$_2$(CH$_2$)$_{15}$CH$_3$), 1.26-1.49 (m, 30H, —CH$_2$CH$_2$(CH$_2$)$_{15}$CH$_3$), 1.76-1.83 (m, 2H, —CH$_2$CH$_2$(CH$_2$)$_{15}$CH$_3$), 3.88 (s, 3H, —C(O)OCH$_3$), 4.00 (t, 2H, J=6.4 Hz, —CH$_2$CH$_2$(CH$_2$)$_{15}$CH$_3$) 6.90 (d, 2H, J=9.2 Hz, Ar—H), 7.98 (d, 2H, J=9.2 Hz, Ar—H)

Example 1: Synthesis of Methyl 3,5-bis(octadecyloxy)benzoate

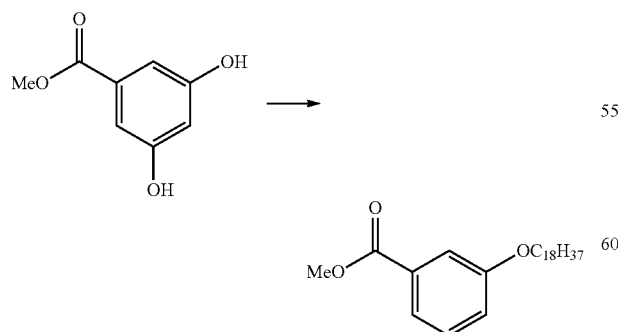

Under an argon atmosphere, potassium carbonate (19.9 g, 144 mmol), methyl 3,5-dihydroxybenzoate (3.60 g, 21.4 mmol), 1-bromooctadecane (15.5 g, 46.7 mmol) were dissolved in N,N-dimethylformamide (200 mL), and the mixture was stirred at 70° C. for 16 hr. Completion of the reaction was confirmed by thin layer chromatography, the reaction solution was poured into water (800 mL) to allow for precipitation to give a solid. The obtained solid was dissolved in dichloromethane (200 mL), the solid was precipitated by methanol (400 mL), collected by filtration and dried to give the object compound (13.9 g, yield 97%).

$^1$H-NMR (400 MHz, CDCl$_3$): δ=0.88 (t, 6H, J=6.6 Hz, —OCH$_2$CH$_2$(CH$_2$)$_{15}$CH$_3$) 1.25-1.55 (m, 76H, —OCH$_2$CH$_2$(CH$_2$)$_{15}$CH$_3$), 1.77 (m, 4H, OCH$_2$CH$_2$(CH$_2$)$_{15}$CH$_3$), 3.89 (s, 3H, C(O)O—CH$_3$), 3.96 (t, 4H, J=6.6 Hz, —OCH$_2$CH$_2$(CH$_2$)$_{15}$CH$_3$), 6.63 (s, 1H, Ar—H), 7.15 (s, 2H, Ar—H)

Example 2: Synthesis of Methyl 3,5-bis(docosyloxy)benzoate

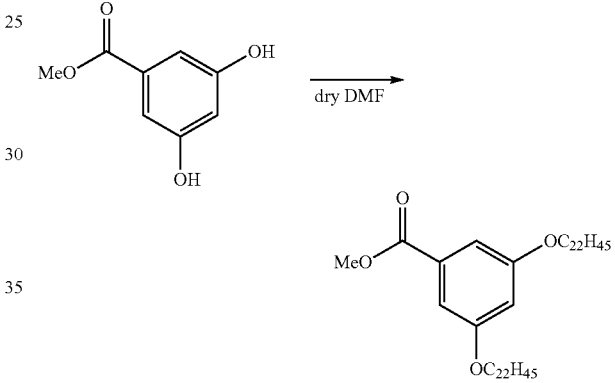

Under an argon atmosphere, potassium carbonate (20.0 g, 145 mmol), methyl 3,5-dihydroxybenzoate (3.60 g, 21.4 mmol), 1-bromodocosane (17.9 g, 46.0 mmol) were dissolved in N,N-dimethylformamide (200 mL), and the mixture was stirred at 70° C. for 16 hr. Completion of the reaction was confirmed by thin layer chromatography, the reaction solution was poured into water (1.00 L) to allow for precipitation to give a solid. The obtained solid was dissolved in dichloromethane (500 mL), and the solid was precipitated with methanol (400 mL), collect by filtration, and dried to give the object compound (16.1 g, yield 96%).

$^1$H-NMR (400 MHz, CDCl$_3$): δ=0.88 (t, 6H, J=6.6 Hz, —CH$_3$), 1.25-1.55 (m, 76H, —OCH$_2$CH$_2$ (CH$_2$)$_{19}$CH$_3$), 1.77 (m, 4H, —OCH$_2$CH$_2$(CH$_2$)$_{19}$CH$_3$), 3.89 (s, 3H, C(O)O—CH$_3$), 3.96 (t, 4H, J=6.6 Hz, —OCH$_2$CH$_2$(CH$_2$)$_{19}$CH$_3$), 6.63 (s, 1H, Ar—H), 7.15 (s, 2H, Ar—H)

Example 3: 2,3,4-tri(octadecyloxy)benzophenone

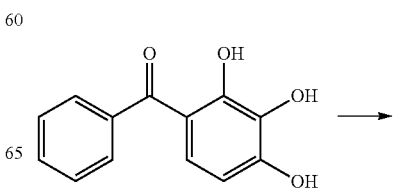

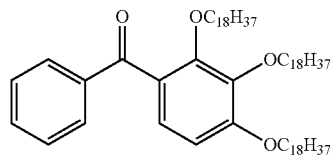

Under an argon atmosphere, potassium carbonate (4.35 g, 31.5 mmol), 2,3,4-trihydroxybenzophenone (1.61 g, 7.00 mmol), 1-bromooctadecane (7.32 g, 22.0 mmol) were dissolved in N,N-dimethylformamide (30 mL), and the mixture was stirred at 80° C. for 16 hr. Completion of the reaction was confirmed by thin layer chromatography, the reaction solution was poured into water (200 mL) to allow for precipitation to give a solid. The obtained solid was dissolved in dichloromethane (200 mL), and the solid was precipitated with methanol (300 mL), collected by filtration and dried to give the object compound (6.31 g, yield 91%).

$^1$H-NMR (400 MHz, CDCl$_3$): δ=0.88 (t, 9H, J=6.7 Hz, —C$\underline{H}_3$), 1.11-1.55 (m, 90H, —O—CH$_2$CH$_2$ (C$\underline{H}_2$)$_{15}$CH$_3$), 1.74-1.87 (m, 4H, —O—CH$_2$C$\underline{H}_2$(CH$_2$)$_{15}$CH$_3$), 3.88 (t, 2H, J=6.6 Hz, —O—C$\underline{H}_2$CH$_2$(CH$_2$)$_{15}$CH$_3$), 3.99 (t, 2H, J=6.6 Hz, —O—C$\underline{H}_2$CH$_2$(CH$_2$)$_{15}$CH$_3$), 4.02 (t, 2H, J=6.6 Hz, —O—C$\underline{H}_2$CH$_2$(CH$_2$)$_{15}$CH$_3$), 6.69 (d, 1H, J=8.6 Hz, Ar—H), 7.12 (d, 1H, J=8.6 Hz, Ar—H), 7.41 (m, 2H, Ar—H), 7.53 (m, 1H, Ar—H), 7.77 (m, 2H, Ar—H)

Example 4: Synthesis of 3,4,5-tri(octadecyloxy)toluene

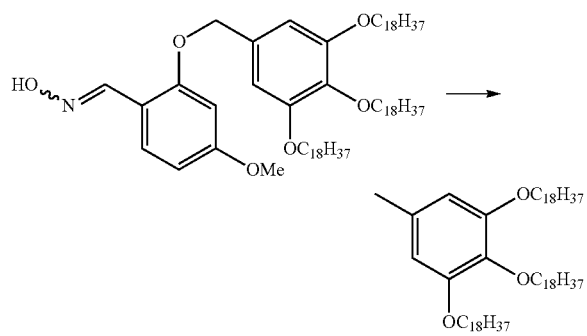

Under a hydrogen atmosphere, 2-tri(octadecyloxy)-benzyloxy-4-methoxy-benzaldoxime (487 mg, 470 μmol) was dissolved in a mixed solvent of THF (40 mL) and methanol (10 mL), 10 wt % Pd/C (53.3 mg) was added, and the mixture was stirred at room temperature for 64 hr. Completion of the reaction was confirmed by thin layer chromatography, the reaction solution was filtered through celite, and acetonitrile (200 mL) was added to the filtrate to precipitate a solid. The solid was collected by filtration, and dried to give the object compound (391 mg, yield 930).

$^1$H-NMR (400 MHz, CDCl$_2$): δ=0.88 (t, 9H, J=6.6 Hz, —OCH$_2$CH$_2$(CH$_2$)$_{19}$C$\underline{H}_3$), 1.26-1.80 (m, 96H, —OCH$_2$C$\underline{H}_2$(CH$_2$)$_{19}$CH$_3$), 2.27 (s, 3H, Ar-Me), 3.89-3.96 (m, 6H, —OC$\underline{H}_2$CH$_2$(CH$_2$)$_{19}$CH$_3$), 6.35 (s, 2H, Ar—H)

Example 5: Synthesis of Methyl 3,4,5-tris[3,4,5-tri(octadecyloxy)benzyloxy]benzoate

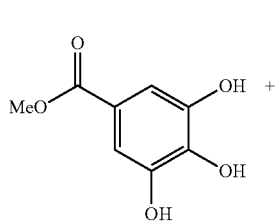

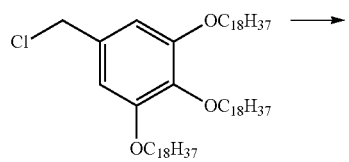

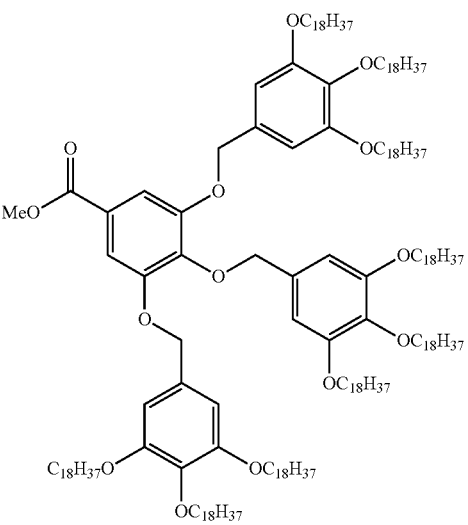

Under an argon atmosphere, potassium carbonate (1.39 g, 10.1 mmol), methyl 3,5-hydroxybenzoate (181 mg, 1.00 mmol), 3,4,5-tri(octadecyloxy)benzylchloride (2.81 g, 3.01 mmol) were dissolved in N,N-dimethylformamide (20 mL), and the mixture was stirred at 70° C. for 18 hr. Completion of the reaction was confirmed by thin layer chromatography, the reaction solution was poured into water (50 mL) to allow for precipitation to give a solid. The obtained solid was dissolved in dichloromethane (50 mL), and the solid was precipitated with acetonitrile (200 mL), collected by filtration, and dried to give a crude product of the object product. The obtained crude product was purified by silica gel column chromatography (dichloromethane/hexane (volume ratio)=1/2-1/1) to give the object compound (2.31 g, 81%).

$^1$H-NMR (400 MHz, CDCl$_3$): δ=0.88 (t, 9H, J=7.0 Hz, —O(CH$_2$)$_{17}$C$\underline{H}_3$), 1.25-1.74 (m, 291H, —OCH$_2$ (C$\underline{H}_2$+N$^5$—CH$_3$)$_{16}$CH$_3$), 3.75 (m, 6H, —OC$\underline{H}_2$(CH$_2$)$_{16}$CH$_3$), 3.90 (s, 3H, —C(O)OC$\underline{H}_3$), 3.86-3.94 (2m, 12H, —OC$\underline{H}_2$(CH$_2$)$_{16}$CH$_3$), 5.02 (s, 6H, 3×-$\underline{H}_2$C-Ar), 6.59 (s, 2H, Ar—$\underline{H}$), 6.62 (s, 4H, Ar—$\underline{H}$), 7.38 (s, 2H, Ar—H)

Example 6: Synthesis of Methyl 3,4,5-tri(octadecyloxy)benzoate

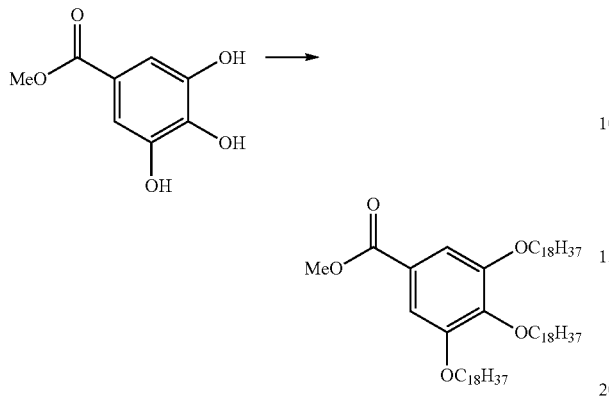

1-Bromooctadecane (64.0 g, 192 mmol), potassium carbonate (79.6 g, 576 mmol), 3,4,5-trihydroxymethylbenzoate (11.0 g, 60.0 mmol) were dissolved in N,N-dimethylformamide (600 mL), and the mixture was stirred at 90° C. for 16 hr. Completion of the reaction was confirmed by thin layer chromatography (hexane/dichloromethane (volume ratio)=2/1 and dichloromethane/methanol (volume ratio)=9/1), the reaction solution was poured into water (2.00 L), and the solid was precipitated, filtered and dried. The dry solid was dissolved in dichloromethane (500 mL), acetonitrile (1.50 L) was added to precipitate a solid. The solid was collected by filtration, and dried to give the object compound (56.7 g, 100%).

$^1$H-NMR (400 MHz, CDCl$_3$): δ=0.88 (t, 9H, J=6.8 Hz, —OCH$_2$(CH$_2$)$_{16}$C$\underline{H}_3$), 1.21-1.51 (m, 90H, —O—CH$_2$CH$_2$(C$\underline{H}_2$)$_{15}$CH$_3$) 1.70-, 6H, —O—CH$_2$—C$\underline{H}_2$—(CH$_2$)$_{15}$—CH$_3$), 3.89 (s, 3H, C(O)OC$\underline{H}_3$), 3.99-4.03 (m, 6H, Ar—OC$\underline{H}_2$), 4.99 (s, 2H, Ar—H), 7.25 (s, 2H, Ar—H)

Example 7: Synthesis of 3,4,5-tri(octadecyloxy)benzyl acetate (1) synthesis of 3,4,5-tri(octadecyloxy)benzyl alcohol

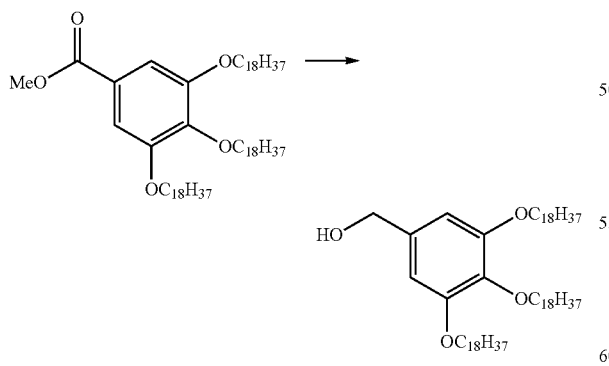

Under an argon atmosphere, methyl 3,4,5-tri(octadecyloxy)benzoate (10.0 g, 10.6 mmol) was dissolved in tetrahydrofuran (150 mL), lithium aluminum hydride (810 mg, 21.3 mmol) was added, and the mixture was stirred at room temperature for 30 min. Completion of the reaction was confirmed by thin layer chromatography, quenched with 4 M aqueous sodium hydroxide solution (6.0 mL), and the reaction solution was filtered. To the filtrate was added methanol (500 mL) to precipitate a solid, which was collected by filtration and dried to give the object compound (9.65 g, yield 99%).

(2) Synthesis of 3,4,5-tri(octadecyloxy)benzyl acetate

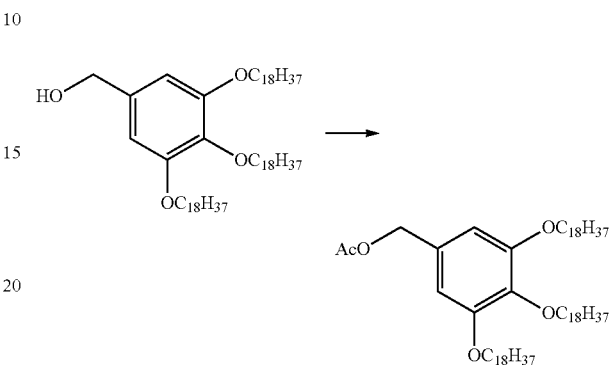

3,4,5-tri(Octadecyloxy)benzyl alcohol (10.0 g, 10.5 mmol), acetic anhydride (9.90 mL, 105 mmol), pyridine (8.40 mL, 105 mmol), 4-dimethylaminopyridine (128 mg, 1.05 mmol) were dissolved in dichloromethane (100 mL), and the mixture was stirred at room temperature for 5 min. Completion of the reaction was confirmed by thin layer chromatography, acetonitrile (500 mL) was added to precipitate a solid, which was collected by filtration. The obtained solid was purified by silica gel column chromatography (hexane/dichloromethane=2/1-1/1) to quantitatively give the object compound (10.4 g) as a white solid.

$^1$H-NMR (400 MHz, CDCl$_3$): δ=0.88 (t, 9H, J=6.8 Hz, —C$\underline{H}_3$), 1.26-1.50 (m, 90H, —O—CH$_2$—CH$_2$—(CH$_2$)$_{15}$CH$_3$), 1.70-1.83 (m, 6H, —O—CH$_2$—C$\underline{H}_2$—(CH$_2$)$_{15}$—CH$_3$), 2.10 (s, 3H, C(O) C$\underline{H}_3$), 3.92-3.98 (m, 6H, Ar—OC$\underline{H}_2$), 4.99 (s, 2H, Ar—C$\underline{H}_2$), 6.54 (s, 2H, Ar—H)

Example 8: Synthesis of 1,2,3-tri(octadecyloxy)propane

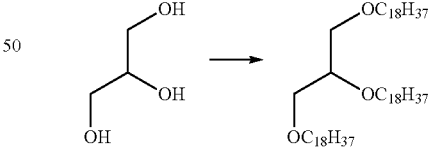

Under an argon atmosphere, potassium carbonate (12.4 g, 90.0 mmol), glycerol (921 mg, 10.0 mmol), 1-bromooctadecane (11.0 g, 33.0 mmol) were dissolved in N,N-dimethylformamide (100 mL), and the mixture was stirred at 110° C. for 16 hr. Completion of the reaction was confirmed by thin layer chromatography, and the reaction solution was poured into water (400 mL) to allow for precipitation to give a solid. The obtained solid was purified by silica gel column chromatography (dichloromethane) to give the object compound (4.30 g, 51%).

$^1$H-NMR (400 mHz, CDCl$_3$): δ=0.88 (t, 9H, J=6.8 Hz, —CH$_2$(CH$_2$)$_{16}$C$\underline{H}_3$), 1.18-1.36 (m, 95H, —CH$_2$CH$_2$ (C H$_2$)$_{15}$CH$_3$, HC(CH$_2$)$_2$), 1.53-1.62 (m, 6H, —CH$_2$CH$_2$(CH$_2$)$_{15}$CH$_3$), 3.62-3.66 (m, 6H, —CH$_2$(CH$_2$)$_{16}$CH$_3$)

Example 9: Synthesis of 1,3-di(octadecyloxy)-2,2-di(octadecyloxymethyl)propane

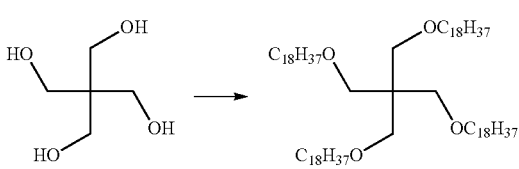

Under an argon atmosphere, potassium carbonate (6.10 g, 44.1 mmol), pentaerythritol (501 mg, 3.67 mmol), 1-bromooctadecane (5.50 g, 16.5 mmol) were dissolved in N,N-dimethylformamide (35 mL), and the mixture was stirred at 110° C. for 16 hr. Completion of the reaction was confirmed by thin layer chromatography, the reaction solution was poured into water (400 mL) to allow for precipitation to give a solid. The obtained solid was dissolved in dichloromethane (200 mL), and the solid was precipitated with methanol (300 mL), collected by filtration, and dried to give the object compound (3.57 g, 85%).

$^1$H-NMR (400 MHz, CDCl$_3$): δ=0.88 (t, J=6.8 Hz, 12H, —CH$_2$(CH$_2$)$_{16}$CH$_3$), 1.17-1.36 (m, 128H, —CH$_2$CH$_2$ (CH$_2$)$_{16}$CH$_3$), 1.53-1.60 (m, 8H, —C(CH$_2$)$_4$), 3.62-3.66 (m, 8H, —CH$_2$(CH$_2$)$_{16}$CH$_3$)

Example 10: Synthesis of Methyl 4-docosyloxybenzoate

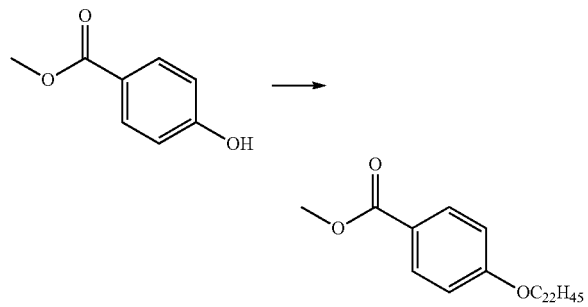

Under an argon atmosphere, potassium carbonate (1.36 g, 9.85 mmol), methyl 4-hydroxybenzoate (500 mg, 3.29 mmol), 1-bromooctadecane (1.28 g, 3.62 mmol) were dissolved in N,N-dimethylformamide (30 mL), and the mixture was stirred at 90° C. for 16 hr. Completion of the reaction was confirmed by thin layer chromatography, and the reaction solution was poured into water (400 mL) to allow for precipitation to give a solid. The obtained solid was dissolved in ethyl acetate (50 mL) at 70° C., cooled to room temperature to precipitate crystals, which were collected by filtration, and dried to give the object compound (1.37 g, 91%).

$^1$H-NMR (400 MHz, CDCl$_3$): δ=0.88 (t, 3H, J=6.8 Hz, —CH$_2$CH$_2$(CH$_2$)$_{15}$CH$_3$), 1.26-1.58 (m, 38H, —CH$_2$CH$_2$ (CH$_2$)$_{19}$CH$_3$), 1.76-1.83 (m, 2H, —CH$_2$CH$_2$(CH$_2$)$_{19}$CH$_3$), 3.88 (s, 3H, —C(O)OCH$_3$), 4.00 (t, 2H, J=6.4 Hz, —CH$_2$CH$_2$(CH$_2$)$_{15}$CH$_3$), 6.90 (d, 2H, J=9.5 Hz, Ar—H), 7.98 (d, 2H, J=9.5 Hz, Ar—H)

Example 11: Synthesis of Methyl 3,4,5-tri(octadecyloxy)-cyclohexane carboxylate

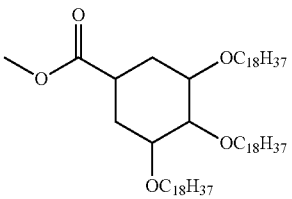

Cyclohexane was added to methyl 3,4,5-tri(octadecyloxy)benzoate (1.00 g, 10.6 mmol), 5% rhodium-carbon (0.8 g) was added, and hydrogen reduction was performed at 80° C. and 10 atm for 16 hr. To the mixture after hydrogen reduction was added tetrahydrofuran (10 mL), and the catalyst was filtered off. The filtrate was concentrated, methanol (8 mL) was added to the concentrated solution, and the mixture was stirred. The obtained precipitate was collected by filtration, and dried to give the object compound (820 mg, yield 82%).

$^1$H-NMR (400 MHz, CDCl$_3$): δ=0.89 (9H, t, J=6.9 Hz, C$_{17}$H$_{34}$-Me), 1.25-1.44 (90H, m), 1.52-1.60 (6H, m), 1.86-1.94 (4H, m), 2.23 (1H, m), 3.09-3.14 (2H, m), 3.41-3.47 (4H, m), 3.64-3.68 (5H, m), 3.86 (1H, s)

Example 12: Synthesis of Methyl 2,4-di(docosyloxy)benzoate

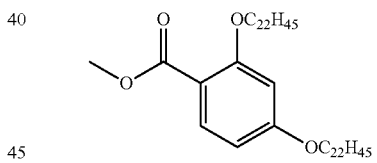

Under an argon atmosphere, potassium carbonate (29.9 g, 217 mmol), methyl 2,4-dihydroxybenzoate (3.65 g, 21.7 mmol), 1-bromodocosane (17.33 g, 44.5 mmol) were dissolved in N,N-dimethylformamide (150 mL), and the mixture was stirred at 70° C. for 16 hr. Completion of the reaction was confirmed by thin layer chromatography, and the reaction solution was poured into water (1.00 L) to allow for precipitation to give a solid. The obtained solid was dissolved in dichloromethane (500 mL), and the solid was precipitated with methanol (400 mL), collected by filtration, and dried to give the object compound (16.7 g, yield 98%).

$^1$H-NMR (400 MHz, CDCl$_3$): δ=0.88 (t, 6H, J=6.6 Hz, —CH$_3$), 1.13-1.56 (m, 76H, —OCH$_2$CH$_2$ (CH$_2$)$_{19}$CH$_3$) 1.81 (m, 4H, —OCH$_2$CH$_2$(CH$_2$)$_{19}$CH$_3$), 3.89 (s, 3H, C(O)O—CH$_3$), 4.02 (dd, 4H, J=6.6, 14.8 Hz, —OCH$_2$CH$_2$(CH$_2$)$_{19}$CH$_3$) 6.63 (s, 1H, Ar—H) 7.15 (s, 2H, Ar—H)

Example 13: Synthesis of pivaloyloxymethyl-3,4,5-tri(octadecyloxy)benzene

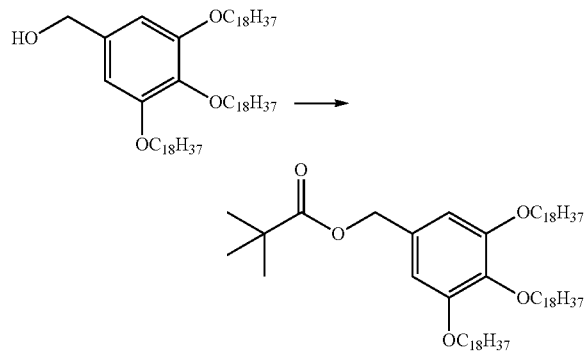

Under an argon atmosphere, 3,4,5-tri(octadecyloxy)benzyl alcohol (2.73 g, 2.99 mmol) was dissolved in dichloromethane (25 mL), triethylamine (1.67 mL, 12.0 mmol), pivaloyl chloride (781 μL, 6.00 mmol), 4-dimethylaminopyridine (7.32 mg, 600 μmol) were successively added, and the mixture was stirred at room temperature for 7 hr. Completion of the reaction was confirmed by thin layer chromatography, acetonitrile (125 mL) was added to the reaction solution to precipitate a solid, which was collected by filtration. The obtained solid was dried under reduced pressure to quantitatively give the object compound (2.80 g) as a white solid.

$^1$H-NMR (400 MHz, CDCl$_3$): δ=0.879 (t, J=7.06 Hz, 9H), 1.23 (s, 9H), 1.24-1.40 (m, 84H), 1.40-1.52 (m, 6H), 1.70-1.81 (m, 6H), 3.92 (t, J=6.8 Hz, 2H), 3.95 (t, J=6.8 Hz, 4H), 5.01 (s, 2H), 6.51 (s, 2H)

Example 14: Synthesis of (2S)-2-(acetylamino)-4-methylpentanoyloxymethyl-3,4,5-tri(octadecyloxy)benzene

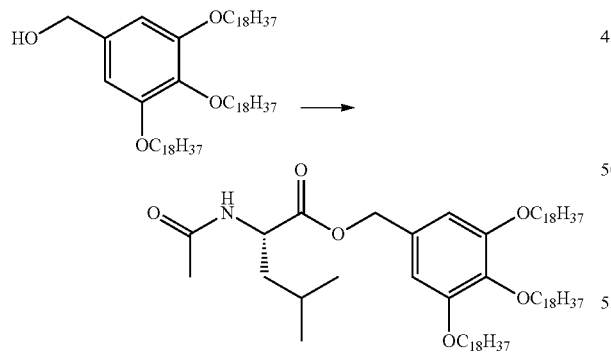

3,4,5-tri(Octadecyloxy)benzyl alcohol (1.83 g, 2.00 mmol), N-acetylleucine (700 mg, 4.09 mmol), 2,6-dimethylaminopyridine (2.58 mg, 20.0 μmol) were dissolved in dichloromethane (20 mL), diisopropylethylamine (1.16 mL, 6.79 mmol) and HBTU (1.90 g, 5.00 mmol) were added, and the mixture was stirred at room temperature for 15 hr and further at 40° C. for 21 hr. The reaction solution was filtered, acetonitrile (100 mL) was added to the filtrate to precipitate a solid, which was collected by filtration. The obtained solid was dried under reduced pressure to give the object compound (1.97 g) as a white solid.

$^1$H-NMR (400 MHz, CDCl$_3$): δ=0.879 (t, J=7.06 Hz, 9H), 0.913 (d, J=3.2 Hz, 3H), 0.929 (d, J=3.2 Hz, 3H), 1.22-1.40 (m, 84H), 1.40-1.52 (m, 7H), 2.02 (s, 3H), 1.60-1.82 (m, 8H), 3.94 (t, J=6.4 Hz, 2H), 3.95 (t, J=6.8 Hz, 4H), 4.684 (ddd, J=13.6, 4.8, 4.8 Hz, 1H), 5.024 (d, 12.4 Hz), 5.082 (d, 12.4 Hz), 5.817 (d, 8.4 Hz), 6.52 (s, 2H)

Example 15: Synthesis of triisopropylsilyloxymethyl-3,4,5-tri(octadecyloxy)benzene

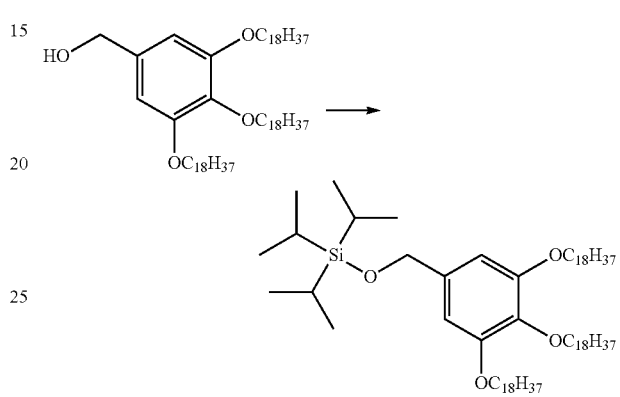

Under an argon atmosphere, 3,4,5-tri(octadecyloxy)benzyl alcohol (4.57 g, 5.00 mmol) and imidazole (1.36 g, 20.0 mmol) were dissolved in a mixed solvent of dichloromethane (40 mL) and N,N-dimethylformamide (10 mL), triisopropylsilylchloride (2.12 mL, 10.0 mmol) was added and the mixture was stirred at 40° C. for 6 hr. After cooling to room temperature, acetonitrile (250 mL) was added to the reaction solution to precipitate a solid, which was collected by filtration. The obtained solid was dried under reduced pressure to give the object compound (5.23 g) as a white solid.

$^1$H-NMR (400 MHz, CDCl$_3$): δ=0.879 (t, J=7.06 Hz, 9H), 1.09 (d, 18H, 6.0 Hz), 1.12-1.20 (m, 3H), 1.22-1.40 (m, 84H), 1.40-1.52 (m, 6H), 1.70-1.82 (m, 6H), 3.91 (t, J=6.8 Hz, 2H), 3.97 (t, J=6.8 Hz, 4H), 4.75 (s, 2H), 6.56 (s, 2H)

Example 16: Synthesis of 4-(3,4,5-tri(octadecyloxy)benzoyl)-morpholine

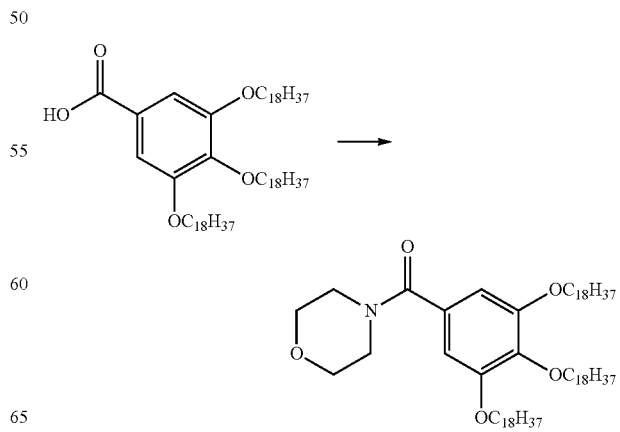

Under an argon atmosphere, 3,4,5-tri(octadecyloxy)benzoic acid (5.00 g, 5.39 mmol) was dissolved in dichloromethane (50 mL), HBTU (6.13 g, 16.2 mmol), morpholine (1.31 mL, 16.2 mmol), and diisopropylethylamine (2.90 mL, 16.2 mmol) were successively added, and the mixture was stirred at room temperature for 18 hr. The end-point of the reaction was confirmed by thin layer chromatography (hexane/dichloromethane/ethyl acetate=25/50/25), acetonitrile (250 mL) was added to the reaction solution to precipitate a solid, which was collected by filtration. The obtained solid was purified by silica gel column chromatography (dichloromethane/methanol=100/0-95/5) to give the object compound (5.18 g) as a white solid.

$^1$H-NMR (400 MHz, CDCl$_3$): δ=0.879 (t, J=6.8 Hz, 9H), 1.26-1.47 (m, 84H), 1.42-1.53 (m, 6H), 1.71-1.80 (m, 6H), 3.69 (m, 8H), 3.95 (m, 6H), 6.51 (s, 2H)

Experimental Example 1

As the precipitation object, the pentamer synthesized in Reference Example 2 or the icosamer synthesized in Reference Example 4 was used to investigate the relationship between the addition amount of the precipitation promoter and the recovery rate of the precipitation object. The precipitation object and the precipitation promoter (methyl 3,4,5-tri(octadecyloxy)benzoate) synthesized in Example 6 in the amounts shown in Tables 1 and 2 were dissolved in dichloromethane (2 mL), solids were precipitated with acetonitrile in the amounts shown in Tables 1 and 2, the obtained solids were collected by filtration by using Kiriyama funnel (21 m/m) and filter paper (No-5A), washed with acetonitrile (20 mL) and dried under reduced pressure. The recovery rate calculated from the amount of the precipitation object used (i.e., pentamer of Reference Example 2 or icosamer of Reference Example 4) and the amount of the precipitation promoter used and the amount of the collected mixture of the precipitation object and the precipitation promoter after drying (=100×(amount (mg) of collected mixture of precipitation object and precipitation promoter after drying)/(amount (mg) of precipitation object used+amount (mg) of precipitation promoter used)) is shown in Tables 1 and 2.

TABLE 1

| pentamer (μmol) of Reference Example 2 | precipitation promoter of Example 6 | | acetonitrile (mL) | recovery rate (%) |
|---|---|---|---|---|
| | (μmol) | (molar equivalents)*$^1$ | | |
| 57.3 | no addition | — | 40 | 2 |
| 58.1 | 25.8 | 0.4 | 40 | 93 |
| 58.1 | 51.5 | 0.9 | 40 | 92 |
| 56.1 | 53.2 | 0.9 | 80 | 91 |
| 56.7 | 103.6 | 1.8 | 40 | 100 |
| 55.3 | 100.8 | 1.8 | 30 | 99 |
| 53.2 | 103.6 | 1.9 | 20 | 100 |

*$^1$molar equivalents of precipitation promoter of Example 6 relative to pentamer of Reference Example 2

TABLE 2

| icosamer (μmol) of Reference Example 4 | precipitation promoter of Example 6 | | acetonitrile (mL) | recovery rate (%) |
|---|---|---|---|---|
| | (μmol) | (molar equivalents)*$^1$ | | |
| 40.1 | 70.9 | 1.8 | 40 | 98 |

*$^1$molar equivalents of precipitation promoter of Example 6 relative to icosamer of Reference Example 4

Experimental Example 2

As the precipitation object, the decamer synthesized in Reference Example 3 was used to investigate the relationship between the kind of the precipitation promoter and the recovery rate of the precipitation object. The decamer of Reference Example 3 and any of the precipitation promoters synthesized in Comparative Examples 1 and 2 and Examples 1 to 12 in the amounts shown in Table 3 were dissolved in dichloromethane (0.5 mL), solids were precipitated with acetonitrile (2.5 mL), the obtained solids were collected by filtration by using Kiriyama funnel (21 m/m) and filter paper (No-5A), washed with acetonitrile (2.0 mL) and dried under reduced pressure. The recovery rate calculated from the amount of the precipitation object used (i.e., decamer of Reference Example 3) and the amount of the precipitation promoter used and the amounts of the collected precipitation object and precipitation promoter after drying (=100×(amount (mg) of collected mixture of precipitation object and precipitation promoter after drying)/(amount (mg) of precipitation object used+amount (mg) of precipitation promoter used)) is shown in Table 3.

TABLE 3

| kind of precipitation promoter | amount of precipitation promoter to be added | | decamer (μmol) of Reference Example 3 | recovery rate (%) |
|---|---|---|---|---|
| | (μmol) | (molar equivalents)*$^1$ | | |
| no addition | — | — | 8.5 | 69 |
| Comparative Example 1 | 15.2 | 1.8 | 8.6 | 61 |
| Comparative Example 2 | 14.8 | 1.7 | 8.5 | 8 |
| Example 1 | 15.3 | 1.8 | 8.5 | 89 |
| Example 2 | 14.4 | 1.7 | 8.5 | 73 |
| Example 3 | 14.9 | 1.8 | 8.5 | 100 |
| Example 4 | 14.9 | 1.7 | 8.5 | 83 |
| Example 5 | 14.9 | 1.7 | 8.6 | 100 |
| Example 6 | 15.0 | 1.8 | 8.4 | 96 |
| Example 7 | 14.8 | 1.7 | 8.5 | 99 |
| Example 8 | 15.1 | 1.8 | 8.5 | 71 |
| Example 9 | 14.9 | 1.8 | 8.5 | 74 |
| Example 10 | 15.0 | 1.8 | 8.5 | 73 |
| Example 11 | 14.8 | 1.7 | 8.5 | 99 |
| Example 12 | 14.4 | 1.7 | 8.5 | 75 |

*$^1$molar equivalents of each precipitation promoter relative to decamer of Reference Example 3

As shown in Table 3, using the precipitation promoters of Examples 1 to 12, precipitation of the decamer of Reference Example 3 can be promoted and the recovery rate thereof can be improved. On the other hand, when the precipitation promoter of Comparative Example 1 having a branched chain aliphatic hydrocarbon group, and the precipitation promoter of Comparative Example 2 having a linear aliphatic hydrocarbon group and the total carbon number of the group of less than 20 were used, the recovery rate of the decamer of Reference Example 3 decreased as compared to the non-use thereof.

Experimental Example 3

As the precipitation object, the pentamer synthesized in Reference Example 2 was used to investigate the relationship between the kind of the precipitation promoter and the recovery rate of the precipitation object. The pentamer of Reference Example 2 and any of the precipitation promoters synthesized in Examples 13-15 in the amounts shown in Table 4 were dissolved in dichloromethane. Acetonitrile in the amount shown in Table 4 was added dropwise to the obtained solution with stirring at 24° C. over 3 min to precipitate solids to give slurry. The obtained slurry was stood in an ice bath for 10 min, and the precipitated solid was collected by filtration by using 25Φ Kiriyama funnel and 5C filter paper, and the obtained solid was washed with acetonitrile in the amount shown in Table 4. The obtained solid was dried under reduced pressure overnight. The recovery rate calculated from the amount of the precipitation object used (i.e., pentamer of Reference Example 2) and the amount of the precipitation promoter used and the amount of the collected mixture of the precipitation object and the precipitation promoter after drying (=100×(amount (mg) of collected mixture of precipitation object and precipitation promoter after drying)/(amount (mg) of precipitation object used+amount (mg) of precipitation promoter used)) is shown in Table 4.

TABLE 4

| kind of precipitation promoter | amount of precipitation promoter to be added | | pentamer (µmol) of Reference Example 2 | dichloromethane (mL) | acetonitrile (mL) for precipitation | acetonitrile (mL) for washing | recovery rate (%) |
|---|---|---|---|---|---|---|---|
| | (µmol) | (molar equivalents)*1 | | | | | |
| Example 13 | 70.5 | 1.5 | 45.9 | 3.0 | 9.0 | 5.0 | 98.3 |
| Example 14 | 75.9 | 1.7 | 45.9 | 3.0 | 9.0 | 5.0 | 97.2 |
| Example 15 | 24.5 | 1.5 | 15.9 | 1.0 | 3.0 | 2.0 | 99.7 |

*1 molar equivalents of each precipitation promoter relative to pentamer of Reference Example 2

Experimental Example 4

As the precipitation object, the icosamer synthesized in Reference Example 4 was used to investigate the relationship between the kind of the precipitation promoter and the recovery rate of the precipitation object. The pentamer of Reference Example 2 and any of the precipitation promoters synthesized in Examples 13 to 15 in the amounts shown in Table 5 were dissolved in dichloromethane. Acetonitrile (10.5 mL) was added dropwise to the obtained solution with stirring at 24° C. over 3 min to precipitate solids to give slurry. The obtained slurry was stood in an ice bath for 10 min, and the precipitated solid was collected by filtration by using 25Φ Kiriyama funnel and 5C filter paper, and the obtained solid was washed with acetonitrile (5.0 mL). The obtained solid was dried under reduced pressure overnight. The recovery rate calculated from the amount of the precipitation object used (i.e., icosamer of Reference Example 4) and the amount of the precipitation promoter used and the amount of the collected mixture of the precipitation object and the precipitation promoter after drying (=100×(amount of collected mixture of precipitation object and precipitation promoter after drying)/(amount (mg) of precipitation object used+amount (mg) of precipitation promoter used)) is shown in Table 5.

TABLE 5

| kind of precipitation promoter | amount of precipitation promoter to be added | | icosamer (µmol) of Reference Example 4 | recovery rate (%) |
|---|---|---|---|---|
| | (µmol) | (molar equivalents)*1 | | |
| Example 13 | 55.3 | 1.1 | 48.2 | 99.6 |
| Example 14 | 58.8 | 1.2 | 47.8 | 99.6 |
| Example 15 | 55.5 | 1.2 | 48.2 | 95.0 |

*1 molar equivalents of each precipitation promoter relative to icosamer of Reference Example 4

Experimental Example 5

First, a peptide collection test was performed without using a precipitation promoter. To be specific, a peptide (H-Lys(Boc)-Pro-Pro-Ala-Lys(Boc)-Leu-Gln(Trt)-Pro-Arg(Pbf)-OTOB, 435 mg, 0.166 mmol) wherein a carboxy group was protected by a 3,4,5-tri(octadecyloxy)benzyl group (TOB) was dissolved in chloroform (10 mL). The obtained solution was concentrated under reduced pressure, and about 5 mL of chloroform was removed from the solution to give a concentrate. Acetonitrile (20 mL) was added to the concentrate to precipitate a solid. The precipitate was collected by filtration, and dried under reduced pressure to give the dry peptide. The recovery rate calculated from the amount of the peptide used and the amount of the collected peptide after drying (=100×(amount (mg) of collected peptide after drying)/(amount (mg) of peptide used)) was 71%.

In the same manner as above except that 3,4,5-tri(octadecyloxy)benzyl alcohol was used as a precipitation promoter, a peptide collection test was performed. To be specific, a peptide protected by a 3,4,5-tri(octadecyloxy)benzyl group (TOB) (H-Lys(Boc)-Pro-Pro-Ala-Lys(Boc)-Leu-Gln(Trt)-Pro-Arg(Pbf)-OTOB, 435 mg, 0.166 mmol) wherein a carboxy group and 3,4,5-tri(octadecyloxy)benzyl alcohol (200 mg, 0.22 mmol) were dissolved in chloroform (10 mL). The obtained solution was concentrated under reduced pressure, and about 5 mL of chloroform was removed from the solution to give a concentrate. Acetonitrile (20 mL) was added to the concentrate to precipitate a solid. The precipitate was collected by filtration, and dried under reduced pressure to give a dry mixture of the peptide and the precipitation promoter. The recovery rate calculated from the amount of the peptide used and the amount of the precipitation promoter used and the amount of the collected mixture of the peptide and the precipitation promoter after drying (=100×(amount (mg) of collected mixture of peptide and precipitation promoter after drying)/(amount (mg) of peptide used+amount (mg) of precipitation promoter used)) was 97%.

Example 17: Continuous Synthesis of Phosphorthioate Dimer in Solution by Using Precipitation Promoter Under an argon atmosphere, 5'-O-(4,4'-dimethoxytrityl) deoxythymidine-3'-yl [3,4,5-tri(octadecyloxy)benzyl]succinate (1.85 g, 1.2 mmol), 3,4,5-tri(octadecyloxy)benzyl acetate (1.86 g, 1.20 mmol) which is the precipitation promoter synthesized in Example 7 were dissolved in dichloromethane (40 mL), indole (1.40 g, 12.0 mmol) and trifluoroacetic acid (88.9 µL, 1.20 mmol) were added and the mixture was stirred at room temperature for 2 hr, and completion of the reaction was confirmed by thin layer chromatography. The reaction mixture was neutralized with 1-methylimidazole (99.7 µL, 1.26 mmol), a solution of 4,5-dicyanoimidazole (476 mg, 4.03 mmol), 5'-O-(4,4'-dimethoxytrityl)deoxythymidine-3'-[O-(2-cyanoethyl)-(N,N-diisopropyl)]-phosphoramidite (2.00 g, 2.69 mmol) in acetonitrile was added, and the mixture was stirred at room temperature for 60 min, and completion of the reaction was confirmed by thin layer chromatography. Furthermore, 3-[(N,N-dimethylaminomethylidene)amino]-3H-1,2,4-dithiazole-5-thione (608 mg, 2.96 mmol) was added and the mixture was stirred at room temperature for 30 min. Acetic anhydride (56.6 µL, 0.60 mmol), 2,4,6-trimethylpyridine (79.1 µL, 0.60 mmol), 1-methylimidazole (47.5 µL, 0.60 mmol) were added and the mixture was stirred at room temperature for 15 min. Acetonitrile (200 mL) was added to the reaction solution, and the precipitated solid was suction-filtrated using Kiriyama funnel and dried to give 5'-O-(4,4'-dimethoxytrityl)-deoxythymidine-3'-[O-(2-cyanoethyl)] phosphorothionyl deoxythymidine-3'-yl [3,4,5-tri(octadecyloxy)benzyl] succinate (4.150 g, yield 99.8%) as a white solid.

Example 18: Continuous Synthesis of Phosphorthioate Icosamer (Sequence: 5'-TCCCGCCTGTGACATGCATT-3') in Solution by Using Precipitation Promoter (1) Synthesis of Phosphorthioate Icosamer Bonded to Pseudo Solid Phase Protecting Group Operations similar to those of Example 17 were repeated 19 times to give 5'-O-(4,4'-dimethoxytrityl)-deoxythymidine 3'-[O-(2-cyanoethyl)]phosphorothionyl-N⁴-benzoyl-deoxycytidine 3'-[O-(2-cyanoethyl)]phosphorothionyl-N⁴-benzoyl-deoxycytidine 3'-[O-(2-cyanoethyl)]phosphorothionyl-N⁴-benzoyl-deoxycytidine 3'-[O-(2-cyanoethyl)]phosphorothionyl-N²-isobutyryl-deoxyguanosine 3'-[O-(2-cyanoethyl)]phosphorothionyl-N⁴-benzoyl-deoxycytidine 3'-[O-(2-cyanoethyl)]phosphorothionyl-N⁴-benzoyl-deoxycytidine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-deoxythymidine 3'-[O-(2-cyanoethyl)]phosphorothionyl-N²-isobutyryl-deoxyguanosine 3'-[O-(2-cyanoethyl)]phosphorothionyl-N⁶-benzoyl-deoxyadenosine 3'-[O-(2-cyanoethyl)]phosphorothionyl-N⁴-benzoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O—(2-cyanoethyl)]phosphorothionyl-N²-isobutyryl-deoxyguanosine 3'-[O-(2-cyanoethyl)]phosphorothionyl-N⁴-benzoyl-deoxycytidine 3'-[O-(2-cyanoethyl)]phosphorothionyl-N⁶-benzoyl-deoxyadenosine 3'-[O-(2-cyanoethyl)]phosphorothionyl-deoxythymidine 3'-[O-(2-cyanoethyl)]phosphorothionyl-deoxythymidine 3'-yl 3,4,5-tri(octadecyloxy)benzyl succinate (8.55 g).

(2) Synthesis (Deprotection) and Purification of Phosphorthioate Icosamer

The compound (100 mg, 10.3 µmol) synthesized in the above-mentioned (1) and 30 wt % aqueous ammonia (5.00 mL) were placed in an autoclave, heated at 65° C. for 4 hr, and insoluble material was filtered through a syringe filter (WHATMAN 25 mm GD/X PTFE 0.45 µm). The filtrate was further diluted with 0.1 M aqueous ammonium acetate solution (50 mL) and subjected to C-18 cartridge purification, and the obtained eluate was freeze-dried to give the object products: deoxythymidinyl-[3'→5']-deoxycytidinyl-[3'→5']-deoxycytidinyl-[3'→5']-deoxycytidinyl-[3'→5']-deoxyguanidyl-[3'→5']-deoxycytidinyl-[3'→5']-deoxycytidinyl-[3'→5']-deoxythymidinyl-[3'→5']-deoxyguanidyl-[3'→5']-deoxythymidinyl-[3'→5']-deoxyguanidyl-[3'→5']-deoxyadenylyl-[3'→5']-deoxycytidinyl-[3'→5']-deoxyadenylyl-[3'→5']-deoxythymidinyl-[3'→5']-deoxyguanidyl-[3'→5']-deoxycytidinyl-[3'→5']-deoxyadenylyl-[3'→5']-deoxythymidinyl-[3'→5']-deoxythymidine.

HPLC (shodex ODP (4.6φ×150 mm), flow rate 0.5 mL/min, 15 mM TEA+20 mM HFIP/MeOH=95/5, 15 mM TEA+20 mM HFIP/MeOH=50/50 gradient: 0-7.4 min; 0 to 60%, 7.5 to 11 min; 100%, λ=254 nm): Rt=6.26 min (73%); TOF/MS: 6344.59[M-H]⁻

Example 19: Continuous Synthesis of Phosphorthioate Dimer in Solution by Using Precipitation Promoter

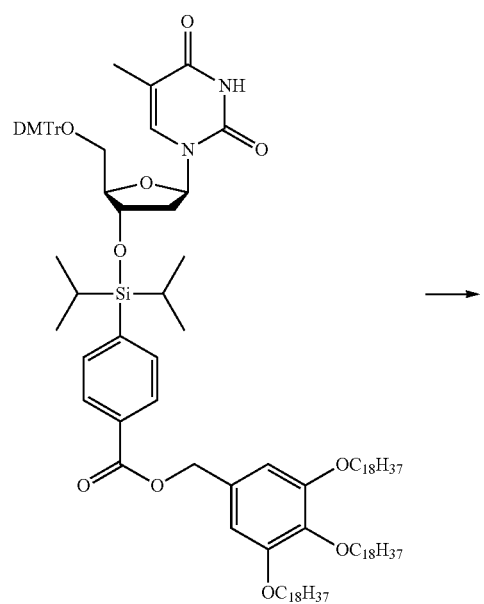

-continued

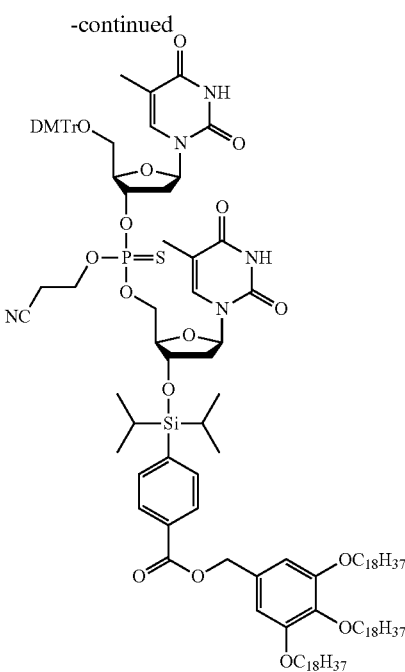

Under an argon atmosphere, 5'-O-(4,4'-dimethoxytrityl) deoxythymidine-3'-yl-diisopropyl-4-[3,4,5-tri(octadecyloxy)benzyloxycarbonyl]phenyl silane (330 mg, 200 μmol), and 3,4,5-tri(octadecyloxy)benzyl acetate (290 mg, 303 μmol) which is the precipitation promoter synthesized in Example 7 were dissolved in dichloromethane (5.0 mL), indole (469 mg, 4.00 mmol), trifluoroacetic acid (30.6 μL, 400 μmol) were added and the mixture was stirred at room temperature for 2 hr, and completion of the reaction was confirmed by thin layer chromatography. The reaction mixture was neutralized with 1-methylimidazole (34.8 μL, 439 μmol), a solution of 5-benzylthio-1H-tetrazole (115 mg, 600 μmol), 5'-O-(4,4'-dimethoxytrityl)deoxythymidine-3'-[O-(2-cyanoethyl)-(N,N-diisopropyl)]-phosphoramidite (447 mg, 600 μmol) in acetonitrile was added, and the mixture was stirred at room temperature for 60 min, and completion of the reaction was confirmed by thin layer chromatography. Furthermore, 3-[(N,N-dimethylaminomethylidene)amino]-3H-1,2,4-dithiazole-5-thione (136 mg, 662 μmol) was added and the mixture was stirred at room temperature for 30 min. Acetonitrile (30 mL) was added to the reaction solution, and the precipitated solid was suction-filtrated using Kiriyama funnel and dried to give 5'-O-(4,4'-dimethoxytrityl)-deoxythymidine-3'-[O-(2-cyanoethyl)]phosphorothionyl deoxythymidine-3'-yl [3,4,5-tri(octadecyloxy)benzyl] succinate (398 mg, yield 98%) as a white solid.

$^1$H-NMR (400 MHz, CDCl$_3$): δ=0.88 (t, 9H, J=6.6 Hz, —CH$_3$), 1.00-1.07 (m, 12H, —Si—CH—(CH$_3$)$_2$), 1.21-2.00 (m, 96H, —OCH$_2$(CH$_2$)$_{15}$CH$_3$), 2.35-2.50 (m, 3H, 2'-H), 2.56-2.60 (m, 2H, 2'-H+5'-H), 2.71 (m, 1H, 5'-H), 3.41-3.46 (m, 2H, 5'-H), 3.78 (s, 6H, DMTr-OCH$_3$), 3.93-3.99 (m, 6H, —OCH$_2$(CH$_2$)$_{15}$CH$_3$) 4.11-4.30 (m, 6H, 3'-H, 4'-H, —CH$_2$CH$_2$CN) 4.51-4.60 (m, 1H, 4'-H), 5.24 (s, 2H, Ar—CH$_2$—O—), 5.32 (m, 1H, 3'-H), 6.28 (m, 1H, 1H'—H), 6.36 (m, 1H, 1H'—H), 6.64 (s, 2H, Ar—H), 6.84 (m, 4H, DMTr-H), 7.22-7.63 (m, 11H, —Si—Ar, DMTr-H), 8.05-8.08 (m, 2H, —Si—Ar), 8.58-8.95 (m, 2H, N$^3$—H)

Example 20: Continuous Synthesis of Phosphorthioate Dimer in Solution by Using Precipitation Promoter

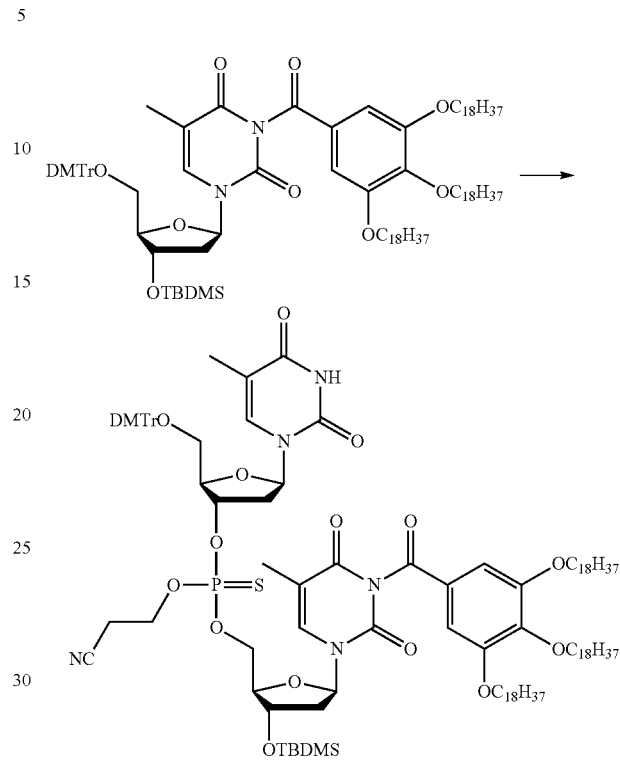

Under an argon atmosphere, 5'-O-(4,4'-dimethoxytrityl)-N3-3,4,5-tri(octadecyloxy)benzoyl-deoxythymidine-3'-yl-t-butyl-dimethylsilane (312 mg, 199 μmol), and 3,4,5-tri(octadecyloxy)benzyl acetate (287 mg, 300 μmol) which is the precipitation promoter synthesized in Example 7 were dissolved in dichloromethane (5.0 mL), indole (466 mg, 3.98 mmol), trifluoroacetic acid (30.6 μL, 398 μmol) were added and the mixture was stirred at room temperature for 2 hr, and completion of the reaction was confirmed by thin layer chromatography. The reaction mixture was neutralized with 1-methylimidazole (34.8 μL, 439 μmol), a solution of 5-benzylthio-1H-tetrazole (115 mg, 600 μmol), 5'-O-(4,4'-dimethoxytrityl)deoxythymidine-3'-[O-(2-cyanoethyl)-(N,N-diisopropyl)]-phosphoramidite (447 g, 600 μmol) in acetonitrile was added, and the mixture was stirred at room temperature for 60 min, and completion of the reaction was confirmed by thin layer chromatography. Furthermore, 3-[(N,N-dimethylaminomethylidene)amino]-3H-1,2,4-dithiazole-5-thione (136 mg, 662 μmol) was added and the mixture was stirred at room temperature for 30 min. Acetonitrile (30 mL) was added to the reaction solution, and the precipitated solid was suction-filtrated using Kiriyama funnel and dried to give 5'-O-(4,4'-dimethoxytrityl)-deoxythymidine-3'-[O-(2-cyanoethyl)]phosphorothionyl deoxythymidine-3'-yl [3,4,5-tri(octadecyloxy)benzyl] succinate (382 mg, yield 99%) as a white solid.

$^1$H-NMR (400 MHz, CDCl$_3$): δ=−0.01 (S, 3H, Si—CH$_3$), 0.00 (S, 3H, Si—CH$_3$), 0.75-0.81 (m, 18H, —OCH$_2$(CH$_2$)$_{15}$CH$_3$+Si-C(CH$_3$)$_3$) 1.05-1.73 (m, 90H, —OCH$_2$ (CH$_2$)$_{15}$CH$_3$), 2.08 (m, 1H, 2'-H), 2.22 (m, 1H, 2'-H), 2.34 (m, 1H, 2'-H), 2.53-2.62 (m, 2H, 2'-H+5'-H), 2.70 (t, 1H, J=6.0 Hz, 5'-H), 3.25-3.51 (m, 2H, 5'-H), 3.71 (d, 6H, J=1.3 Hz, DMTr-OCH$_3$), 3.87-3.98 (m, 7H, —OC

H₂(CH₂)₁₅CH₃+3'-H), 4.10-4.33 (m, 6H, —CH₂C H₂CN+2×4'-H)ᵣ, 5.25 (dt, 1H, J=7.9, 15.3 Hz, 3'-H), 6.17 (td, 1H, J=2.2, 6.6 Hz, 1'-H), 6.30 (dd, J=5.4, 8.8, 23.6 Hz, 1'-H), 6.76 (s, 2H, Ar—H), 6.78 (s, 2H, DMTr-H), 7.05-7.39 (m, 11H, DMTr-Ar—H), 7.39 (s, 1H, N6-H), 7.47 (d, 1H, J=8.0 Hz, N6-H), 8.45 (m, 1H, N3-H)

INDUSTRIAL APPLICABILITY

Using the precipitation promoter of the present invention, when precipitating an organic compound protected by an organic group having one or more aliphatic hydrocarbon groups having not less than 10 carbon atoms in a solvent, the recovery rate thereof can be improved. Therefore, the precipitation promoter of the present invention is useful for the synthesis of the organic compound, particularly, for the synthesis of oligonucleotide.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

atoms in the precipitation promoter is a group selected from a linear $C_{10\text{-}40}$ alkyl group and a linear $C_{10\text{-}40}$ alkenyl group.

3. The method according to claim 1, wherein the aliphatic hydrocarbon group having not less than 10 carbon atoms of the organic group is linear.

4. The method according to claim 1, wherein the aliphatic hydrocarbon group having not less than 10 carbon atoms of the organic group is a group selected from a linear $C_{10\text{-}40}$ alkyl group and a linear $C_{10\text{-}40}$ alkenyl group.

5. The method according to claim 1, wherein said precipitation promoter is:
(1) an organic compound having one or more structures represented by formula (G):

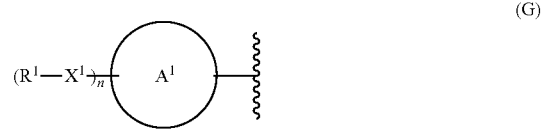

wherein
each $R^1$ is independently a linear $C_{10\text{-}40}$ alkyl group;
each $X^1$ is independently a single bond, —O—, —C(=O)—, —C(=O)O—, —OC(=O)—, —C(=O)NH— or —NHC(=O)—;
ring $A^1$ is an optionally substituted $C_{3\text{-}14}$ hydrocarbon ring; and
n is an integer of 1 to 4, or

The invention claimed is:

1. A method of precipitating an organic compound protected by an organic group having one or more aliphatic hydrocarbon groups having not less than 10 carbon atoms from a solvent, said method comprising:
mixing a precipitation promoter, said organic compound protected by an organic group, and said solvent, wherein
said precipitation promoter has one or more linear aliphatic hydrocarbon groups having not less than 10 carbon atoms, and
the aliphatic hydrocarbon group in the precipitation promoter has not less than 20 carbon atoms in total, and
said organic compound protected by an organic group is a nucleoside, nucleotide, or oligonucleotide optionally further protected by a protecting group used in nucleic acid synthesis, or an amino acid or peptide optionally further protected by a protecting group used in peptide synthesis.

2. The method according to claim 1, wherein the linear aliphatic hydrocarbon group having not less than 10 carbon (2) optionally substituted $C_{1\text{-}10}$ alkane having one or more linear $C_{10\text{-}40}$ alkyl groups via a group selected from the group consisting of —O—, —C(=O)—, —C(=O)O—, —OC(=O)—, —C(=O)NH— and —NHC(=O)—.

6. The method according to claim 1, wherein said precipitation promoter is:
(1) a compound represented by formula (I):

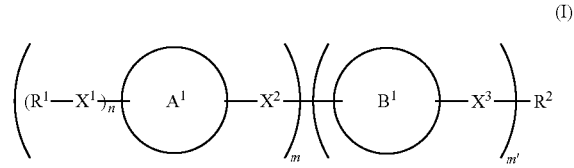

wherein
each $R^1$ is independently a linear $C_{10\text{-}40}$ alkyl group;

each $X^1$ is independently a single bond, —O—, —C(=O)—, —C(=O)O—, —OC(=O)—, —C(=O)NH— or —NHC(=O)—;

ring $A^1$ and ring $B^1$ are each independently an optionally substituted $C_{3-14}$ hydrocarbon ring;

each $X^2$ is independently —$(CH_2)_p$—, —$(CH_2)_p$—O—$(CH_2)_q$—, —$(CH_2)_p$—C(=O)—$(CH_2)_q$—, —$(CH_2)_p$—C(=O)O—$(CH_2)_q$—, —$(CH_2)_p$—OC(=O)—$(CH_2)_q$—, —$(CH_2)_p$—C(=O)NH—$(CH_2)_q$— or —$(CH_2)_p$—NHC(=O)—$(CH_2)_q$— (p and q are each independently an integer of 0 to 3);

$X^3$ is a single bond, —$(CH_2)_r$—O—, —$(CH_2)_r$—C(=O)—, —$(CH_2)_r$—C(=O)O—, —$(CH_2)_r$—OC(=O)—, —$(CH_2)_r$—C(=O)NH— or —$(CH_2)_r$—NHC(=O)— (r is an integer of 0 to 3);

$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted monocyclic heterocyclic group or a tri($C_{1-6}$ alkyl)silyl group;

n and m are each independently an integer of 1 to 4;

m' is 0 or 1 when m is 1, and 1 when m is 2, 3 or 4, or (2) optionally substituted $C_{1-10}$ alkane having one or more linear $C_{10-40}$ alkyl groups via a group selected from the group consisting of —O—, —C(=O)—, —C(=O)O—, —OC(=O)—, —C(=O)NH— and —NHC(=O)—.

7. The method according to claim 6, wherein $R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, or an optionally substituted monocyclic heterocyclic group.

8. The method according to claim 1, wherein the precipitation promoter is a compound represented by formula (II):

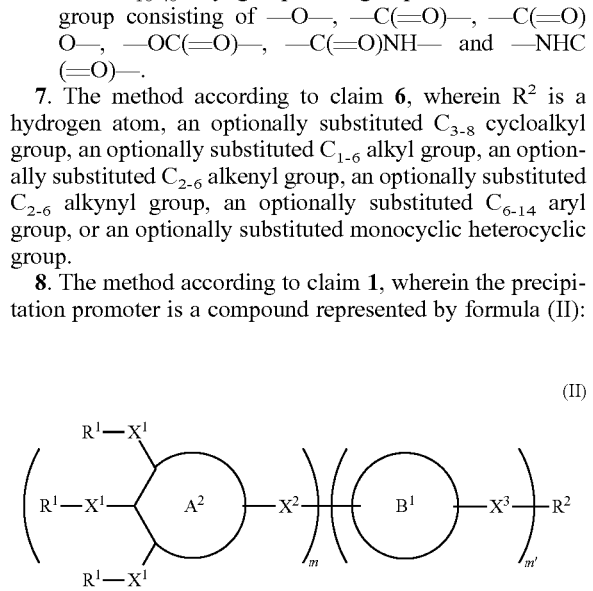

(II)

wherein
each $R^1$ is independently a linear $C_{10-40}$ alkyl group;
each $X^1$ is independently a single bond, —O—, —C(=O)—, —C(=O)O—, —OC(=O)—, —C(=O)NH— or —NHC(=O)—;

ring $A^2$ and ring $B^1$ are each independently an optionally substituted $C_{3-14}$ hydrocarbon ring;

each $X^2$ is independently —$(CH_2)_p$—, —$(CH_2)_p$—O—$(CH_2)_q$—, —$(CH_2)_p$—C(=O)($CH_2)_q$—, —$(CH_2)_p$—C(=O)O—$(CH_2)_q$—, —$(CH_2)_p$—OC(=O)—$(CH_2)_q$—, —$(CH_2)_p$—C(=O)NH—$(CH_2)_q$— or —$(CH_2)_p$—NHC(=O)—$(CH_2)_q$— (p and q are each independently an integer of 0 to 3);

$X^3$ is a single bond, —$(CH_2)_r$—O—, —$(CH_2)_r$—C(=O)—, —$(CH_2)_r$—C(=O)O—, —$(CH_2)_r$—OC(=O)—, —$(CH_2)_r$—C(=O)NH— or —$(CH_2)_r$—NHC(=O)— (r is an integer of 0 to 3);

$R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, an optionally substituted monocyclic heterocyclic group, or a tri($C_{1-6}$ alkyl)silyl group;

m is an integer of 1 to 4; and
m' is 0 or 1 when m is 1, and 1 when m is 2, 3 or 4.

9. The method according to claim 8, wherein $R^2$ is a hydrogen atom, an optionally substituted $C_{3-8}$ cycloalkyl group, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aryl group, or an optionally substituted monocyclic heterocyclic group.

10. The method according to claim 5, wherein the $C_{3-14}$ hydrocarbon ring is a benzene ring or a cyclohexane ring.

11. The method according to claim 1, wherein said organic group is a group represented by formula (III):

wherein
** shows a bonding position to a group to be protected;
L is a single bond, or a group represented by formula (a1) or (a1'):

wherein
* shows the bonding position to Y;
** is as defined above;
$R^8$ and $R^9$ are each independently a $C_{1-22}$ hydrocarbon group;
$L_1$ is a divalent $C_{1-22}$ hydrocarbon group; and
$L_2$ is a single bond, or a group represented by C(=O)N($R^{2'}$)—$R^{1'}$—N($R^3$)* wherein  shows the bonding position to $L_1$, * shows the bonding position to C=O, $R^{1'}$ is a $C_{1-22}$ alkylene group, and $R^{2'}$ and $R^3$ are each independently a hydrogen atom or a $C_{1-22}$ alkyl group, or $R^{2'}$ and $R^3$ are optionally joined to form a ring, Y is a single bond, an oxygen atom or NR wherein R is a hydrogen atom, an alkyl group or an aralkyl group, and Z is a group represented by formula (a2), formula (a2') or formula (a2"):

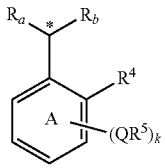
(a2)

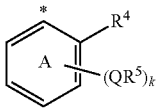
(a2')

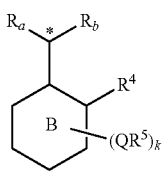
(a2")

wherein
* shows a bonding position;
$R^4$ is a hydrogen atom, or when $R_b$ is a group represented by the following formula (a3), optionally joined with $R^6$ of ring C to show a single bond or —O— and to form a fused ring together with ring A or ring B and ring C;
each Q in the number of k is independently —O—, —C(=O)—, —C(=O)O—, —OC(=O)—, —C(=O)NH— or —NHC(=O)—;
each $R^5$ in the number of k is independently a hydrocarbon group bonded via a single bond or a linker to an aliphatic hydrocarbon group having not less than 10 carbon atoms;
k is an integer of 1 to 4;
ring A and ring B each independently optionally further have, in addition to $QR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom;
$R_a$ is a hydrogen atom, or a phenyl group optionally substituted by a halogen atom; and
$R_b$ is a hydrogen atom, or a group represented by formula (a3):

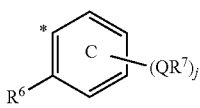
(a3)

wherein
* shows a bonding position;
j is an integer of 0 to 4;
each Q in the number of j is independently as defined above;
each $R^7$ in the number of j is independently a hydrocarbon group bonded via a single bond or a linker to an aliphatic hydrocarbon group having not less than 10 carbon atoms;

$R^6$ is a hydrogen atom, or optionally joined with $R^4$ of ring A or ring B to show a single bond or —O— and to form a fused ring together with ring A or ring B and ring C; and
ring C optionally further has, in addition to $OR^7$ in the number of j, substituent(s) selected from the group consisting of a halogen atom, a $C_{1-6}$ alkyl group optionally substituted by a halogen atom, and a $C_{1-6}$ alkoxy group optionally substituted by a halogen atom, or
$R_a$ and $R_b$ are joined to form an oxo group.

12. The method according to claim 11, wherein Z is a group represented by formula (a2) or formula (a2'), the fused ring is a fluorene ring or a xanthene ring, each $R^5$ in the number of k is independently a hydrocarbon group bonded via a single bond or a linker to a linear aliphatic hydrocarbon group having not less than 10 carbon atoms, each $R^7$ in the number of j is independently a hydrocarbon group bonded via a single bond or a linker to a linear aliphatic hydrocarbon group having not less than 10 carbon atoms, and $R_a$ is a hydrogen atom, or $R_a$ and $R_b$ are joined to form an oxo group.

13. The method according to claim 11, wherein L is a group represented by formula (a1), $L_1$ is a divalent $C_{1-22}$ hydrocarbon group, and $L_2$ is a single bond.

14. The method according to claim 11, wherein L is a group represented by formula (a1'), $L_1$ is a phenylene group, and $L_2$ is a single bond.

15. The method according to claim 11, wherein Y is an oxygen atom.

16. The method according to claim 11, wherein Z is a group represented by formula (a2), and $R^4$ is a hydrogen atom.

17. The method according to claim 11, wherein Z is a group represented by formula (a2), and $R_a$ and $R_b$ are each a hydrogen atom.

18. The method according to claim 11, wherein L and Y are each a single bond, Z is a group represented by formula (a2), $R^4$ is a hydrogen atom, and $R_a$ and $R_b$ are joined to form an oxo group.

19. A precipitation mixture obtained by a method according to claim 1, comprising said precipitation promoter, and said organic compound protected by an organic group having one or more aliphatic hydrocarbon groups having not less than 10 carbon atoms.

20. The precipitation mixture according to claim 19, wherein the aliphatic hydrocarbon group having not less than 10 carbon atoms of the organic group is linear.

21. The method according to claim 1, wherein the solvent comprises a polar solvent.

22. The method according to claim 21, wherein the polar solvent is acetonitrile.

23. The method according to claim 1, wherein the solvent comprising a polar solvent is a mixed solvent of a polar solvent and a nonpolar solvent.

24. The method according to claim 23, wherein the polar solvent is acetonitrile.

25. The method according to claim 1, wherein the organic compound protected by the organic group is a nucleoside, nucleotide, or oligonucleotide optionally further protected by a protecting group used in nucleic acid synthesis.

26. The method according to claim 1, wherein the organic compound protected by the organic group is a nucleoside or oligonucleotide wherein at least one group selected from an amino group and an imino group of a nucleic acid base, a 2'-hydroxy group of a ribose residue, a 3'-hydroxy group of a ribose residue, and a 3'-hydroxy group of a deoxyribose residue is protected by the organic group, and other group is optionally further protected by a protecting group used in nucleic acid synthesis.

27. The method according to claim 1, wherein said precipitation promoter is used at not less than 0.1 molar equivalent relative to the organic compound protected by the organic group to precipitate the organic compound protected by the organic group.

28. A production method of an oligonucleotide, comprising:
adding a polar solvent to a reaction solution comprising an oligonucleotide wherein at least one group is protected by an organic group having one or more aliphatic hydrocarbon groups having not less than 10 carbon atoms, and other group is optionally further protected by a protecting group used in nucleic acid synthesis, and a precipitation promoter in a nonpolar solvent; and
separating a precipitate mixture comprising the oligonucleotide and the precipitation promoter from the reaction solution, wherein
the precipitation promoter has one or more linear aliphatic hydrocarbon groups having not less than 10 carbon atoms, and
the aliphatic hydrocarbon group in the precipitation promoter has not less than 20 carbon atoms in total.

29. The production method according to claim 28, wherein the polar solvent is acetonitrile.

30. The production method according to claim 28, wherein the aliphatic hydrocarbon group having not less than 10 carbon atoms of the organic group is linear.

31. The production method according to claim 28, which is performed by a phosphoramidite method.

32. A production method of an oligonucleotide, which comprises one repeat of production cycle comprising the following (1) to (3), or plural repeats thereof by a phosphoramidite method, which comprises the following (4) in the first cycle, the following (5) in each cycle, and the following (6) in each cycle except the final cycle:
(1) obtaining a reaction solution comprising a free-5'-hydroxy-group form by adding an acid to a reaction solution comprising a nucleoside or oligonucleotide wherein at least one group selected from an amino group and an imino group of a nucleic acid base, 2'- and 3'-hydroxy groups of a ribose residue, and 3'-hydroxy group of a deoxyribose residue is protected by an organic group having one or more aliphatic hydrocarbon groups having not less than 10 carbon atoms, a 5'-hydroxy group is protected by a temporary protecting group removable under acidic conditions, and other group is optionally further protected by a protecting group used in nucleic acid synthesis in a nonpolar solvent, to deprotect the temporary protecting group of the 5'-hydroxy group, and neutralizing same with a base;
(2) obtaining a reaction solution comprising a phosphite triester form, by adding nucleoside or oligonucleotide wherein a 3'-hydroxy group is phosphoramidited, a 5'-hydroxy group is protected by a temporary protecting group removable under acidic conditions, and other group is optionally further protected by a protecting group used in nucleic acid synthesis to the reaction solution comprising the free-5'-hydroxy-group form in a nonpolar solvent;
(3) obtaining a reaction solution comprising an oligonucleotide wherein at least one group selected from an amino group and an imino group of a nucleic acid base, 2'- and 3'-hydroxy groups of a ribose residue, and 3'-hydroxy group of a deoxyribose residue is protected by said organic group, a 5'-hydroxy group is protected by a temporary protecting group removable under acidic conditions, and other group is optionally further protected by a protecting group used in nucleic acid synthesis, by adding an oxidizing agent or a sulfurizing agent to the reaction solution comprising the phosphite triester form in a nonpolar solvent;
(4) adding a precipitation promoter to the reaction solution at any of before said (1), between said (1) and (2), between said (2) and (3) and said step (3);
(5) separating a precipitation mixture comprising the free-5'-hydroxy-group form, the phosphite triester form or the oligonucleotide, and the precipitation promoter from the reaction solution by adding a polar solvent to the reaction solution comprising the precipitation promoter at after said (4), and any of between said (1) and (2), between said (2) and (3) and said step (3);
(6) adding a nonpolar solvent to the precipitation mixture obtained in said (5) to give a reaction solution, wherein
the precipitation promoter has one or more linear aliphatic hydrocarbon groups having not less than 10 carbon atoms, and
the aliphatic hydrocarbon group in the precipitation promoter has not less than 20 carbon atoms in total.

33. The method according to claim 32, wherein the polar solvent is acetonitrile.

34. The method according to claim 32, wherein the aliphatic hydrocarbon group having not less than 10 carbon atoms of the organic group is linear.

35. The method according to claim 32, wherein said (5) and (6) are performed after said (3).

36. The method according to claim 32, further comprising (7):
(7) a step of removing all protecting groups of the oligonucleotide and isolating the oligonucleotide.

37. The method according to claim 32, wherein the non-polar solvent is a solvent selected from the group consisting of a halogenated solvent, an aromatic solvent, an ester solvent, an aliphatic solvent, and a combination thereof.

* * * * *